(12) United States Patent
Mastracchio et al.

(10) Patent No.: US 9,181,239 B2
(45) Date of Patent: Nov. 10, 2015

(54) PYRIDOPYRIMIDINONE INHIBITORS OF KINASES

(71) Applicant: AbbVie Inc., North Chicago, IL (US)

(72) Inventors: Anthony Mastracchio, Waukegan, IL (US); Chunqiu Lai, Libertyville, IL (US); Thomas D. Penning, Elmhurst, IL (US)

(73) Assignee: AbbVie Inc., North Chicago, IL (US)

( * ) Notice: Subject to any disclaimer, the term of this patent is extended or adjusted under 35 U.S.C. 154(b) by 164 days.

(21) Appl. No.: 13/655,164

(22) Filed: Oct. 18, 2012

(65) Prior Publication Data

US 2013/0102590 A1    Apr. 25, 2013

Related U.S. Application Data

(60) Provisional application No. 61/549,294, filed on Oct. 20, 2011.

(51) Int. Cl.
*C07D 471/04*    (2006.01)
*A61K 31/519*    (2006.01)
*A61P 35/00*    (2006.01)

(52) U.S. Cl.
CPC .................................. *C07D 471/04* (2013.01)

(58) Field of Classification Search
CPC ............................ C07D 471/04; A61K 31/519
USPC ..................................... 544/279; 514/264.11
See application file for complete search history.

(56) References Cited

FOREIGN PATENT DOCUMENTS

WO    2007126122 A1    11/2007
WO    2008055013 A2     5/2008

OTHER PUBLICATIONS

Glotzer M., et al., "Cyclin is Degraded by the Ubiquitin Pathway," Nature, 1991, vol. 349 (6305), pp. 132-138.
Hashimoto O., et al., "Cell cycle Regulation by the Wee1 Inhibitor PD0166285, Pyrido [2,3-d] Pyimidine, in the B16 Mouse Melanoma Cell Line," Bio Medical Center Cancer, 2006, 6:292.
International Search Report for Application No. PCT/US2012/060860, mailed on Dec. 4, 2012, 4 pages.
Leijen S., et al., "Abrogation of the G2 Checkpoint by Inhibition of Wee-1 Kinase Results in Sensitization of p53-deficient Tumor Cells to DNA-damaging Agents," Current Clinical Pharmacology, 2010, vol. 5 (3), pp. 186-191.
Lindqvist A., et al., "The Decision to Enter Mitosis: Feedback and Redundancy in the Mitotic Entry Network," Journal of Cell Biology, 2009, vol. 185 (2), pp. 193-202.
McGowan C.H., et al., "Human Wee1 Kinase Inhibits Cell Division by Phosphorylating p34cdc2 Exclusively on Tyr15," The EMBO Journal, 1993, vol. 12 (1), pp. 75-85.
Nigro J.M., et al., "Mutations in the p53 Gene Occur in Diverse Human Tumour Types," Nature, 1989, vol. 342 (6250), pp. 705-708.
Nurse P., "Universal Control Mechanism Regulating Onset of M-Phase," Nature, 1990, vol. 344 (6266), pp. 503-508.
O'Connell M.J., et al., "Chk1 is a Wee1 Kinase in the G2 DNA Damage Checkpoint Inhibiting Cdc2 by Y15 Phosphorylation," The EMBO Journal, 1997, vol. 16 (3), pp. 545-554.
Palmer B.D., et al., "Structure-Activity Relationships for 2-anilino-6-phenylpyrido[2,3-d]pyrimidin-7(8H)-ones as Inhibitors of the Cellular Checkpoint Kinase Wee1," Bioorganic & Medicinal Chemistry Letters, 2005, vol. 15 (7), pp. 1931-1935.
Parker L.L., et al., "Inactivation of the p34cdc2-Cyclin B Complex by the Human WEE1 Tyrosine Kinase," Science, 1992, vol. 257 (5078), pp. 1955-1957.
Pure and Applied Chemistry, "Rules for the Nomenclature of Organic Chemistry," Section E: Stereochemistry, IUPAC Commission on Nomenclature of Organic Chemistry, Pergamon Press, 1976, vol. 45, pp. 13-30.
Sancar A., et al., "Molecular Mechanisms of Mammalian DNA Repair and the DNA Damage Checkpoints," Annual Review of Biochemistry, 2004, vol. 73, pp. 39-85.
Stumpff J., et al., "*Drosophila* Wee1 Kinase Regulates Cdk1 and Mitotic Entry during Embryogenesis," Current Biology, 2004, vol. 14 (23), pp. 2143-2148.
Sutton, V.R. et al., "Bcl-2 Prevents Apoptosis Induced by Perforin and Granzyme B, but Not That Mediated by Whole Cytotoxic Lymphocytes," Journal of Immunology, 1997, vol. 158 (12), pp. 5783-5790.
Wang Y., et al., "Knockdown of Chk1, Wee1 and Myt1 by RNA Interference Abrogates G2 Checkpoint and Induces Apoptosis," Cancer Biology & Therapy, 2004, vol. 3 (3), pp. 305-313.
Zhang K., et al., "Overexpression of RRM2 Decreases Thrombspondin-1 and Increases VEGF Production in Human Cancer Cells in Vitro and in Vivo: Implication of RRM2 in Angiogenesis," Molecular Cancer, 2009, 8:11.

*Primary Examiner* — Susanna Moore
(74) *Attorney, Agent, or Firm* — Changxia Sun

(57) ABSTRACT

Compounds of formula (I), and pharmaceutical acceptable salts thereof,

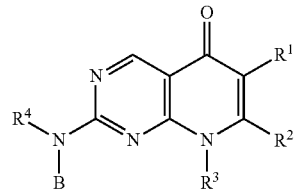

formula (I)

which inhibit the activity of kinases such as Wee-1 kinase are described. Also described are methods of making the compounds, compositions containing the compounds, and methods of treatment using the compounds.

22 Claims, No Drawings

PYRIDOPYRIMIDINONE INHIBITORS OF KINASES

REFERENCE TO RELATED APPLICATIONS

This application claims priority to U.S. provisional application No. 61/549,294, filed Oct. 20, 2011, the entire contents of which are incorporated herein by reference.

FIELD OF THE INVENTION

This invention pertains to compounds which inhibit the activity of Wee-1 kinase, methods of making the compounds, compositions containing the compounds, and methods of treatment using the compounds.

BACKGROUND OF THE INVENTION

In order to undergo proper cell division, eukaryotic cells must faithfully replicate their genome and then correctly segregate their chromosomes into two daughter cells. This process of cell division, also called the cell cycle, is a step-wise process that is governed by checkpoints to ensure genomic integrity. Upon completion of DNA replication (S-phase), cells enter a growth phase (G2-phase) prior to proceeding into mitosis for chromosome segregation (M-phase). A key regulator of mitosis is the kinase Cdk1 (as called Cdc2) (Nurse, P. (1990) Universal control mechanism regulating onset of M-phase. Nature 344, 503-508). Activation of Cdk1 results in the onset of mitosis, and its subsequent inactivation initiates the exit from mitosis. Cdk1 is activated by the binding of Cyclin A or Cyclin B. Both Cyclin A-Cdk1 and Cyclin B-Cdk1 complexes function to initiate mitosis (Lindqvist, A., et. Al. (2009) The decision to enter mitosis: feedback and redundancy in the mitotic entry network. The Journal of cell biology 185, 193-202). The degradation of Cyclin B triggers the inactivation of Cdk1, resulting in the mitotic exit and entry into a growth (G1) phase prior to beginning a new round of the cell cycle (Glotzer, M., et al. (1991) Cyclin is degraded by the ubiquitin pathway. Nature 349, 132-138).

In addition to Cyclins, Cdk1 is also regulated by Wee1, an atypical tyrosine kinase that phosphorylates Cdk1 on tyrosine 15 (Y15) and inactivates Cdk1 (McGowan, C. H., et al. (1993) Human Wee1 kinase inhibits cell division by phosphorylating p34cdc2 exclusively on Tyr15. The EMBO journal 12, 75-85; Parker, L. L., et al. (1992) Inactivation of the p34cdc2-cyclin B complex by the human WEE1 tyrosine kinase. Science 257, 1955-1957). Wee1 is a critical negative regulator of Cdk1 and functions at the G2-M phase checkpoint to ensure that DNA replication has been completed and the genome is not damaged prior to entering mitosis (O'Connell, et al. (1997) Chk1 is a wee1 kinase in the G2 DNA damage checkpoint inhibiting cdc2 by Y15 phosphorylation. The EMBO journal 16, 545-554). Loss of Wee1 can result in premature entry into mitosis, resulting in mitotic catastrophe and cell death (Stumpff, J., et al. (2004) Drosophila Wee1 kinase regulates Cdk1 and mitotic entry during embryogenesis. Curr Biol 14, 2143-2148). Furthermore, many cancers are defective in their G1-phase checkpoints and are reliant on G2-M phase checkpoints (Sancar, A., et al. (2004) Molecular mechanisms of mammalian DNA repair and the DNA damage checkpoints. Annual review of biochemistry 73, 39-85). Indeed, loss of expression of Wee1 has been shown to lead to the abrogation of the G2-M phase checkpoint and sensitize tumor cells to DNA damage, especially tumors that have lost their G1-phase checkpoint due to a deficiency in the p53 protein (Wang, Y., et al. (2004) Knockdown of Chk1, Wee1 and Myt1 by RNA interference abrogates G2 checkpoint and induces apoptosis. Cancer biology & therapy 3, 305-313).

Inhibitors of Wee1 have the potential to selectively cause lethality in cancerous cells that are defective in other cell cycle checkpoints, while sparing normal tissues that can activate other cell cycle checkpoints. Thus, small molecule inhibitors of Wee1 would be beneficial for therapeutic intervention in cancer and other cell proliferative disorders.

SUMMARY OF THE INVENTION

The present invention has numerous embodiments. One embodiment of this invention, therefore, pertains to compounds that have formula (I)

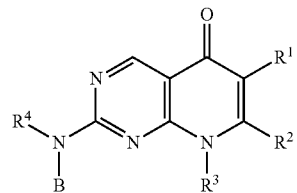

formula (I)

wherein B, $R^1$, $R^2$, $R^3$, and $R^4$ are as defined below and subsets therein.

Also provided are pharmaceutically acceptable compositions, comprising a therapeutically effective amount of a compound of formula (I) and a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). Another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)) oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Embodiments of Formula (I)

In one embodiment, the present invention is directed, in part, to a class of compounds having a structure of formula (I):

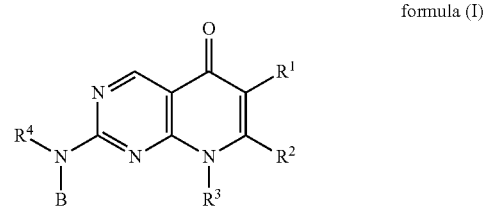

formula (I)

wherein

B is (a) $C_{3-8}$ cycloalkyl, phenyl, naphthyl, tetrahydronaphthyl, indenyl, or indanyl, wherein the $C_{3-8}$ cycloalkyl, phenyl, naphthyl, tetrahydronaphthyl, indenyl, or indanyl is optionally substituted with one or more $R^5$; or (b) 5-16 membered monocyclic, bicyclic, or tricyclic heterocyclyl, wherein the heterocyclyl is optionally substituted with one or more $R^6$;

$R^1$ is hydrogen, $C_{1-8}$-alkyl, $C_{2-8}$-alkenyl, $C_{2-8}$-alkynyl, $C_{3-8}$-cycloalkyl, aryl, heteroaryl, aryl-$C_{1-6}$-alkyl-, $C_{3-8}$ cycloalkyl-$C_{1-6}$-alkyl-, or heteroaryl-$C_{1-6}$-alkyl-; wherein (a) the $C_{1-8}$-alkyl, $C_{2-8}$-alkenyl, or $C_{2-8}$-alkynyl, alone or as part of another moiety, is optionally substituted with one or more substituents selected from the group consisting of CN, $NO_2$, halo, —$OR^a$, —$C(O)R^a$, —$C(O)OR^a$, —$OC(O)R^a$, —$NR^bR^c$, $NR^bC(O)R^a$, —$NHC(O)NHR^b$, —$C(O)NR^bR^c$, —$NHSO_2R^a$, and —$SO_2NR^bNR^c$; and (b) the $C_{3-8}$-cycloalkyl, aryl, or heteroaryl is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —$C(O)R^d$, —C(O)OR$^d$, —OC(O)R$^d$, —SR$^d$, —S(O)R$^d$, —SO$_2$R$^d$, —NR$^e$R$^f$, —NHC(O)R$^e$, —NHC(O)NHR$^e$, —NHC(O)OR$^e$, —NHSO$_2$R$^d$, —C(O)NHR$^e$, and —SO$_2$NHNR$^e$;

R$^2$ is hydrogen, C$_{1-6}$-alkyl, C$_{3-8}$ cycloalkyl, aryl, heteroaryl, heterocycloalkyl, aryl-C$_{1-6}$-alkyl-, cycloalkyl-C$_{1-6}$-alkyl-, heteroaryl-C$_{1-6}$-alkyl-, or heterocycloalkyl-C$_{1-6}$-alkyl-, wherein the C$_{1-6}$-alkyl is optionally substituted with one or more substituents selected from the group consisting of halo, hydroxy, C$_{1-6}$-alkoxy, —NH$_2$, —NHC$_{1-6}$-alkyl, and —N(C$_{1-6}$-alkyl)$_2$, and wherein the C$_{3-8}$ cycloalkyl, aryl, heteroaryl, or heterocycloalkyl, alone or as part of another moiety, is optionally substituted with one or more substituents selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and N(C$_{1-6}$-alkyl)$_2$;

R$^3$ is hydrogen, C$_{1-6}$-alkyl, C$_{3-8}$ cycloalkyl, aryl, heteroaryl, heterocycloalkyl, aryl-C$_{1-6}$-alkyl-, cycloalkyl-C$_{1-6}$-alkyl-, heteroaryl-C$_{1-6}$-alkyl-, or heterocycloalkyl-C$_{1-6}$-alkyl-, wherein the C$_{1-6}$-alkyl is optionally substituted with one or more substituents selected from the group consisting of halo, hydroxy, C$_{1-6}$-alkoxy, —NH$_2$, —NHC$_{1-6}$-alkyl, and —N(C$_{1-6}$-alkyl)$_2$, and wherein the C$_{3-8}$ cycloalkyl, aryl, heteroaryl, or heterocycloalkyl, alone or as part of another moiety, is optionally substituted with one or more substituents selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and N(C$_{1-6}$-alkyl)$_2$;

or R$^2$ and R$^3$ can be joined together to form a 5-8 membered heterocyclic ring, wherein the ring is optionally substituted with one or more substituents selected from the group consisting of halo, C$_{1-6}$-alkyl, C$_{1-6}$-haloalkyl, C$_{1-6}$-hydroxyalkyl, hydroxy, C$_{1-6}$-alkoxy, C$_{1-6}$-haloalkoxy, —NH$_2$, —NH(C$_{1-6}$-alkyl), and N(C$_{1-6}$-alkyl)$_2$;

R$^4$ is hydrogen or C$_{1-6}$-alkyl;

R$^5$, at each occurrence, is independently CN, NO$_2$, halo, C$_{1-6}$-alkyl, C$_{1-6}$-haloalkyl, OR$^g$, SR$^g$, C(O)R$^g$, C(O)NR$^h$R$^i$, C(O)OR$^g$, NR$^h$R$^i$, NR$^h$C(O)R$^g$, S(O)$_2$R$^g$, NR$^h$S(O)$_2$R$^g$, S(O)$_2$NR$^h$R$^i$, aryl, cycloalkyl, heteroaryl, heterocycloalkyl, aryl-C$_{1-6}$-alkyl-, cycloalkyl-C$_{1-6}$-alkyl-, heteroaryl-C$_{1-6}$-alkyl-, or heterocycloalkyl-C$_{1-6}$-alkyl-; wherein the aryl, cycloalkyl, heteroaryl, or heterocycloalkyl, alone or as part of another moiety, is optionally substituted with one or more R$^7$;

R$^6$, at each occurrence, is independently CN, NO$_2$, halo, C$_{1-6}$-alkyl, C$_{1-6}$-haloalkyl, cycloalkyl, heterocycloalkyl, or C$_{1-4}$-alkyl-heterocycloalkyl-; R$^j$, SR$^j$, C(O)R$^j$, C(O)NR$^k$R$^l$, C(O)OR$^j$, NR$^k$R$^l$, NR$^k$C(O)R$^j$, S(O)$_2$R$^j$, NR$^k$S(O)$_2$RJ, or S(O)$_2$NR$^k$R$^l$;

R$^7$, at each occurrence, is independently CN, NO$_2$, halo, C$_{1-6}$-alkyl, C$_{1-6}$-haloalkyl, C$_{1-6}$-alkyl-N(C$_{1-6}$-allyl)$_2$, OR$^m$, SR$^m$, C(O)R$^m$, C(O)NR$^n$R$^o$, C(O)OR$^m$, NR$^n$R$^o$, NR$^n$C(O)R$^m$, S(O)$_2$R$^m$, NR$^n$S(O)$_2$R$^m$, or S(O)$_2$NR$^m$R$^o$;

R$^a$, at each occurrence, is independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^b$ and R$^c$, at each occurrence, are independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^d$, at each occurrence, is independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^e$ and R$^f$, at each occurrence, are independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^g$, at each occurrence, is independently selected from the group consisting of hydrogen, C$_{1-6}$ alkyl, aryl, C$_{3-8}$ cycloalkyl, heteroaryl, and heterocycloalkyl; wherein the C$_{1-6}$-alkyl is optionally substituted with one or more substituents selected from the group consisting of halo, hydroxy, C$_{1-6}$-alkoxy, —NH$_2$, —NHC$_{1-6}$-alkyl, and —N(C$_{1-6}$-alkyl)$_2$, and wherein the aryl, C$_{3-8}$ cycloalkyl, heteroaryl, and heterocycloalkyl are optionally substituted with one or more substituents selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and —N(C$_{1-6}$-alkyl)$_2$;

R$^h$ and R$^i$, at each occurrence, are independently selected from the group consisting of hydrogen, C$_{1-6}$ alkyl, aryl, C$_{3-8}$ cycloalkyl, heteroaryl, and heterocycloalkyl; wherein the C$_{1-6}$-alkyl is optionally substituted with one or more substituents selected from the group consisting of halo, hydroxy, C$_{1-6}$-alkoxy, —NH$_2$, —NHC$_{1-6}$-alkyl, and —N(C$_{1-6}$-alkyl)$_2$, and wherein the aryl, C$_{3-8}$ cycloalkyl, heteroaryl, and heterocycloalkyl are optionally substituted with one or more substituents selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and —N(C$_{1-6}$-alkyl)$_2$;

R$^j$, at each occurrence, is independently selected from the group consisting of hydrogen, C$_{1-6}$ alkyl, aryl, C$_{3-8}$ cycloalkyl, heteroaryl, and heterocycloalkyl; wherein the C$_{1-6}$-alkyl is optionally substituted with one or more substituents selected from the group consisting of halo, hydroxy, C$_{1-6}$-alkoxy, —NH$_2$, —NHC$_{1-6}$-alkyl, and —N(C$_{1-6}$-alkyl)$_2$, and wherein the aryl, C$_{3-8}$ cycloalkyl, heteroaryl, and heterocycloalkyl are optionally substituted with one or more substituents selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and —N(C$_{1-6}$-alkyl)$_2$;

R$^k$ and R$^l$, at each occurrence, are independently selected from the group consisting of hydrogen, C$_{1-6}$ alkyl, aryl, C$_{3-8}$ cycloalkyl, heteroaryl, and heterocycloalkyl; wherein the C$_{1-6}$-alkyl is optionally substituted with one or more substituents selected from the group consisting of halo, hydroxy, C$_{1-6}$-alkoxy, —NH$_2$, —NHC$_{1-6}$-alkyl, and —N(C$_{1-6}$-alkyl)$_2$, and wherein the aryl, C$_{3-8}$ cycloalkyl, heteroaryl, and heterocycloalkyl are optionally substituted with one or more substituents selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and —N(C$_{1-6}$-alkyl)$_2$;

R$^m$, at each occurrence, is independently selected from the group consisting of hydrogen, C$_{1-6}$ alkyl, C$_{1-6}$ haloalkyl, aryl, C$_{3-8}$ cycloalkyl, heteroaryl, and heterocycloalkyl; and R$^n$ and R$^o$, at each occurrence, are independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

or a pharmaceutically acceptable salt or solvate thereof.

In one embodiment of formula (I), R$^1$ is C$_{1-8}$-alkyl or C$_{2-8}$-alkenyl, wherein the C$_{1-8}$-alkyl or C$_{2-8}$-alkenyl is optionally substituted with one or more substituents independently selected from the group consisting of halo, CN, NO$_2$, —OR$^a$, —C(O)R$^a$, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, and —SO$_2$NR$^b$NR$^c$. In another embodiment of formula (I), R$^1$ is C$_{1-8}$-alkyl or C$_{2-8}$-alkenyl, wherein the C$_{1-8}$-alkyl or C$_{2-8}$-alkenyl is unsubstituted. In yet another embodiment of formula (I), R$^1$ is —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —CH$_2$CH═CH$_2$, CH$_2$CH═CHCH$_2$, or —CH$_2$CH$_2$CH═CH$_2$.

In one embodiment of formula (I), $R^1$ is $C_{3-8}$-cycloalkyl, aryl, or heteroaryl, wherein the $C_{3-8}$-cycloalkyl, aryl, or heteroaryl is optionally substituted with one, two, or three substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, NO$_2$, —OR$^d$, —C(O)R$^d$, —C(O)OR$^d$, —OC(O)R$^d$, —SR$^d$, —S(O)R$^d$, —SO$_2$R$^d$, —NR$^e$R$^f$, —NHC(O)R$^e$, —NHC(O)NHR$^e$, —NHC(O)OR$^e$, —NHSO$_2$R$^d$, —C(O)NHR$^e$, and —SO$_2$NHNR$^e$.

In another embodiment of formula (I), $R^1$ is 4-8 membered monocyclic heteroaryl, wherein the heteroaryl is optionally substituted with one, two, or three substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, NO$_2$, —OR$^d$, —C(O)R$^d$, —C(O)OR$^d$, —OC(O)R$^d$, —SR$^d$, —S(O)R$^d$, —SO$_2$R$^d$, —NR$^e$R$^f$, —NHC(O)R$^e$, —NHC(O)NHR$^e$, —NHC(O)OR$^e$, —NHSO$_2$R$^d$, —C(O)NHR$^e$, and —SO$_2$NHNR$^e$. In another embodiment, the heteroaryl is unsubstituted. In yet another embodiment of formula (I), $R^1$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl.

In another embodiment of formula (I), $R^1$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, NO$_2$, —OR$^d$, —C(O)R$^d$, —C(O)OR$^d$, —OC(O)R$^d$, —SR$^d$, —S(O)R$^d$, —SO$_2$R$^d$, —NR$^e$R$^f$, —NHC(O)R$^e$, —NHC(O)NHR$^e$, —NHC(O)OR$^e$, —NHSO$_2$R$^d$, —C(O)NHR$^e$, and —SO$_2$NHNR$^e$.

In another embodiment of formula (I), $R^1$ is phenyl, wherein the phenyl is optionally substituted with one, two, or three substituents independently selected from the group consisting of CN, NO$_2$, halo, —OR$^a$, —C(O)OR$^a$, —NR$^b$R$^c$, —NR$^b$C(O)R$^a$, and —C(O)NR$^b$R$^c$. In yet another embodiment, the phenyl is unsubstituted. In yet another embodiment, the phenyl is substituted with one, two, or three halo.

In one embodiment of formula (I), $R^2$ is hydrogen.

In one embodiment of formula (I), $R^2$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —NH$_2$, —NH($C_{1-6}$-alkyl), and —N($C_{1-6}$-alkyl)$_2$. In yet another embodiment of formula (I), $R^2$ is phenyl.

In one embodiment of formula (I), $R^2$ is $C_{1-6}$-alkyl or $C_{3-8}$ cycloalkyl, wherein the $C_{1-6}$-alkyl or $C_{3-8}$ cycloalkyl is unsubstituted. In another embodiment, the $C_{1-6}$-alkyl is optionally substituted with one, two, or three substituents independently selected from the group consisting of halo, hydroxy, $C_{1-6}$-alkoxy, —NH$_2$, —NHC$_{1-6}$-alkyl, and —N($C_{1-6}$-alkyl)$_2$. In yet another embodiment, $C_{3-8}$-cycloalkyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —NH$_2$, —NH($C_{1-6}$-alkyl), and N($C_{1-6}$-alkyl)$_2$.

In one embodiment of formula (I), $R^3$ is hydrogen.

In one embodiment of formula (I), $R^3$ is aryl, $C_{3-8}$ cycloalkyl, heteroaryl, or heterocycloalkyl, wherein the aryl, $C_{3-8}$ cycloalkyl, heteroaryl, or heterocycloalkyl is optionally substituted with one or more substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —NH$_2$, —NH($C_{1-6}$-alkyl), and —N($C_{1-6}$-alkyl)$_2$. In another embodiment, the aryl, $C_{3-8}$ cycloalkyl, heteroaryl, or heterocycloalkyl is unsubstituted.

In one embodiment of formula (I), $R^3$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —NH$_2$, —NH($C_{1-6}$-alkyl), and —N($C_{1-6}$-alkyl)$_2$. In yet another embodiment of formula (I), $R^3$ is phenyl.

In another embodiment of formula (I), $R^3$ is 4-8 membered monocyclic heteroaryl, wherein the heteroaryl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —NH$_2$, —NH($C_{1-6}$-alkyl), and —N($C_{1-6}$-alkyl)$_2$. In another embodiment, the heteroaryl is unsubstituted. In yet another embodiment of formula (I), $R^3$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In yet another embodiment of formula (I), $R^3$ is pyridyl.

In one embodiment of formula (I), $R^3$ is $C_{3-8}$ cycloalkyl, wherein the cycloalkyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —NH$_2$, —NH($C_{1-6}$-alkyl), and —N($C_{1-6}$-alkyl)$_2$. In another embodiment of formula (I), the $C_{3-8}$ cycloalkyl is unsubstituted. In another embodiment of formula (I), the $C_{3-8}$ cycloalkyl is cyclopropane, cyclobutane, cyclopentane, cyclohexane, cycloheptane, or cyclooctane.

In one embodiment of formula (I), $R^3$ is a 3-8 membered heterocycloalkyl, wherein the heterocycloalkyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —NH$_2$, —NH($C_{1-6}$-alkyl), and —N($C_{1-6}$-alkyl)$_2$. In another embodiment, the heterocycloalkyl is unsubstituted. In yet another embodiment of formula (I), the 3-8 membered heterocycloalkyl is oxiranyl, oxetanyl, aziridinyl, azetidinyl, thietanyl, pyrrolidinyl, tetrahydrofuryl, tetrahydrothienyl, imidazolidinyl, pyrazolidinyl, piperidinyl, tetrahydropyranyl, tetrahydrothiopyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl.

In one embodiment of formula (I), $R^3$ is $C_{1-6}$-alkyl, wherein the $C_{1-6}$-alkyl is optionally substituted with one or more substituents independently selected from the group consisting of halo, hydroxy, $C_{1-6}$-alkoxy, —NH$_2$, —NHC$_{1-6}$-alkyl, and —N($C_{1-6}$-alkyl)$_2$. In yet another embodiment, the $C_{1-6}$-alkyl is unsubstituted. In yet another embodiment of formula (I), $R^1$ is —$CH_3$, —$CH_2CH_3$, —$CH_2CH_2CH_3$, —$CH_2CH_2CH_2CH_3$, —$CH(CH_3)_2$, —$C(CH_3)_3$, or —$CH_2CH(CH_3)_2$, which is optionally substituted.

In one embodiment of formula (I), $R^3$ is aryl-$C_{1-6}$-alkyl-, cycloalkyl-$C_{1-6}$-alkyl-, heteroaryl-$C_{1-6}$-alkyl-, or heterocycloalkyl-$C_{1-6}$-alkyl-, wherein the aryl, $C_{3-8}$ cycloalkyl, heteroaryl, or heterocycloalkyl is optionally substituted with one or more substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl)$_2$.

In one embodiment of formula (I), $R^2$ and $R^3$ can be joined together to form a 5-8 membered heterocyclic ring, wherein the ring is a heterocycloalkyl ring, and the ring is optionally substituted with one, two, or three substituents independently selected from the group consisting of halo, $C_{1-6}$-alkyl, $C_{1-6}$-haloalkyl, $C_{1-6}$-hydroxyalkyl, hydroxy, $C_{1-6}$-alkoxy, $C_{1-6}$-haloalkoxy, —$NH_2$, —$NH(C_{1-6}$-alkyl), and $N(C_{1-6}$-alkyl)$_2$. In another embodiment, the heterocycloalkyl ring is unsubstituted.

In one embodiment of formula (I), $R^4$ is hydrogen.

In one embodiment of formula (I), B is $C_{3-8}$ cycloalkyl, wherein the $C_{3-8}$ cycloalkyl is unsubstituted. In another embodiment of formula (I), B is $C_{3-8}$ cycloalkyl, wherein $C_{3-8}$ cycloalkyl is substituted with one, two, or three $R^5$, wherein $R^5$, at each occurrence, is independently halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, or $S(O)_2NR^hR^i$.

In another embodiment of formula (I), B is naphthyl, tetrahydronaphthyl, indenyl, or indanyl, wherein the naphthyl, tetrahydronaphthyl, indenyl, or indanyl is unsubstituted. In yet another embodiment of formula (I), B is naphthyl, tetrahydronaphthyl, indenyl, or indanyl, wherein the naphthyl, tetrahydronaphthyl, indenyl, or indanyl is substituted with one, two, or three $R^5$, wherein $R^5$, at each occurrence, is independently halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, or $S(O)_2NR^hR^i$.

In one embodiment of formula (I), B is phenyl or pyrimidinyl. In another embodiment of formula (I), B is phenyl, wherein the phenyl is unsubstituted. In another embodiment of formula (I), B is phenyl or pyrimidinyl, wherein the phenyl or pyrimidinyl is substituted with one, two, or three $R^5$, and $R^5$, at each occurrence, is independently halo, $C_{1-6}$-alkyl, $C_{1-6}$-haloalkyl, $OR^g$, $NR^hR^i$, cycloalkyl, heterocycloalkyl, heterocycloalkyl-$C_{1-6}$-alkyl-, or heteroaryl, wherein the cycloalkyl, heteroaryl or heterocycloalkyl, alone or as part of another moiety, is optionally substituted with one, two, or three $R^7$; wherein $R^7$, at each occurrence, is independently halo, $C_{1-6}$-alkyl, $C_{1-6}$-haloalkyl, $OR^m$, $C(O)R^m$, $C(O)NR''R^o$, $C(O)OR^m$, $NR''R^o$, $NR''C(O)R^m$, $S(O)_2R^m$, or $S(O)_2NR''R^o$. In yet another embodiment of formula (I), $R^7$ is $C_{1-6}$-alkyl, $C_{1-6}$ haloalkyl, or $C(O)R^m$; and $R^m$ is selected from the group consisting of $C_{1-6}$ alkyl, $C_{1-6}$ haloalkyl, and $C_{3-8}$ cycloalkyl.

In one embodiment of formula (I), B is phenyl, wherein the phenyl is substituted with heterocycloalkyl and optionally one or two $R^5$, wherein $R^5$, at each occurrence, is independently halo, $C_{1-6}$-alkyl, $C_{1-6}$ haloalkyl, or $OR^g$, wherein the heterocycloalkyl is optionally substituted with one, two, or three $R^7$; wherein $R^7$, at each occurrence, is independently halo, $C_{1-6}$-alkyl, $C_{1-6}$-haloalkyl, $OR^m$, $C(O)R^m$, $C(O)NR''R^o$, $C(O)OR^m$, $NR''R^o$, $NR''(O)R^m$, $S(O)_2R^m$, or $S(O)_2NR''R^o$. In yet another embodiment, phenyl is substituted with heterocycloalkyl, and the heterocycloalkyl is azetidinyl, pyrrolidinyl, piperidinyl, morpholinyl, piperazinyl, azepanyl, diazepanyl, or hexahydropyrrolo[1,2-a]pyrazin-2(1H)yl. In another embodiment of formula (I), B is phenyl, wherein the phenyl is substituted with $NR^hR^i$ or $OR^g$, wherein $R^g$ and $R^h$ are independently heterocycloalkyl and $R^i$ is hydrogen. In yet another embodiment, the $R^g$ and $R^h$ heterocycloalkyl is azetidinyl, pyrrolidinyl, piperidinyl, morpholinyl, or piperazinyl, wherein the heterocycloalkyl is optionally substituted with $C_{1-6}$-alkyl or —$N(C_{1-6}$-alkyl)$_2$.

In another embodiment of formula (I), B is

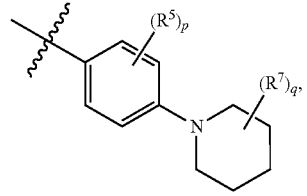

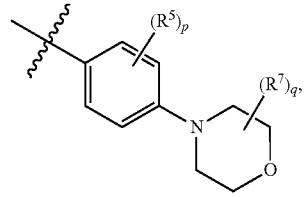

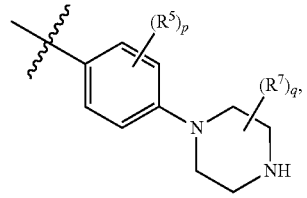

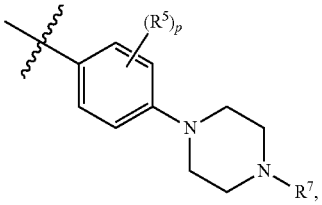

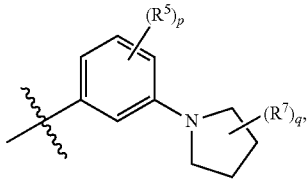

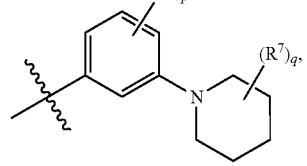

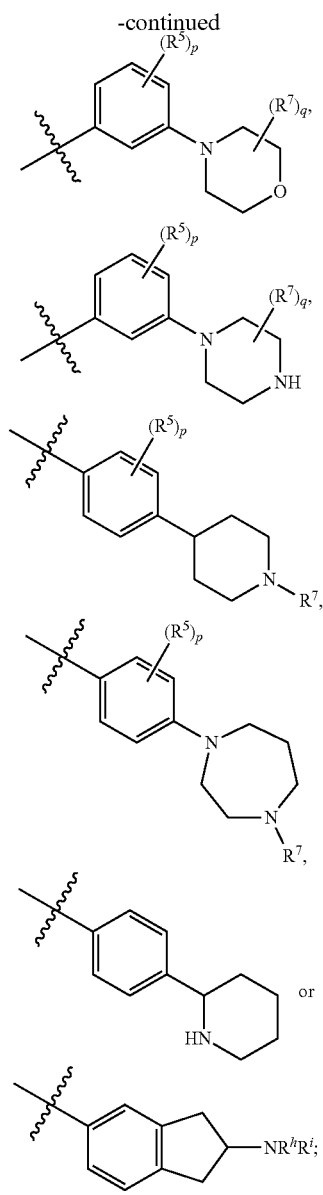

wherein $R^5$ is halo, $C_{1-6}$-alkyl, $C_{1-6}$ haloalkyl, or $OR^g$; p is 0 or 1; $R^7$ is $C_{1-6}$-alkyl, $C_{1-6}$-haloalkyl, $OR^m$, $C(O)R^m$, $C(O)NR''R^o$, $C(O)OR^m$, $NR''R^o$, $NR''C(O)R^m$, $S(O)_2R^m$, or $S(O)_2NR''R^o$; and q is 0 or 1.

In one embodiment of formula (I), B is

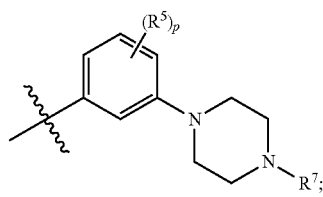

$R^5$ is halo, $C_{1-6}$-alkyl, $C_{1-6}$ haloalkyl, or $OR^g$; $R^7$ is $C_{1-6}$-alkyl; and p is 0 or 1.

In one embodiment of formula (I), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (I), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (I), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^6$, and $R^6$ is halo, $C_{1-6}$-alkyl, $C_{1-6}$-haloalkyl, heterocycloalkyl, $C_{1-4}$-alkyl-heterocycloalkyl-, $OR^j$, $C(O)R^j$, $C(O)OR^j$, $NR^kR^l$, or $S(O)_2R^j$.

In one embodiment of formula (I), B is a 7-11 membered bicyclic heterocyclyl. In another embodiment, B is a 7-11 membered bicyclic heterocycloalkyl or bicyclic heterocycloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo [4,5-c]pyridinyl, or thienothienyl. In one embodiment of formula (I), B is unsubstituted. In another embodiment of formula (I), B is substituted with one, two, or three $R^6$, and $R^6$ is halo, $C_{1-6}$-alkyl, $C_{1-6}$-haloalkyl, $C(O)R^j$, $C(O)OR^j$, $NR^kR^l$, or $S(O)_2R^j$.

In one embodiment of formula (I), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (I), B is 5-oxo-5,6-dihydroimidazo[1,2-a]pyrimido[5,4-e]pyrimidiny-2-yl or 2',3'-dihydro-1'H-spiro[cyclopropane-1,4'-isoquinolin]-7'-yl. In one embodiment of formula (I), B is unsubstituted. In another embodiment of formula (I), B is substituted with one, two, or three $R^6$, and $R^6$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

In one embodiment of formula (I), B is

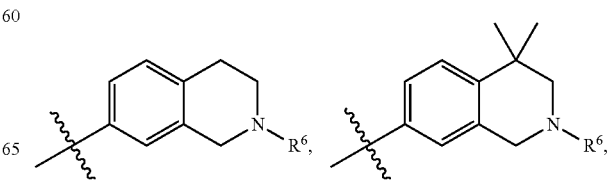

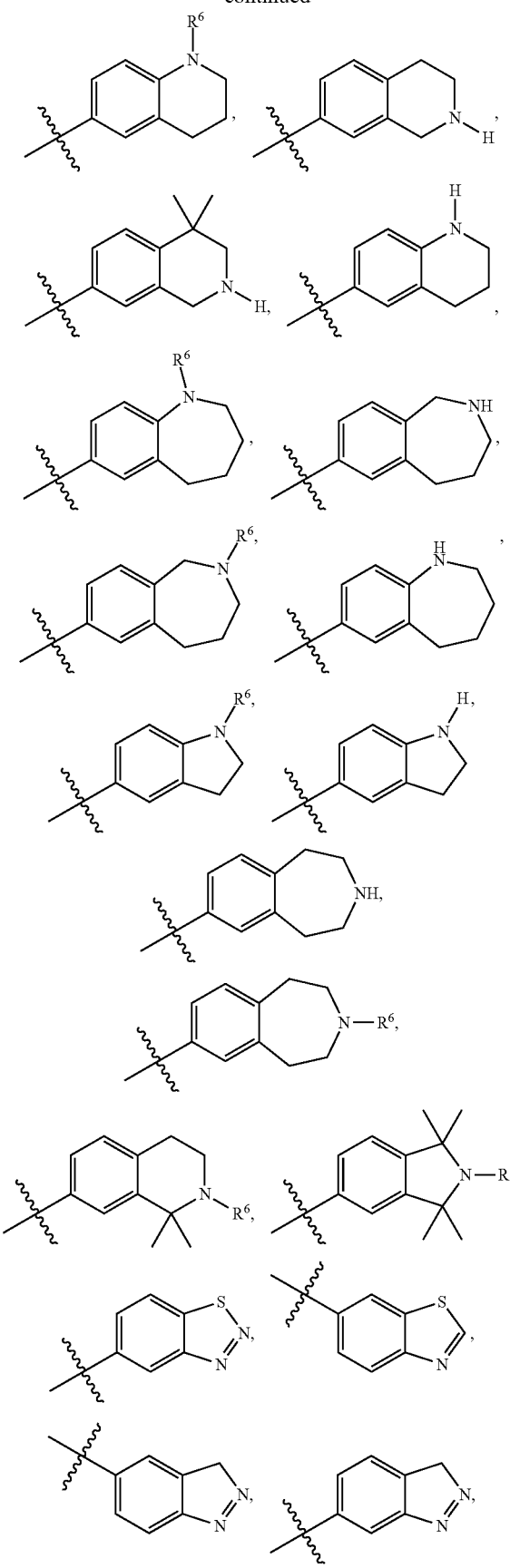

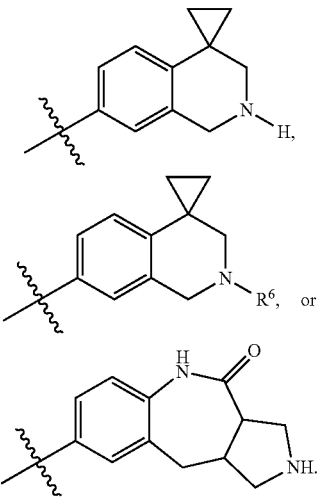

In another embodiment of formula (I), B is

Specific embodiments contemplated as part of the invention include, but are not limited to, compounds of formula (I), for example:

6-(2-chlorophenyl)-2-{[4-(4-methylpiperazin-1-yl)phenyl]amino}pyrido[2,3-d]pyrimidin-5(8H)-one, 6-(2-chlorophenyl)-2-{[4-(4-methylpiperazin-1-yl)phenyl]amino}-8-phenylpyrido[2,3-d]pyrimidin-5(8H)-one, 6-(2-chlorophenyl)-2-{[4-(4-methylpiperazin-1-yl)phenyl]amino}-7-phenylpyrido[2,3-d]pyrimidin-5(8H)-one, 6-(2,6-dichlorophenyl)-2-{[4-(4-methylpiperazin-1-yl)phenyl]amino}-8-phenylpyrido[2,3-d]pyrimidin-5(8H)-one, 6-(2-chlorophenyl)-8-methyl-2-{[4-(4-methylpiperazin-1-yl)phenyl]amino}pyrido[2,3-d]pyrimidin-5(8H)-one, 6-(2,6-dichlorophenyl)-2-{[4-(4-methylpiperazin-1-yl)phenyl]amino}-8,9-dihydropyrimido[4,5-e]indolizin-5(7H)-one, 6-(2,6-dichlorophenyl)-2-{[4-(4-methylpiperazin-1-yl)phenyl]amino}-8-(pyridin-4-yl)pyrido[2,3-d]pyrimidin-5(8H)-one, 6-(2,6-dichlorophenyl)-8-methyl-2-{[4-(4-methylpiperazin-1-yl)phenyl]amino}pyrido[2,3-d]pyrimidin-5(8H)-one, 6-(2,6-dichlorophenyl)-8-(4-fluorophenyl)-2-{[4-(4-methylpiperazin-1-yl)phenyl]amino}pyrido[2,3-d]pyrimidin-5(8H)-one, 8-cyclopropyl-6-(2,6-dichlorophenyl)-2-{[4-(4-methylpiperazin-1-yl)phenyl]amino}pyrido[2,3-d]pyrimidin-5(8H)-one, 6-(2,6-dichlorophenyl)-2-{[4-(4-methylpiperazin-1-yl)phenyl]amino}-8-(2,2,2-trifluoroethyl)pyrido[2,3-d]pyrimidin-5(8H)-one, 6-(2,6-dichlorophenyl)-2-{[4-(4-methylpiperazin-1-yl)phenyl]amino}-8-(pyridin-4-ylmethyl)pyrido[2,3-d]pyrimidin-5(8H)-one, 6-(2,6-dichlorophenyl)-8-[2-(dimethylamino)ethyl]-2-{[4-(4-methylpiperazin-1-yl)phenyl]amino}pyrido[2,3-d]pyrimidin-5(8H)-one, 6-(2,6-dichlorophenyl)-8-methyl-2-[(2'-methyl-2',3'-dihydro-1'H-spiro[cyclopropane-1,4'-isoquinolin]-7'-yl)amino]pyrido[2,3-d]pyrimidin-5(8H)-one, 8-cyclobutyl-6-(2,6-dichlorophenyl)-2-{[4-(4-methylpiperazin-1-yl)phenyl]amino}pyrido[2,3-d]pyrimidin-5(8H)-one, 6-(2,6-dichlorophenyl)-8-(2-hydroxy-2-methylpropyl)-2-{[4-(4-methylpiperazin-1-yl)phenyl]amino}pyrido[2,3-d]pyrimidin-5(8H)-one, 8-cyclopropyl-6-(2,6-dichlorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2,6-dichlorophenyl)-2-{[4-(4-methylpiperazin-1-yl)phenyl]amino}pyrido[2,3-d]pyrimidin-5(8H)-one, 6-(2,6-dichlorophenyl)-8-methyl-2-{[3-methyl-4-(4-methyl-1,4-diazepan-1-yl)phenyl]amino}pyrido[2,3-d]pyrimidin-5(8H)-one, 6-(2,6-dichlorophenyl)-8-methyl-2-[(2,4,4-trimethyl-1,2,3,4-tetrahydroisoquinolin-7-yl)amino]pyrido[2,3-d]pyrimidin-5(8H)-one, 6-(2,6-dichlorophenyl)-2-(2',3'-dihydro-1'H-spiro[cyclopropane-1,4'-isoquinolin]-7'-ylamino)-8-methylpyrido[2,3-d]pyrimidin-5(8H)-one, 6-(2,6-dichlorophenyl)-2-{[2-(dimethylamino)-2,3-dihydro-1H-inden-5-yl]amino}-8-methylpyrido[2,3-d]pyrimidin-5(8H)-one, 8-cyclopropyl-6-(2,6-dichlorophenyl)-2-[(2,4,4-trimethyl-1,2,3,4-tetrahydroisoquinolin-7-yl)amino]pyrido[2,3-d]pyrimidin-5(8H)-one, 8-cyclopropyl-6-(2,6-dichlorophenyl)-2-(2',3'-dihydro-1'H-spiro[cyclopropane-1,4'-isoquinolin]-7'-ylamino)pyrido[2,3-d]pyrimidin-5(8H)-one, 8-cyclopropyl-6-(2,6-dichlorophenyl)-2-{[2-(dimethylamino)-2,3-dihydro-1H-inden-5-yl]amino}pyrido[2,3-d]pyrimidin-5(8H)-one, 6-(2,6-dichlorophenyl)-2-{[4-(4-methylpiperazin-1-yl)phenyl]amino}-8-(propan-2-yl)pyrido[2,3-d]pyrimidin-5(8H)-one, 6-(2,6-dichlorophenyl)-2-{[4-(4-methylpiperazin-1-yl)phenyl]amino}-8-(oxetan-3-yl)pyrido[2,3-d]pyrimidin-5(8H)-one, 8-tert-butyl-6-(2,6-dichlorophenyl)-2-{[4-(4-methylpiperazin-1-yl)phenyl]amino}pyrido[2,3-d]pyrimidin-5(8H)-one, 6-(2,6-dichlorophenyl)-8-(4-methoxybenzyl)-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2,6-dichlorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2,6-dichlorophenyl)-8-ethyl-2-{[4-(4-methylpiperazin-1-yl)phenyl]amino}pyrido[2,3-d]pyrimidin-5(8H)-one, 6-(2,6-dichlorophenyl)-8-ethyl-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2-chloro-6-fluorophenyl)-8-methyl-2-{[4-(4-methylpiperazin-1-yl)phenyl]amino}pyrido[2,3-d]pyrimidin-5(8H)-one, 6-(2-chloro-6-fluorophenyl)-8-methyl-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2-chloro-6-fluorophenyl)-8-(4-methoxybenzyl)-2-{[4-(4-methylpiperazin-1-yl)phenyl]amino}pyrido[2,3-d]pyrimidin-5(8H)-one, 6-(2-chloro-6-fluorophenyl)-8-(4-methoxybenzyl)-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2-chloro-6-fluorophenyl)-8-cyclopropyl-2-{[4-(4-methylpiperazin-1-yl)phenyl]amino}pyrido[2,3-d]pyrimidin-5(8H)-one, 6-(2-chloro-6-fluorophenyl)-8-cyclopropyl-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2-chloro-6-fluorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2-chloro-6-fluorophenyl)-2-{[4-(4-methylpiperazin-1-yl)phenyl]amino}pyrido[2,3-d]pyrimidin-5(8H)-one, 6-(2,6-dichlorophenyl)-2-{[2-(dimethylamino)-2,3-dihydro-1H-inden-5-yl]amino}pyrido[2,3-d]pyrimidin-5(8H)-one, 6-(2,6-dichlorophenyl)-2-[(2,4,4-trimethyl-1,2,3,4-tetrahydroisoquinolin-7-yl)amino]pyrido[2,3-d]pyrimidin-5(8H)-one, 6-(2,6-dichlorophenyl)-2-(2',3'-dihydro-1'H-spiro[cyclopropane-1,4'-isoquinolin]-7'-ylamino)pyrido[2,3-d]pyrimidin-5(8H)-one, 6-(2,6-dichlorophenyl)-2-({4-[4-(dimethylamino)piperidin-1-yl]phenyl}amino)-8-methylpyrido[2,3-d]pyrimidin-5(8H)-one, 6-(2,6-dichlorophenyl)-8-methyl-2-(1,2,3,4-tetrahydroisoquinolin-6-ylamino)pyrido[2,3-d]pyrimidin-5(8H)-one, 6-(2,6-dichlorophenyl)-2-[(4,4-dimethyl-1,2,3,4-tetrahydroisoquinolin-7-yl)amino]-8-methylpyrido[2,3-d]pyrimidin-5(8H)-one, 6-(2,6-dichlorophenyl)-8-methyl-2-{[4-(morpholin-4-yl)phenyl]amino}pyrido[2,3-d]pyrimidin-5(8H)-one, 6-(2,6-dichlorophenyl)-2-(2,3-dihydro-1H-isoindol-5-ylamino)-8-methylpyrido[2,3-d]pyrimidin-5(8H)-one, 6-(2,6-dichlorophenyl)-8-methyl-2-{[4-(1-methylpiperidin-4-yl)phenyl]amino-}pyrido[2,3-d]pyrimidin-5(8H)-one, 6-(2,6-dichlorophenyl)-8-methyl-2-(1,2,3,4-tetrahydroisoquinolin-7-ylamino)pyrido[2,3-d]pyrimidin-5(8H)-one, 6-(2,6-dichlorophenyl)-8-methyl-2-[(2-methyl-1,2,3,4-tetrahydroisoquinolin-7-yl)amino]pyrido[2,3-d]pyrimidin-5(8H)-one, 6-(2,6-dichlorophenyl)-8-methyl-2-[(2-methyl-2,3-dihydro-1H-isoindol-5-yl)amino]pyrido[2,3-d]pyrimidin-5(8H)-one, 6-(2,6-dichlorophenyl)-8-methyl-2-[(2-methyl-1,2,3,4-tetrahydroisoquinolin-6-yl)amino]pyrido[2,3-d]pyrimidin-5(8H)-one, 5-{[6-(2,6-dichlorophenyl)-8-methyl-5-oxo-5,8-dihydropyrido[2,3-d]pyrimidin-2-yl]amino}-1H-isoindole-1,3(2H)-dione, 6-(2,6-dichlorophenyl)-8-methyl-2-{[2-(4-methylpiperazin-1-yl)-2,3-dihydro-1H-inden-5-yl]amino}pyrido[2,3-d]pyrimidin-5(8H)-one, 6-(2,6-dichlorophenyl)-8-methyl-2-(4,5,6,7-tetrahydrothieno[3,2-c]pyridin-2-ylamino)pyrido[2,3-d]pyrimidin-5(8H)-one, 6-(2,6-dichlorophenyl)-8-methyl-2-{[2-(4-methylpiperazin-1-yl)pyrimidin-5-yl]amino}pyrido[2,3-d]pyrimidin-5(8H)-one, 6-(2,6-dichlorophenyl)-8-methyl-2-[(1,1,2-trimethyl-2,3-dihydro-1H-isoindol-5-yl)amino]pyrido[2,3-d]pyrimidin-5(8H)-one, 6-(2,6-dichlorophenyl)-8-methyl-2-({4-[(1-methylpiperidin-4-yl)amino]phenyl}amino)pyrido[2,3-d]pyrimidin-5(8H)-one, 6-(2,6-dichlorophenyl)-2-({2-[4-(dimethylamino)piperidin-1-yl]pyrimidin-5-yl}amino)-8-methylpyrido[2,3-d]pyrimidin-5(8H)-one, 6-(2,6-dichlorophenyl)-8-methyl-2-({4-[(3R)-pyrrolidin-3-ylamino]phenyl}amino)pyrido[2,3-d]pyrimidin-5(8H)-one, 6-(2,6-dichlorophenyl)-8-methyl-2-({4-[(3S)-pyrrolidin-3-ylamino]phenyl}amino)pyrido[2,3-d]pyrimidin-5(8H)-one, 6-(2,6-dichlorophenyl)-2-[(1,1-dimethyl-2,3-dihydro-1H-isoindol-5-yl)amino]-8-methylpyrido[2,3-d]pyrimidin-5(8H)-one, 6-(2,6-dichlorophenyl)-8-methyl-2-{[4-(piperidin-4-ylamino)phenyl]amino}pyrido[2,3-d]pyrimidin-5(8H)-one, 6-(2,6-dichlorophenyl)-8-methyl-2-({4-[(1-methylpyrrolidin-3-yl)amino]phenyl}amino)pyrido[2,3-d]pyrimidin-5(8H)-one, 6-(2,6-dichlorophenyl)-8-methyl-2-({4-[(1-methylpiperidin-4-yl)oxy]phenyl}amino)pyrido[2,3-d]pyrimidin-5(8H)-one, 6-(2-chloro-6-fluorophenyl)-8-methyl-2-({4-[(1-methylpiperidin-4-yl)amino]phenyl}amino)pyrido[2,3-d]pyrimidin-5(8H)-one, 6-(2-chloro-6-fluorophenyl)-8-methyl-2-[(1,1,2-trimethyl-2,3-dihydro-1H-isoindol-5-yl)amino]pyrido[2,3-d]pyrimidin-5(8H)-one, methyl 5-{[6-(2,6-dichlorophenyl)-8-methyl-5-oxo-5,8-dihydropyrido[2,3-d]pyrimidin-2-yl]amino}-2-(4-methylpiperazin-1-yl)benzoate, 6-(2,6-dichlorophenyl)-2-({2-[4-(dimethylamino)piperidin-1-yl]-2,3-dihydro-1H-inden-5-yl}amino)-8-methylpyrido[2,3-d]pyrimidin-5(8H)-one, 6-(2-chloro-6-fluorophenyl)-8-methyl-2-{[4-(piperidin-4-ylamino)phenyl]amino}pyrido[2,3-d]pyrimidin-5(8H)-one, 6-(2-chloro-6-fluorophenyl)-8-methyl-2-(1,2,3,4-tetrahydroisoquinolin-7-ylamino)pyrido[2,3-d]pyrimidin-5(8H)-one, 6-(2-chloro-6-fluorophenyl)-8-methyl-2-(1,2,3,4-tetrahydroisoquinolin-6-ylamino)pyrido[2,3-d]pyrimidin-5(8H)-one, 6-(2,6-dichlorophenyl)-2-[(4-{[trans-4-(dimethylamino)cyclohexyl]amino}phenyl)amino]-8-methylpyrido[2,3-d]pyrimidin-5(8H)-one, 6-(2,6-dichlorophenyl)-2-[(4-{[cis-4-(dimethylamino)cyclohexyl]amino}phenyl)amino]-8-methylpyrido[2,3-d]pyrimidin-5(8H)-one, 6-(2,6-dichlorophenyl)-2-[(4-{4-[3-(dimethylamino)propyl]piperazin-1-yl}phenyl)amino]-8-methylpyrido[2,3-d]pyrimidin-5(8H)-one, and 6-(2,6-dichlorophenyl)-2-[(4-{4-[2-(dimethylamino)ethyl]piperazin-1-yl}phenyl)amino]-8-methylpyrido[2,3-d]pyrimidin-5(8H)-one.

Embodiments of Formula (II)

In one embodiment, the present invention is directed, in part, to a class of compounds having a structure of formula (II),

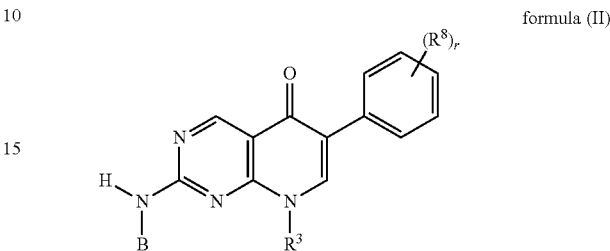

formula (II)

wherein $R^3$ and B are as described in formula (I), $R^8$ is $C_{1-6}$-alkyl, $C_{1-6}$-haloalkyl, $C_{2-6}$-alkenyl, heterocycloalkyl, aryl, heteroaryl, halo, CN, $NO_2$, $—OR^d$, $—C(O)R^d$, $—C(O)OR^d$, $—OC(O)R^d$, $—SR^d$, $—S(O)R^d$, $—SO_2R^d$, $—NR^eR^f$, $—NHC(O)R^e$, $—NHC(O)NHR^e$, $—NHC(O)OR^e$, $—NHSO_2R^d$, $—C(O)NHR^e$, or $—SO_2NHNR^e$, and r is 0, 1, 2, or 3.

In one embodiment of formula (II), $R^8$ is $C_{1-6}$-alkyl, $C_{1-6}$-haloalkyl, heterocycloalkyl, halo, CN, or $NO_2$ and r is 1 or 2. In another embodiment of formula (II), $R^8$ is halo and r is 1 or 2.

In one embodiment, the present invention is directed, in part, to a class of compounds having a structure of formula (IIA) or (IIB):

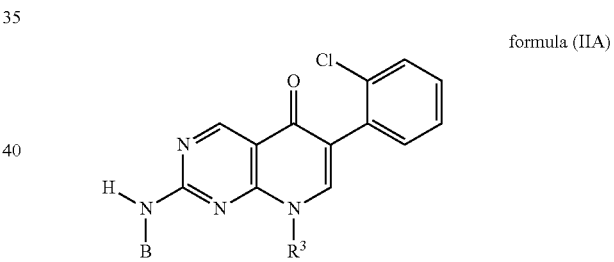

formula (IIA)

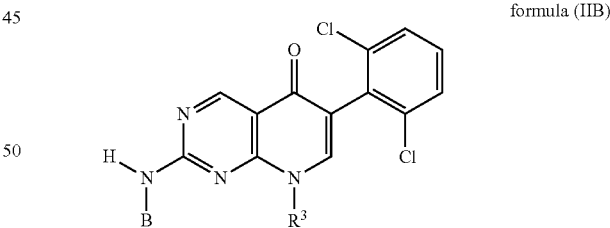

formula (IIB)

In one embodiment of formula (II), (IIA), or (IIB), $R^3$ is hydrogen.

In one embodiment of formula (II), (IIA), or (IIB), $R^3$ is aryl, $C_{3-8}$ cycloalkyl, heteroaryl, or heterocycloalkyl, wherein the aryl, $C_{3-8}$ cycloalkyl, heteroaryl, or heterocycloalkyl is optionally substituted with one or more substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $—NH_2$, $—NH(C_{1-6}$-alkyl), and $—N(C_{1-6}$-alkyl)$_2$. In another embodiment, the aryl, $C_{3-8}$ cycloalkyl, heteroaryl, or heterocycloalkyl is unsubstituted.

In one embodiment of formula (II), (IIA), or (IIB), $R^3$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$. In yet another embodiment of formula (I), $R^3$ is phenyl.

In another embodiment of formula (II), (IIA), or (IIB), $R^3$ is 4-8 membered monocyclic heteroaryl, wherein the heteroaryl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$. In another embodiment, the heteroaryl is unsubstituted. In yet another embodiment of formula (II), (IIA), or (IIB), $R^3$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In yet another embodiment of formula (II), (IIA), or (IIB), $R^3$ is pyridyl.

In one embodiment of formula (II), (IIA), or (IIB), $R^3$ is $C_{3-8}$ cycloalkyl, wherein the cycloalkyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$. In another embodiment of formula (II), (IIA), or (IIB), the $C_{3-8}$ cycloalkyl is unsubstituted. In another embodiment of formula (II), (IIA), or (IIB), the $C_{3-8}$ cycloalkyl is cyclopropane, cyclobutane, cyclopentane, cyclohexane, cycloheptane, or cyclooctane.

In one embodiment of formula (II), (IIA), or (IIB), $R^3$ is a 3-8 membered heterocycloalkyl, wherein the heterocycloalkyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$. In another embodiment, the heterocycloalkyl is unsubstituted. In yet another embodiment of formula (II), (IIA), or (IIB), the 3-8 membered heterocycloalkyl is oxiranyl, oxetanyl, aziridinyl, azetidinyl, thietanyl, pyrrolidinyl, tetrahydrofuryl, tetrahydrothienyl, imidazolidinyl, pyrazolidinyl, piperidinyl, tetrahydropyranyl, tetrahydrothiopyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl.

In one embodiment of formula (II), (IIA), or (IIB), $R^3$ is $C_{1-6}$-alkyl, wherein the $C_{1-6}$-alkyl is optionally substituted with one or more substituents independently selected from the group consisting of halo, hydroxy, $C_{1-6}$-alkoxy, —$NH_2$, —$NHC_{1-6}$-alkyl, and —$N(C_{1-6}$-alkyl$)_2$. In yet another embodiment, the $C_{1-6}$-alkyl is unsubstituted. In yet another embodiment of formula (I), $R^1$ is —$CH_3$, —$CH_2CH_3$, —$CH_2CH_2CH_3$, —$CH_2CH_2CH_2CH_3$, —$CH(CH_3)_2$, —$C(CH_3)_3$, or —$CH_2CH(CH_3)_2$, which is optionally substituted.

In one embodiment of formula (II), (IIA), or (IIB), $R^3$ is aryl-$C_{1-6}$-alkyl-, cycloalkyl-$C_{1-6}$-alkyl-, heteroaryl-$C_{1-6}$-alkyl-, or heterocycloalkyl-$C_{1-6}$-alkyl-, wherein the aryl, $C_{3-8}$ cycloalkyl, heteroaryl, or heterocycloalkyl is optionally substituted with one or more substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$.

In one embodiment of formula (II), (IIA), or (IIB), $R^2$ and $R^3$ can be joined together to form a 5-8 membered heterocyclic ring, wherein the ring is a heterocycloalkyl ring, and the ring is optionally substituted with one, two, or three substituents independently selected from the group consisting of halo, $C_{1-6}$-alkyl, $C_{1-6}$-haloalkyl, $C_{1-6}$-hydroxyalkyl, hydroxy, $C_{1-6}$-alkoxy, $C_{1-6}$-haloalkoxy, —$NH_2$, —$NH(C_{1-6}$-alkyl), and $N(C_{1-6}$-alkyl$)_2$. In another embodiment, the heterocycloalkyl ring is unsubstituted.

In one embodiment of formula (II), (IIA), or (IIB), B is $C_{3-8}$ cycloalkyl, wherein the $C_{3-8}$ cycloalkyl is unsubstituted. In another embodiment of formula (II), (IIA), or (IIB), B is $C_{3-8}$ cycloalkyl, wherein $C_{3-8}$ cycloalkyl is substituted with one, two, or three $R^5$, wherein $R^5$, at each occurrence, is independently halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, or $S(O)_2NR^hR^i$.

In another embodiment of formula (II), (IIA), or (IIB), B is naphthyl, tetrahydronaphthyl, indenyl, or indanyl, wherein the naphthyl, tetrahydronaphthyl, indenyl, or indanyl is unsubstituted. In yet another embodiment of formula (II), (IIA), or (IIB), B is naphthyl, tetrahydronaphthyl, indenyl, or indanyl, wherein the naphthyl, tetrahydronaphthyl, indenyl, or indanyl is substituted with one, two, or three $R^5$, wherein $R^5$, at each occurrence, is independently halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, or $S(O)_2NR^hR^i$.

In one embodiment of formula (II), (IIA), or (IIB), B is phenyl or pyrimidinyl. In another embodiment of formula (II), (IIA), or (IIB), B is phenyl, wherein the phenyl is unsubstituted. In another embodiment of formula (II), (IIA), or (IIB), B is phenyl or pyrimidinyl, wherein the phenyl or pyrimidinyl is substituted with one, two, or three $R^5$, and $R^5$, at each occurrence, is independently halo, $C_{1-6}$-alkyl, $C_{1-6}$ haloalkyl, $OR^g$, $NR^hR^i$, cycloalkyl, heterocycloalkyl, heterocycloalkyl-$C_{1-6}$-alkyl-, or heteroaryl, wherein the cycloalkyl, heteroaryl or heterocycloalkyl, alone or as part of another moiety, is optionally substituted with one, two, or three $R^7$; wherein $R^7$, at each occurrence, is independently halo, $C_{1-6}$-alkyl, $C_{1-6}$-haloalkyl, $OR^m$, $C(O)R^m$, $C(O)NR''R^o$, $C(O)OR^m$, $NR''R^o$, $NR''C(O)R^m$, $S(O)_2R^m$, or $S(O)_2NR''R^o$. In yet another embodiment of formula (II), (IIA), or (IIB), $R^7$ is $C_{1-6}$-alkyl, $C_{1-6}$ haloalkyl, or $C(O)R^m$; and $R^m$ is selected from the group consisting of $C_{1-6}$ alkyl, $C_{1-6}$ haloalkyl, and $C_{3-8}$ cycloalkyl.

In one embodiment of formula (II), (IIA), or (IIB), B is phenyl, wherein the phenyl is substituted with heterocycloalkyl and optionally one or two $R^5$, wherein $R^5$, at each occurrence, is independently halo, $C_{1-6}$-alkyl, $C_{1-6}$ haloalkyl, or $OR^g$, wherein the heterocycloalkyl is optionally substituted with one, two, or three $R^7$; wherein $R^7$, at each occurrence, is independently halo, $C_{1-6}$-alkyl, $C_{1-6}$-haloalkyl, $OR^m$, $C(O)R^m$, $C(O)NR''R^o$, $C(O)OR^m$, $NR''R^o$, $NR''(O)R^m$, $S(O)_2R^m$, or $S(O)_2NR''R^o$. In yet another embodiment, phenyl is substituted with heterocycloalkyl, and the heterocycloalkyl is azetidinyl, pyrrolidinyl, piperidinyl, morpholinyl, piperazinyl, azepanyl, diazepanyl, or hexahydropyrrolo[1,2-a]pyrazin-2(1H)yl. In another embodiment of formula (II), (IIA), or (IIB), B is phenyl, wherein the phenyl is substituted with $NR^hR^i$ or $OR^g$, wherein $R^g$ and $R^h$ are independently heterocycloalkyl and $R^i$ is hydrogen. In yet another embodiment, the $R^g$ and $R^h$ heterocycloalkyl is azetidinyl, pyrrolidinyl, piperidinyl, morpholinyl, or piperazinyl, wherein the heterocycloalkyl is optionally substituted with $C_{1-6}$-alkyl or —$N(C_{1-6}$-alkyl$)_2$.

In another embodiment of formula (II), (IIA), or (IIB), B is

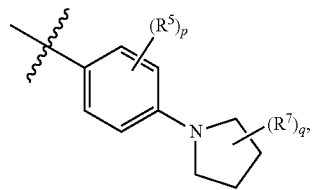

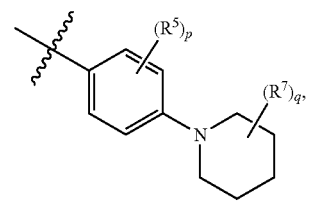

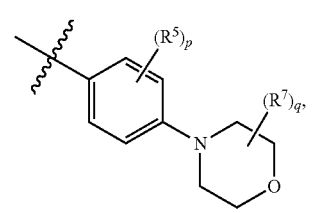

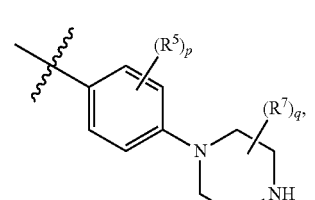

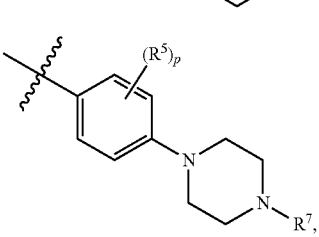

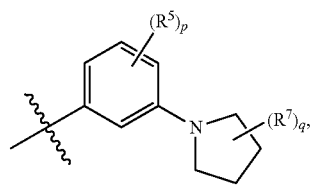

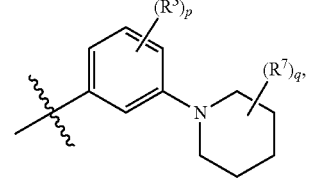

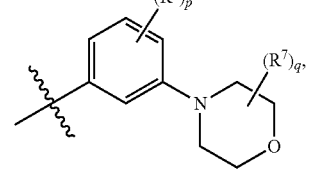

-continued

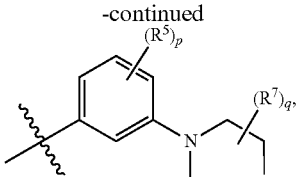

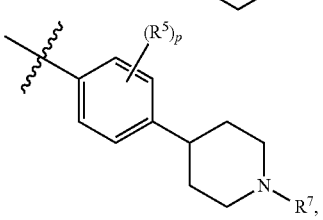

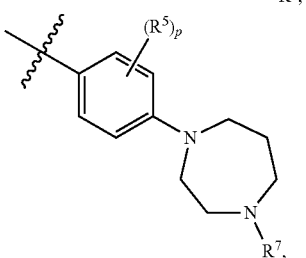

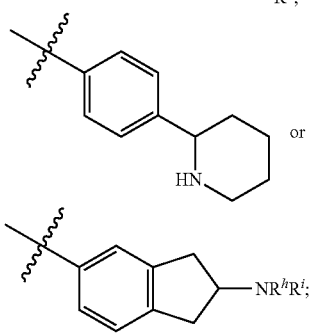

wherein $R^5$ is halo, $C_{1-6}$-alkyl, $C_{1-6}$ haloalkyl, or $OR^g$; p is 0 or 1; $R^7$ is $C_{1-6}$-alkyl, $C_{1-6}$-haloalkyl, $OR^m$, $C(O)R^m$, $C(O)NR''R^o$, $C(O)OR^m$, $NR''R^o$, $NR''C(O)R^m$, $S(O)_2R^m$, or $S(O)_2NR''R^o$; and q is 0 or 1.

In one embodiment of formula (II), (IIA), or (IIB), B is

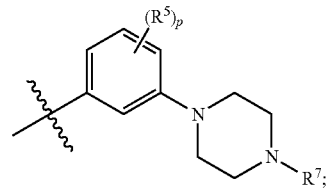

$R^5$ is halo, $C_{1-6}$-alkyl, $C_{1-6}$ haloalkyl, or $OR^g$; $R^7$ is $C_{1-6}$-alkyl; and p is 0 or 1.

In one embodiment of formula (II), (IIA), or (IIB), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (II), (IIA), or (IIB), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (II), (IIA), or (IIB), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^6$, and $R^6$ is halo, $C_{1-6}$-alkyl, $C_{1-6}$-haloalkyl, heterocycloalkyl, $C_{1-4}$-alkyl-heterocycloalkyl-, $OR^j$, $C(O)R^j$, $C(O)OR^j$, $NR^kR^l$, or $S(O)_2R^j$.

In one embodiment of formula (II), (IIA), or (IIB), B is a 7-11 membered bicyclic heterocyclyl. In another embodiment, B is a 7-11 membered bicyclic heterocycloalkyl or bicyclic heterocyloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo [4,5-c] pyridinyl, or thienothienyl. In one embodiment of formula (II), (IIA), or (IIB), B is unsubstituted. In another embodiment of formula (II), (IIA), or (IIB), B is substituted with one, two, or three $R^6$, and $R^6$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

In one embodiment of formula (II), (IIA), or (IIB), B is 10-15 membered tricyclic heterocyclyl. In another embodiment, B is a 10-15 membered tricyclic heterocycloalkyl or tricyclic heterocyloalkenyl. In another embodiment, B is a 10-15 membered tricyclic heteroaryl. In one embodiment of formula (II), (IIA), or (IIB), B is 5-oxo-5,6-dihydroimidazo [1,2-a]pyrimido[5,4-e]pyrimidiny-2-yl or 2',3'-dihydro-1'H-spiro[cyclopropane-1,4'-isoquinolin]-7'-yl. In one embodiment of formula (II), (IIA), or (IIB), B is unsubstituted. In another embodiment of formula (II), (IIA), or (IIB), B is substituted with one, two, or three $R^6$, and $R^6$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

In one embodiment of formula (II), (IIA), or (IIB), B is

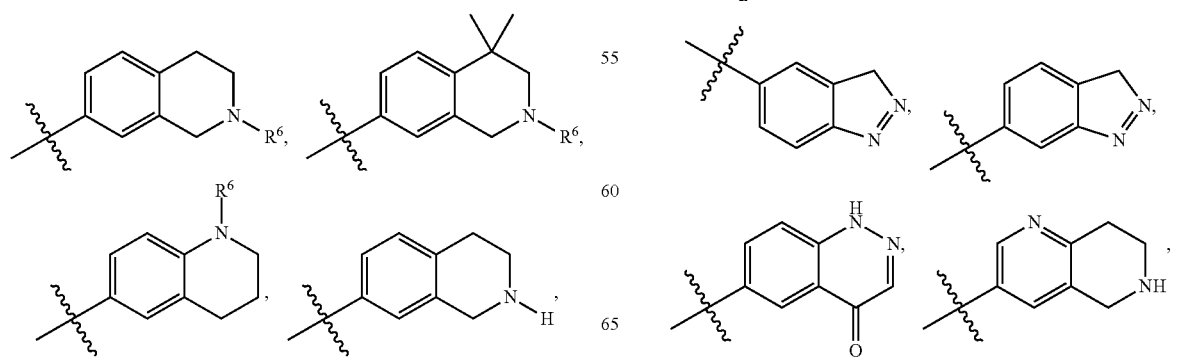

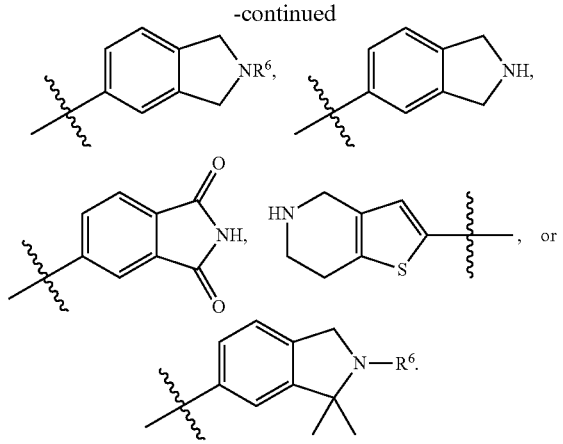

In another embodiment of formula (II), (IIA), or (IIB), B is

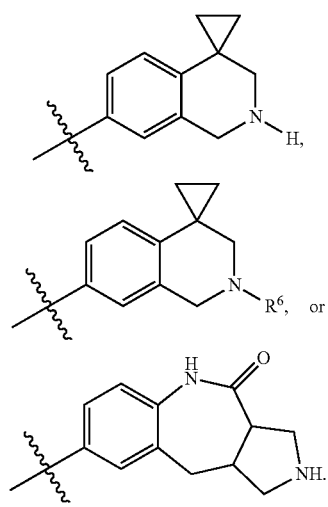

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Tautomeric forms are intended to be encompassed by the scope of this invention, even though only one tautomeric form may be depicted.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like. Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

Schemes

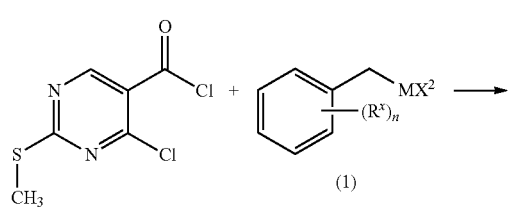

(1)

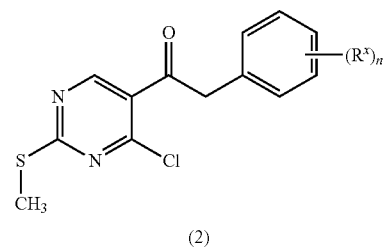

(2)

As shown in Scheme 1,4-chloro-2-(methylthio)pyrimidine-5-carbonyl chloride can be reacted with compounds of formula (I) wherein $R^x$ is as described herein for substituents on $R^1$; n is 0-5; and $MX^2$ is MgCl or ZnCl; to provide compounds of formula (2). When $MX^2$ is MgCl, the reaction is typically performed at low temperature in a solvent such as but not limited to tetrahydrofuran. When $MX^2$ is ZnCl, a mixture of CuCN:2LiCl and compounds of formula (1) can be reacted with 4-chloro-2-(methylthio)pyrimidine-5-carbonyl chloride to provide compounds of formula (2). The addition is typically performed at low temperature in a solvent such as but not limited to tetrahydrofuran.

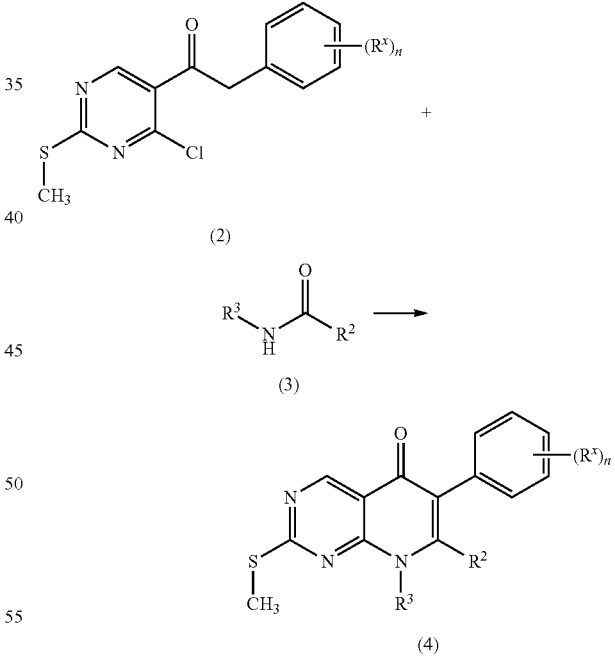

Compounds of formula (2), in the presence of a catalyst such as but not limited to tris(dibenzylideneacetone)dipalladium(0), a ligand such as but not limited to Xantphos, and a base such as but not limited to cesium carbonate, can be reacted with an amide of formula (3), wherein $R^2$ and $R^3$ are as described herein, to provide compounds of formula (4). The reaction is typically performed at an elevated temperature in a solvent such as but not limited to dioxane.

Scheme 3

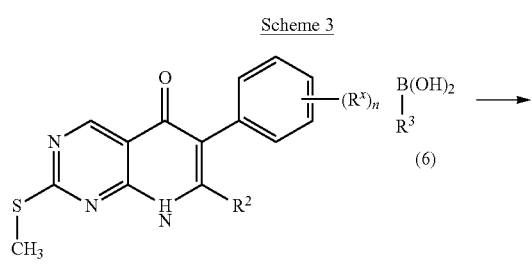

Compounds of formula (5), which can be prepared as described in Scheme 2 wherein $R^3$ is hydrogen, and $R^2$, $R^x$ and n are as described in Scheme 1 and 2; can be reacted with a boronic acid of formula (6) wherein $R^3$ is a substituent as described herein, copper(II) acetate, and a base such as but not limited to triethylamine, to provide compounds of formula (7). The reaction is typically performed at ambient temperature in a solvent such as but not limited to dichloromethane.

Scheme 4

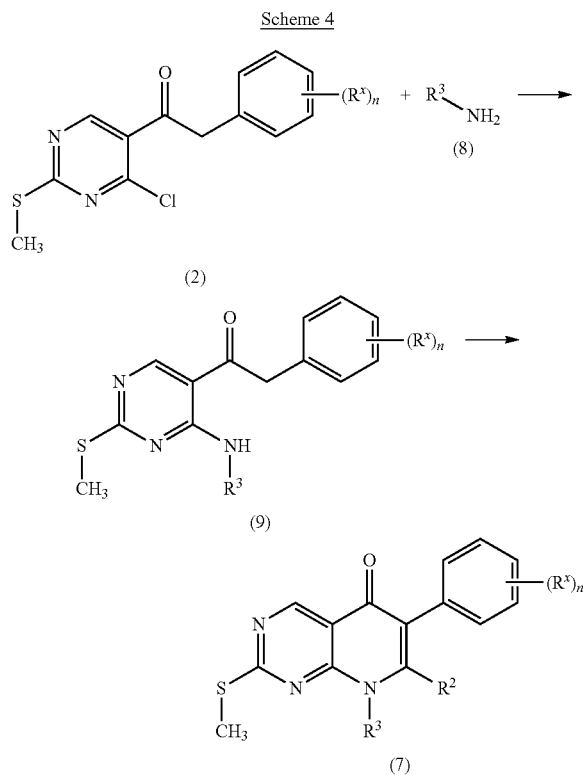

Compounds of formula (2), which can be prepared as described in Scheme 1, can be reacted with an amine of formula (8) wherein $R^3$ is as described herein, to provide compounds of formula (9). The reaction is typically performed at elevated temperature in a solvent such as but not limited to isopropanol. Compounds of formula (7) wherein $R^2$ is H, can be prepared by reacting N,N-dimethylformide dimethylacetal with compounds of formula (9). The reaction is typically performed at an elevated temperature and may be heated in a microwave reactor.

Scheme 5

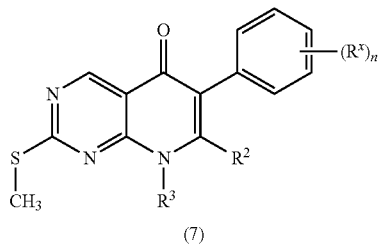

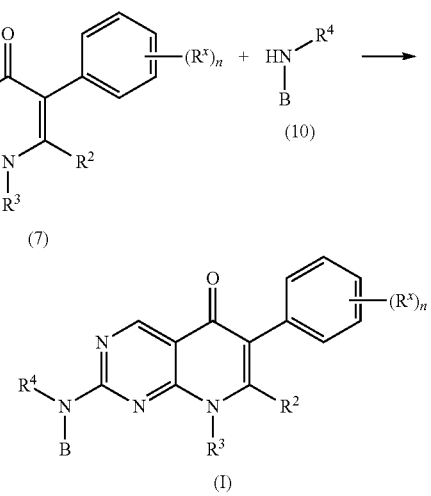

As shown in Scheme 5, compounds of formula (7) can be reacted with amines of formula (10), wherein $R^4$ and B are as described herein, to provide compounds of formula (I). The reaction is typically performed at an elevated temperature. Alternatively, compounds of formula (7) can be treated with m-CPBA at ambient temperature, followed by reaction with compounds of formula (10), in a solvent such as, but not limited to, acetonitrile, and an acid such as, but not limited to, trifluoroacetic acid at an elevated temperature to provide compounds of formula (I).

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, over-expression or disregulation of kinases in a mammal. In particular, compounds of this invention are expected to have utility in treatment of diseases or conditions during which protein kinases such as any or all wee-1 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In one group of embodiments, diseases and conditions of humans or other animals that can be treated with inhibitors of kinases, include, but are not limited to, tumors that are deficient in the p53 protein. The p53 protein is a tumor suppressor protein that is encoded in humans by the TP53 gene. The p53 protein regulates the cell cycle and therefore functions as a tumor suppressor that is involved in preventing cancer Inhibition of Wee1 kinases sensitizes tumor cells to DNA damage and/or cell cycle perturbation, especially tumors that have lost their $G_1$-phase checkpoint due to a deficiency in the p53 protein.

A discussion of the loss of expression of Wee1 and how it relates to deficiency in the p53 protein can be found in Annual Review of Biochemistry, 2004, 73:39-85.

Involvement of mutations in the p53 gene and human tumor types can be found in Nature, 1989, 342:705-708.

A discussion of Wee1 kinase and p53 deficient tumor cells can be found in Molecular Cancer Therapy, 2009, 8:11.

A discussion of p53 and Wee1 kinases and anti-cancer therapies can be found in BMC Cancer 2006, 6:292.

A discussion of Wee1 kinase and p53 deficient tumor cells can be found in Current Clinical Pharmacology, 2010, 5:186-191.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi- Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA®(letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE°, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN° (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®; P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT®(AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Example 1

6-(2-chlorophenyl)-2-{[4-(4-methylpiperazin-1-yl) phenyl]amino}pyrido[2,3-d]pyrimidin-5(8H)-one Example 1A 1-(4-chloro-2-(methylthio)pyrimidin-5-yl)-2-(2-chlorophenyl)ethanone An oven dried flask, equipped with stir bar and septa, was charged with 4-chloro-2-(methylthio)pyrimidine-5-carbonyl chloride (Aaron Chemistry, 1338 mg, 6 mmol). The flask was capped with septa, evacuated and backfilled with nitrogen (three times). The solid was dissolved in tetrahydrofuran (24.0 mL), cooled to −78° C. and kept under nitrogen. (2-Chlorobenzyl)magnesium chloride (14.40 mL, 7.20 mmol) was then slowly added. After the addition was completed, the dry ice/acetone bath was removed and the mixture was stirred at ambient temperature for 3 hours. The mixture was quenched with aqueous 1 M HCl (50 mL), extracted with ethyl acetate (3×80 mL) and the combined extracts were washed with brine, dried over magnesium sulfate (MgSO$_4$), filtered and concentrated. The crude product obtained was purified by flash chromatography (Isco®, Redi-Sep® column, 0-30% ethyl acetate/hexane, linear gradient) to afford the title compound. $^1$H NMR (300 MHz, CDCl$_3$) δ ppm 8.72 (s, 1H), 7.47-7.36 (m, 1H), 7.36-7.21 (m, 3H), 4.41 (s, 2H), 2.61 (s, 3H); MS (ESI) m/z 313 (M+H)$^+$.

Example 1B 6-(2-chlorophenyl)-2-(methylthio)pyrido[2,3-d]pyrimidin-5(8H)-one

A 2 dram vial, equipped with stir bar and septa, was charged with tris(dibenzylideneacetone)dipalladium(0) (27.8 mg, 0.030 mmol), Xantphos (4,5-bis(diphenylphosphino)-9,9-dimethylxanthene, 44.0 mg, 0.076 mmol), Example 1A (238 mg, 0.760 mmol) and cesium carbonate (743 mg, 2.28 mmol). The mixture was evacuated and backfilled with nitrogen (three times). Dioxane (1.9 mL, 0.4 M) and formamide (60.6 µl, 1.520 mmol) were added and the mixture was evacuated and backfilled with argon (three times) then stirred at 100° C. for 3 hours. After cooling to ambient temperature, aqueous 1 M HCl (40 mL) was added, the mixture was poured into a separatory funnel, and the mixture was extracted with ethyl acetate (3×40 mL). The combined organic extracts were washed with brine, dried over magnesium sulfate, filtered and concentrated. Purification by flash chromatography (Isco®, Redi-Sep® column, 0-85% ethyl acetate/hexane, linear gradient) afforded the title compound. $^1$H NMR (300 MHz, dimethylsulfoxide-d$_6$) δ ppm 12.56 (d, J=5.0, 1H), 9.17 (s, 1H), 7.95 (d, J=5.6, 1H), 7.56-7.48 (m, 1H), 7.45-7.34 (m, 3H), 2.61 (s, 3H); MS (ESI) m/z 304 (M+H)$^+$.

Example 1C 6-(2-chlorophenyl)-2-{[4-(4-methylpiperazin-1-yl)phenyl]amino}pyrido[2,3-d]pyrimidin-5(8H)-one A 5 mL microwave vessel was charged with Example 1B (24 mg, 0.079 mmol) and 4-(4-methylpiperazin-1-yl)aniline (76 mg, 0.395 mmol). The vessel was capped then the solid mixture was heated at 150° C. for 16 hours (LC/MS analysis showed about 40% conversion). After cooling to ambient temperature, the crude material was dissolved in 1:1 methanol:dimethylsulfoxide (with few drops of TFA were added) and was purified by Gilson® reverse phase prep HPLC (5 to 70% acetonitrile/water with 0.1% TFA, linear gradient) to afford the title compound as a bis trifluoroacetic acid (TFA) salt. $^1$H NMR (300 MHz, dimethylsulfoxide-d$_6$) δ ppm 12.03 (s, 1H), 10.01 (s, 1H), 9.64 (s, 1H), 9.06 (s, 1H), 7.77 (d, J=5.9, 2H), 7.73 (s, 1H), 7.56-7.48 (m, J=5.7, 3.9, 2.3, 1H), 7.42-7.32 (m, 3H), 7.00 (d, J=9.1, 2H), 3.79 (brd, J=13.2, 2H), 3.53 (brd, J=11.7, 2H), 3.30-3.08 (m, J=10.3, 2H), 3.03-2.81 (m, 5H); MS (ESI) m/z 448 (M+H)$^+$.

Example 2

6-(2-chlorophenyl)-2-{[4-(4-methylpiperazin-1-yl)phenyl]amino}-8-phenylpyrido[2,3-d]pyrimidin-5(8H)-one Example 2A 6-(2-chlorophenyl)-2-(methylthio)-8-phenylpyrido[2,3-d]pyrimidin-5(8H)-one A 25 mL reaction vessel was charged with Example 1B (143 mg, 0.471 mmol), phenylboronic acid (86 mg, 0.706 mmol) and copper(II)acetate (103 mg, 0.565 mmol). Dichloromethane (4.7 mL, 0.1 M) was added followed by triethylamine (131 µl, 0.942 mmol). The flask was capped and stirred at ambient temperature overnight. Silica gel was added (for dry loading), followed by CH$_2$Cl$_2$ (10 mL) and the mixture was concentrated. Purification by flash chromatography (Isco®, Redi-Sep® column 12 G Redi-Sep column, 0% to 60% ethyl acetate/hexane) afforded the title compound. MS (ESI) m/z 380 (M+H)$^+$.

Example 2B 6-(2-chlorophenyl)-2-{[4-(4-methylpiperazin-1-yl)phenyl]amino}-8-phenylpyrido[2,3-d]pyrimidin-5(8H)-one A 5 mL microwave vessel was charged with Example 2A (51 mg, 0.134 mmol) and 4-(4-methylpiperazin-1-yl)aniline (257 mg, 1.343 mmol, 10 equiv.). The vessel was capped and the solid mixture heated at 180° C. for 16 hours. After cooling to ambient temperature, the crude material was purified by flash chromatography (Isco®, Redi-Sep® column 12 G column, 0-50% 2:1 methanol:water in ethyl acetate). The fractions were collected, concentrated and purified again by Gilson® reverse phase prep HPLC (5 to 70% acetonitrile/water with 0.1% TFA, linear gradient) to afford the title compound as a bis TFA salt. $^1$H NMR (300 MHz, dimethylsulfoxide-d$_6$) δ ppm 10.15 (s, 1H), 9.60 (s, 1H), 9.15 (s, 1H), 8.06 (s, 1H), 7.72-7.31 (m, 11H), 6.88-6.62 (m, 2H), 3.70 (brd, J=13.0, 2H), 3.51 (brd, J=11.7, 2H), 3.25-3.04 (m, J=8.3, 2H), 2.97-2.76 (m, 5H); MS (ESI) m/z 523 (M+H)$^+$.

Example 3

6-(2-chlorophenyl)-2-{[4-(4-methylpiperazin-1-yl)phenyl]amino}-7-phenylpyrido[2,3-d]pyrimidin-5(8H)-one Example 3A 6-(2-chlorophenyl)-2-(methylthio)-7-phenylpyrido[2,3-d]pyrimidin-5(8H)-one A 2 dram vial, equipped with stir bar and septa, was charged with tris(dibenzylideneacetone)dipalladium(0) (27.8 mg, 0.030 mmol), benzamide (184 mg, 1.520 mmol), Xantphos (4,5-bis(diphenylphosphino)-9,9-dimethylxanthene, 44.0 mg, 0.076 mmol), Example 1A (238 mg, 0.760 mmol) and cesium carbonate (743 mg, 2.280 mmol). The mixture was evacuated and backfilled with nitrogen (three times). Dioxane (1.9 mL, 0.4 M) was added and the mixture was evacuated and backfilled with nitrogen (three times). The mixture was stirred at 100° C. for 3 hours. Next, sodium tert-butoxide (146 mg, 1.520 mmol) was added and the mixture stirred at 100° C. for an additional hour. After cooling to ambient temperature, aqueous 1M HCl (50 mL, 1M) was added and the mixture was poured into a separatory funnel and extracted with ethyl acetate (3×50 mL). The combined organic extracts were washed with brine, dried over magnesium sulfate, filtered and concentrated. Purification by flash chromatography (Isco®, Redi-Sep® 40 G column, 0-85% gradient) afforded the title compound. MS (ESI) m/z 380 (M+H)$^+$.

Example 3B 6-(2-chlorophenyl)-2-{[4-(4-methylpiperazin-1-yl) phenyl]amino}-7-phenylpyrido[2,3-d]pyrimidin-5 (8H)-one A 5 mL microwave vessel was charged with Example 3A (24 mg, 0.063 mmol) and 4-(4-methylpiperazin-1-yl)aniline (121 mg, 0.63 mmol). The vessel was capped and the solid mixture heated at 180° C. for 3.5 hours. After cooling to ambient temperature, the crude material was dissolved in 1:1 methanol:dimethylsulfoxide (with few drops of TFA) and purified by Gilson® reverse phase prep HPLC (5 to 70% acetonitrile/water with 0.1% TFA, linear gradient) to afford the title compound as a bis TFA salt. $^1$H NMR (300 MHz, dimethylsulfoxide-$d_6$) δ ppm 12.12 (s, 1H), 10.05 (s, 1H), 9.58 (s, 1H), 9.06 (s, 1H), 7.86 (d, J=7.9, 2H), 7.40-7.27 (m, 6H), 7.25-7.03 (m, J=20.9, 19.6, 7.5, 1.9, 3H), 6.96 (d, J=9.1, 2H), 3.76 (brd, J=13.2, 2H), 3.52 (brd, J=11.9, 2H), 3.31-3.06 (m, J=8.7, 2H), 2.97-2.78 (m, 5H); MS (ESI) m/z 523 (M+H)$^+$.

Example 4

6-(2,6-dichlorophenyl)-2-{[4-(4-methylpiperazin-1-yl)phenyl]amino}-8-phenylpyrido[2,3-d]pyrimidin-5 (8H)-one

Example 4A 1-(4-chloro-2-(methylthio)pyrimidin-5-yl)-2-(2,6-dichlorophenyl)ethanone Step 1: Preparation of the CuCN.2LiCl solution.

To a 250 mL round bottom flask was added copper(I) cyanide (8.95 g, 100 mmol) and lithium chloride (8.48 g, 200 mmol). The flask was capped with septa and heated under high vacuum at 140° C. for 3 hours. After cooling to ambient temperature, dry tetrahydrofuran (90 mL) was added and the mixture stirred until the salts were dissolved (24 hours) to give a ~1 M solution.

Step 2: Organozinc Addition.

To a 1.0 M solution of CuCN:2LiCl (64.6 ml, 64.6 mmol) at −25° C. was slowly added a 0.5 M solution of (2,6-dichlorobenzyl)zinc(II) chloride (129 ml, 64.6 mmol). The resulting reaction mixture was stirred for 15 minutes at this temperature. This solution was added over 10 minutes to a stirring solution of the 4-chloro-2-(methylthio)pyrimidine-5-carbonyl chloride (12 g, 53.8 mmol) in 110 mL of dry tetrahydrofuran via cannula. After the addition was complete, the bath was removed and the mixture was stirred at ambient temperature under nitrogen for 1.5 hours. The mixture was quenched with 200 mL of saturated aqueous sodium bicarbonate and after stirring vigorously for 15 min, the mixture was extracted with ethyl acetate (3×100 mL). The combined organic extracts were washed with brine, dried over magnesium sulfate, filtered and concentrated. The crude material was purified by flash chromatography (Isco®, Redi-Sep® column, 0-30% ethyl acetate/hexane) to give an additional amount of the title compound. $^1$H NMR (300 MHz, CDCl$_3$) δ ppm 8.79 (s, 1H), 7.41-7.31 (m, 2H), 7.25-7.16 (m, J=8.8, 7.3, 1H), 4.68 (s, 2H), 2.63 (s, 3H); MS (ESI) m/z 347 (M+H)$^+$.

Example 4B 6-(2,6-dichlorophenyl)-2-(methylthio)pyrido[2,3-d] pyrimidin-5(8H)-one The title compound was prepared as described in Example 1B substituting Example 1A with Example 4A. The residue was purified by flash chromatography (Isco®, Redi-Sep® column, 0-60% ethyl acetate/hexane, gradient) to obtain the title compound. $^1$H NMR (300 MHz, dimethylsulfoxide-$d_6$) δ ppm 12.68 (s, 1H), 9.17 (s, 1H), 8.03 (d, J=5.0, 1H), 7.67-7.52 (m, 2H), 7.43 (dd, J=8.8, 7.1, 1H), 2.62 (s, 3H); MS (ESI) m/z 338 (M+H)$^+$.

Example 4C 6-(2,6-dichlorophenyl)-2-(methylthio)-8-phenylpyrido[2,3-d]pyrimidin-5(8H)-one The title compound was prepared as described in Example 2A substituting Example 1B with Example 4B and the reaction was performed on a 325 mg (0.961 mmol) scale. Purification by flash chromatography (Isco®, Redi-Sep® column, 0% to 60% ethyl acetate/hexane) afforded the title compound. MS (ESI) m/z 414 (M+H)$^+$.

Example 4D 6-(2,6-dichlorophenyl)-2-{[4-(4-methylpiperazin-1-yl)phenyl]amino}-8-phenylpyrido[2,3-d]pyrimidin-5 (8H)-one A 5 mL microwave vessel was charged with Example 4C (206 mg, 0.497 mmol) and 4-(4-methylpiperazin-1-yl)aniline (951 mg, 4.97 mmol). The vessel was capped then the solid mixture heated at 18° C. for 16 hours. After cooling to ambient temperature the crude material was purified by flash chromatography (Isco®, Redi-Sep® column, 0-60% 2:1 methanol:water in ethyl acetate, linear gradient) to obtain the title compound. $^1$H NMR (300 MHz, dimethylsulfoxide-$d_6$) δ ppm 10.14 (s, 1H), 9.12 (s, 1H), 8.17 (s, 1H), 7.76-7.51 (m, 7H), 7.44 (d, J=7.2, 1H), 7.32 (d, J=8.6, 2H), 6.75-6.57 (m, 2H), 3.11-2.96 (m, 4H), 2.47-2.37 (m, 4H), 2.22 (s, 3H); MS (ESI) m/z 557 (M+H)$^+$.

Example 5

6-(2-chlorophenyl)-8-methyl-2-{[4-(4-methylpiperazin-1-yl)phenyl]amino}pyrido[2,3-d]pyrimidin-5 (8H)-one

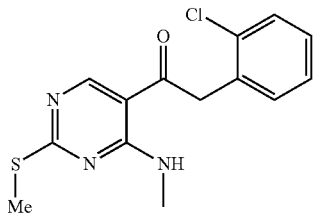 [SMILES: CNc1nc(SC)ncc1C(=O)Cc1ccccc1Cl]

Example 5A 2-(2-chlorophenyl)-1-(4-(methylamino)-2-(methylthio)pyrimidin-5-yl)ethanone The title compound was prepared as described in Example 8A substituting 4A with 1A. The residue was purified by silica gel flash chromatography (Isco®, Redi-Sep® column, 0-30% ethyl acetate/hexane, linear gradient) to obtain the title compound. MS (ESI) m/z 308 (M+H)$^+$.

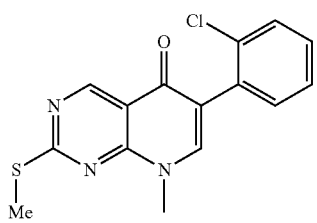 [SMILES: CSc1ncc2c(=O)c(-c3ccccc3Cl)cn(C)c2n1]

Example 5B 6-(2-chlorophenyl)-8-methyl-2-(methylthio)pyrido[2,3-d]pyrimidin-5(8H)-one The title compound was prepared as described in Example 8B substituting Example 8A with Example 5A. The mixture was concentrated and the residue obtained was purified by silica gel chromatography (Isco®, Redi-Sep® column, 0% to 100% ethyl acetate/hexane, linear gradient) to afford the title compound. MS (ESI) m/z 318 (M+H)+.

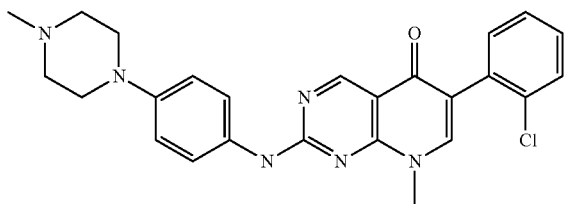 [SMILES: CN1CCN(c2ccc(Nc3ncc4c(=O)c(-c5ccccc5Cl)cn(C)c4n3)cc2)CC1]

Example 5C 6-(2-chlorophenyl)-8-methyl-2-{[4-(4-methylpiperazin-1-yl)phenyl]amino}pyrido[2,3-d]pyrimidin-5(8H)-one A 5 mL microwave vessel was charged with Example 5B (21.7 mg, 0.068 mmol) and 4-(4-methylpiperazin-1-yl)aniline (131 mg, 0.683 mmol). The vessel was capped then the solid mixture heated at 180° C. for 16 hours. After cooling to ambient temperature the crude material was purified by flash chromatography (Isco®, Redi-Sep® column, 0-50% 2:1 methanol:water in ethyl acetate, linear gradient). The material was purified further by Gilson® reverse-phase prep HPLC (5 to 70% acetonitrile/water with 0.1% TFA, linear gradient) to obtain the title compound as a bis TFA salt. $^1$H NMR (300 MHz, dimethylsulfoxide-$d_6$) δ ppm 10.17 (s, 1H), 9.55 (s, 1H), 9.08 (s, 1H), 8.08 (s, 1H), 7.75 (d, J=7.8, 2H), 7.60-7.48 (m, 1H), 7.46-7.30 (m, 3H), 7.03 (d, J=9.2, 2H), 3.88-3.74 (m, 5H), 3.27-3.06 (m, 2H), 3.01-2.80 (m, 4H), 2.50 (s, 3H, within dimethylsulfoxide-$d_6$); MS (ESI) m/z 461 (M+H)+.

Example 6

6-(2,6-dichlorophenyl)-2-{[4-(4-methylpiperazin-1-yl)phenyl]amino}-8,9-dihydropyrimido[4,5-e]indolizin-5(7H)-one

Example 6A 6-(2,6-dichlorophenyl)-2-(methylthio)-8,9-dihydropyrimido[4,5-e]indolizin-5(7H)-one The title compound was prepared as described in Example 3A substituting Example 1A with Example 4A (0.150 g, 0.431 mmol) and substituting benzamide with pyrrolidin-2-one (0.033 ml, 0.431 mmol). Purification by flash chromatography (Isco®, Redi-Sep® column, 0-60% ethyl acetate/hexane, linear gradient) afforded the title compound. $^1$H NMR (300 MHz, dimethylsulfoxide-$d_6$) δ ppm 9.12 (s, 1H), 7.63-7.56 (m, 2H), 7.46 (dd, J=9.0, 7.2, 1H), 4.50-4.34 (m, 2H), 2.81 (t, J=7.7, 2H), 2.64 (s, 3H), 2.30-2.13 (m, 2H); MS (ESI) m/z 461 (M+H)+.

Example 6B 6-(2,6-dichlorophenyl)-2-{[4-(4-methylpiperazin-1-yl)phenyl]amino}-8,9-dihydropyrimido[4,5-e]indolizin-5(7H)-one The title compound was prepared as described in Example 5 substituting Example 5B with Example 6A (45 mg, 0.119 mmol). The crude residue was purified by flash chromatography (Isco®, Redi-Sep® column, 0-50% 2:1 methanol:water in ethyl acetate, linear gradient). The material obtained was purified further by Gilson® reverse-phase prep HPLC (5 to 70% acetonitrile/water with 0.1% TFA, linear gradient) to afford the title compound as a bis TFA salt. $^1$H NMR (300 MHz, dimethylsulfoxide-$d_6$) δ ppm 10.16 (s, 1H), 9.55 (s, 1H), 9.01 (s, 1H), 7.77 (d, J=7.0, 2H), 7.63-7.53 (m, 2H), 7.44 (dd, J=8.9, 7.2, 1H), 7.03 (d, J=9.1, 2H), 4.36 (t, J=7.2, 2H), 3.75-3.59 (m, 2H), 3.27-3.05 (m, 2H), 3.01-2.83 (m, 4H), 2.82-2.68 (m, 2H), 2.50 (s, 3H), 2.32-2.12 (m, 2H); MS (ESI) m/z 521.0 (M+H)+.

Example 7

6-(2,6-dichlorophenyl)-2-{[4-(4-methylpiperazin-1-yl)phenyl]amino}-8-(pyridin-4-yl)pyrido[2,3-d]pyrimidin-5(8H)-one

Example 7A 6-(2,6-dichlorophenyl)-2-(methylthio)-8-(pyridin-4-yl)pyrido[2,3-d]pyrimidin-5(8H)-one The title compound was prepared as described in Example 2A substituting Example 1B with Example 4B (199 mg, 0.588 mmol) and substituting phenyl boronic acid for pyridin-4-ylboronic acid (217 mg, 1.765 mmol). Purification by flash chromatography (Isco®, Redi-Sep® column, 0% to 100% ethyl acetate/hexane, linear gradient) afforded the title compound. MS (ESI) m/z 415 (M+H)+.

Example 7B 6-(2,6-dichlorophenyl)-2-{[4-(4-methylpiperazin-1-yl)phenyl]amino}-8-(pyridin-4-yl)pyrido[2,3-d]pyrimidin-5(8H)-one A 4 dram vial was charged with Example 7A (50 mg, 0.120 mmol), 4-(4-methylpiperazin-1-yl)aniline (230 mg, 1.204 mmol) and the mixture was stirred at 180° C. for 16 hours. After cooling to ambient temperature the mixture was purified directly by flash chromatography (Isco®, Redi-Sep® column, 0% 2:1 methanol:water in ethyl acetate to 50%, linear gradient). The material obtained was purified further by Gilson® reverse-phase prep HPLC (5 to 70% acetonitrile/water with 0.1% TFA, linear gradient) to afford the title compound as a tris TFA salt. $^1$H NMR (300 MHz, CD$_3$OD) δ ppm 9.25 (s, 1H), 8.80 (dd, J=4.7, 1.6, 2H), 8.13 (s, 1H), 7.72 (d, J=6.2, 2H), 7.54-7.47 (m, 2H), 7.43-7.29 (m, 4H), 6.96-

6.75 (m, 2H), 3.87-3.70 (m, 2H), 3.67-3.56 (m, 2H), 3.56-3.50 (m, 1H), 3.40-3.36 (m, 1H), 3.26-3.21 (m, 1H), 3.10-3.04 (m, 1H), 2.99 (s, 3H); MS (ESI) m/z 558 (M+H)$^+$.

Example 8

6-(2,6-dichlorophenyl)-8-methyl-2-{[4-(4-methylpiperazin-1-yl)phenyl]amino}pyrido[2,3-d]pyrimidin-5(8H)-one Example 8A 2-(2,6-dichlorophenyl)-1-(4-(methylamino)-2-(methylthio)pyrimidin-5-yl)ethanone A 2 dram vial, equipped with septa, was charged with Example 4A (500 mg, 1.438 mmol), methanamine (1438 µl, 2.88 mmol) and isopropanol (IPA) (4 mL). The flask was capped and the mixture was stirred at 50° C. for 2.5 hours. After cooling to ambient temperature the mixture was concentrated in vacuo and purified by flash chromatography (Isco®, Redi-Sep® 0-30% ethyl acetate/hexane, linear gradient) to obtain the title compound. $^1$H NMR (300 MHz, dimethylsulfoxide-d$_6$) δ ppm 9.06 (s, 1H), 9.03-8.95 (m, J=4.5, 1H), 7.54-7.45 (m, 2H), 7.35 (dd, J=8.8, 7.3, 1H), 4.67 (s, 2H), 2.96 (d, J=4.8, 3H), 2.53 (s, 3H); MS (ESI) m/z 342 (M+H)$^+$.

Example 8B 6-(2,6-dichlorophenyl)-8-methyl-2-(methylthio)pyrido[2,3-d]pyrimidin-5(8H)-one A 5 mL microwave vessel was charged with Example 8A (366 mg, 1.069 mmol), DMF-dimethylacetal (2000 µl, 14.94 mmol) was added and the mixture was heated in a Biotage Initiator® microwave reactor at 150° C. until completion of the reaction as indicated by LC/MS analysis (~2 hours). The mixture obtained was concentrated in vacuo and purified directly by flash chromatography (Isco®, Redi-Sep® column, 0% to 100% ethyl acetate/hexane) to obtain the title compound. MS (ESI) m/z 352 (M+H)$^+$.

Example 8C 6-(2,6-dichlorophenyl)-8-methyl-2-{[4-(4-methylpiperazin-1-yl)phenyl]amino}pyrido[2,3-d]pyrimidin-5(8H)-one Example 8B (84 mg, 0.238 mmol) was dissolved in CH$_2$Cl$_2$ (2385 µl) and m-CPBA (64.1 mg, 0.286 mmol) was added. The mixture was stirred at ambient temperature for 20 minutes and 4-(4-methylpiperazin-1-yl)aniline (54.7 mg, 0.286 mmol) and TFA (36.7 µl, 0.477 mmol) were added. The mixture was concentrated to remove most of the CH$_2$Cl$_2$ and redissolved in 1 mL of acetonitrile. The mixture was heated at 90° C. for 16 hours. After cooling to ambient temperature, the mixture was poured into a separatory funnel, diluted with 30 mL of ethyl acetate and the organic washed with 20 mL of saturated aqueous sodium bicarbonate, 20 mL of saturated aqueous brine, dried over magnesium sulfate, filtered and concentrated in vacuo. The residue obtained was purified by flash chromatography (Isco®, Redi-Sep® column, 0-50% 2:1 methanol:water in ethyl acetate, linear gradient) to afford the title compound. $^1$H NMR (400 MHz, dimethylsulfoxide-d$_6$) δ ppm 9.72 (s, 1H), 9.04 (s, 1H), 7.94 (s, 1H), 7.64 (d, J=9.0, 2H), 7.55-7.47 (m, 2H), 7.39 (dd, J=8.8, 7.3, 1H), 6.92 (d, J=9.1, 2H), 3.75 (s, 3H), 3.18-3.07 (m, 4H), 2.51-2.42 (m, 4H), 2.23 (s, 3H); MS (ESI) m/z 495 (M+H)$^+$.

Example 9

6-(2,6-dichlorophenyl)-8-(4-fluorophenyl)-2-{[4-(4-methylpiperazin-1-yl)phenyl]amino}pyrido[2,3-d]pyrimidin-5(8H)-one Example 9A 2-(2,6-dichlorophenyl)-1-(4-(4-fluorophenylamino)-2-(methylthio)pyrimidin-5-yl)ethanone The title compound was prepared as described in Example 8A substituting methanamine with 4-fluoroaniline (49.7 µl, 0.518 mmol) and on 90 mg scale (0.259 mmol) of Example 4A. The residue was purified by flash chromatography (Isco®, Redi-Sep® column, 0-30% ethyl acetate/hexane, linear gradient) to obtain the title compound. $^1$H NMR (300 MHz, dimethylsulfoxide-d$_6$) δ ppm 10.93 (s, 1H), 9.29 (s, 1H), 7.76-7.63 (m, 2H), 7.57-7.47 (m, 2H), 7.38 (dd, J=8.8, 7.3, 1H), 7.27-7.10 (m, 2H), 4.81 (s, 2H), 2.50 (s, J=1.8, 3H, within the dimethylsulfoxide-d$^6$ signal); MS (ESI) m/z 422 (M+H)$^+$.

Example 9B 6-(2,6-dichlorophenyl)-8-(4-fluorophenyl)-2-(methylthio)pyrido[2,3-d]pyrimidin-5(8H)-one The title compound was prepared as described in Example 8B, substituting Example 8A with Example 9A with the exception that the mixture was heated in a Biotage Initiator® microwave reactor at 140° C. for 45 minutes instead. The mixture was concentrated and purified directly by flash chromatography (Isco®, Redi-Sep® column, 0 to 50% ethyl acetate/hexane, linear gradient) to afford the title compound. $^1$H NMR (300 MHz, dimethylsulfoxide-d$_6$) δ ppm 9.25 (s, 1H), 8.40 (s, 1H), 7.74-7.62 (m, 2H), 7.61-7.53 (m, 2H), 7.50-7.36 (m, 3H), 2.32 (s, 3H); MS (ESI) m/z 432.1 (M+H)$^+$.

Example 9C 6-(2,6-dichlorophenyl)-8-(4-fluorophenyl)-2-{[4-(4-methylpiperazin-1-yl)phenyl]amino}pyrido[2,3-d]pyrimidin-5(8H)-one The title compound was prepared as described in Example 5C substituting Example 5B with Example 9B. The crude residue was purified by flash chromatography (Isco®, Redi-Sep® column, 0% 2:1 methanol:water in ethyl acetate to 50% 2:1 methanol:water in ethyl acetate, linear gradient) to obtain the title compound. $^1$H NMR (300 MHz, dimethylsulfoxide-d$_6$) δ ppm 10.15 (s, 1H), 9.09 (s, 1H), 8.21 (s, 1H), 7.68-7.59 (m, 2H), 7.59-7.53 (m, 2H), 7.52-7.39 (m, 3H), 7.31 (d, J=8.4, 2H), 6.68 (d, J=7.3, 2H), 3.09-2.98 (m, 4H), 2.47-2.40 (m, 4H), 2.27-2.16 (m, 3H); MS (ESI) m/z 575 (M+H)$^+$.

Example 10

8-cyclopropyl-6-(2,6-dichlorophenyl)-2-{[4-(4-methylpiperazin-1-yl)phenyl]amino}pyrido[2,3-d]pyrimidin-5(8H)-one Example 10A 1-(4-(cyclopropylamino)-2-(methylthio)pyrimidin-5-yl)-2-(2,6-dichlorophenyl)ethanone The title compound was prepared as described in Example 8A substituting methanamine with cyclopropanamine and the reaction was performed on a 180 mg scale (Example 4A). The crude material was purified by flash chromatography (Isco®, Redi-Sep® column 0-40% ethyl acetate/hexane, linear gradient) to obtain the title compound. MS (ESI) m/z 367 (M+H)+.

Example 10B 8-cyclopropyl-6-(2,6-dichlorophenyl)-2-(methylthio)pyrido[2,3-d]pyrimidin-5(8H)-one The title compound was prepared as described in Example 8B substituting Example 8A with Example 10A with the exception that the mixture was heated in a Biotage Initiator® microwave reactor at 140° C. for 90 minutes, and the reaction was performed on a 0.388 mmol scale (Example 10A). The mixture was then concentrated and purified directly by flash chromatography (Isco®, Redi-Sep® column, 0 to 50% ethyl acetate/hexane, linear gradient) to afford the title compound. $^1$H NMR (300 MHz, dimethylsulfoxide-$d_6$) δ ppm 9.16 (s, 1H), 8.23 (s, 1H), 7.61-7.53 (m, 2H), 7.44 (dd, J=9.0, 7.1, 1H), 3.75-3.61 (m, 1H), 2.67 (s, 3H), 1.22-0.97 (m, 4H); MS (ESI) m/z 378 (M+H)+.

Example 10C 8-cyclopropyl-6-(2,6-dichlorophenyl)-2-{[4-(4-methylpiperazin-1-yl)phenyl]amino}pyrido[2,3-d]pyrimidin-5(8H)-one The title compound was prepared as described in Example 5C substituting Example 5B with Example 10B and the reaction was performed on a 0.161 mmol scale (Example 10B). The crude material was purified by flash chromatography (Isco®, Redi-Sep® column, 0% 2:1 methanol:water in ethyl acetate to 50% 2:1 methanol:water in ethyl acetate, linear gradient) to obtain the title compound. $^1$H NMR (300 MHz, dimethylsulfoxide-$d_6$) δ ppm 10.18 (s, 1H), 9.04 (s, 1H), 7.98 (s, 1H), 7.95-7.76 (m, 2H), 7.61-7.49 (m, 2H), 7.42 (dd, J=9.0, 7.2, 1H), 6.96 (d, J=9.2, 2H), 3.66-3.48 (m, 1H), 3.16-3.04 (m, 4H), 2.48-2.40 (m, 4H), 2.26 (s, 3H), 1.30-0.94 (m, 4H); MS (ESI) m/z 521 (M+H)+.

Example 11

6-(2,6-dichlorophenyl)-2-{[4-(4-methylpiperazin-1-yl)phenyl]amino}-8-(2,2,2-trifluoroethyl)pyrido[2,3-d]pyrimidin-5(8H)-one

Example 11A 2-(2,6-dichlorophenyl)-1-(2-(methylthio)-4-(2,2,2-trifluoroethylamino)pyrimidin-5-yl)ethanone The title compound was prepared as described in Example 8A substituting methanamine with 2,2,2-trifluoroethanamine and the reaction was performed on a 180 mg scale (0.518 mmol of Example 4A). The crude material was purified by flash chromatography (Isco®, Redi-Sep® column 0-30% ethyl acetate/hexane, linear gradient) to obtain the title compound. MS (ESI) m/z 410 (M+H)+.

Example 11B 6-(2,6-dichlorophenyl)-2-(methylthio)-8-(2,2,2-trifluoroethyl)pyrido[2,3-d]pyrimidin-5(8H)-one The title compound was prepared as described in Example 8B substituting Example 8A with Example 11A with the exception that the mixture was heated in a Biotage Initiator® microwave reactor at 140° C. for 45 minutes instead and on 0.285 mmol scale (Example 11A). The mixture was then concentrated and purified directly by flash chromatography (Isco®, Redi-Sep® column, 0 to 50% ethyl acetate/hexane, linear gradient) to afford the title compound. $^1$H NMR (300 MHz, dimethylsulfoxide-$d_6$) δ ppm 9.23 (s, 1H), 8.33 (s, 1H), 7.67-7.57 (m, 2H), 7.49 (dd, J=8.9, 7.1, 1H), 5.33 (d, J=8.8, 3H), 2.64 (s, 3H); MS (ESI) m/z 420.3 (M+H)+.

Example 11C 6-(2,6-dichlorophenyl)-2-{[4-(4-methylpiperazin-1-yl)phenyl]amino}-8-(2,2,2-trifluoroethyl)pyrido[2,3-d]pyrimidin-5(8H)-one The title compound was prepared as described in Example 5 substituting Example 5B with Example 11B and the reaction was performed on a 0.121 mmol scale (Example 11B). The crude material was purified by flash chromatography (Isco®, Redi-Sep® column 0% 2:1 methanol:water in ethyl acetate to 50% 2:1 methanol:water in ethyl acetate, linear gradient) to obtain the title compound. $^1$H NMR (300 MHz, dimethylsulfoxide-$d_6$) δ ppm 10.30 (s, 1H), 9.09 (s, 1H), 8.11 (s, 1H), 7.69-7.52 (m, 4H), 7.46 (dd, J=8.9, 7.1, 1H), 6.93 (d, J=9.1, 2H), 5.16 (q, J=8.7, 2H), 3.19-3.04 (m, 4H), 2.48-2.39 (m, 4H), 2.22 (s, 3H); MS (ESI): m/z 564 (M+H)+.

Example 12

6-(2,6-dichlorophenyl)-2-{[4-(4-methylpiperazin-1-yl)phenyl]amino}-8-(pyridin-4-ylmethyl)pyrido[2,3-d]pyrimidin-5(8H)-one

Example 12A 2-(2,6-dichlorophenyl)-1-(2-(methylthio)-4-(pyridin-4-ylmethylamino)pyrimidin-5-yl)ethanone The title compound was prepared as described in Example 8A substituting methanamine with pyridin-4-ylmethanamine, and the reaction was performed on 180 mg scale (0.518 mmol Example 4A) and was stirred at 60° C. for 4 hours instead. The crude material was purified by flash chromatography (Isco®, Redi-Sep® column 0-100% ethyl acetate/hexane, linear gradient) to obtain the title compound. MS (ESI) m/z 419 (M+H)+.

Example 12B 6-(2,6-dichlorophenyl)-2-(methylthio)-8-(pyridin-4-ylmethyl)pyrido[2,3-d]pyrimidin-5(8H)-one The title compound was prepared as described in Example 8B substituting Example 8A with Example 12A with the exception that the mixture was heated in a Biotage Initiator® microwave reactor at 140° C. for 45 minutes instead and the reaction was performed on 0.424 mmol scale (Example 12A). The mixture was concentrated in vacuo then purified directly by flash chromatography (Isco®, Redi-Sep® column, 20% ethyl acetate/hexane to 100% ethyl acetate then 15% methanol/ethyl acetate) to afford the title compound. MS (ESI) m/z 429 (M+H)+.

Example 12C 6-(2,6-dichlorophenyl)-2-{[4-(4-methylpiperazin-1-yl)phenyl]amino}-8-(pyridin-4-ylmethyl)pyrido[2,3-d]pyrimidin-5(8H)-one The title compound was prepared as described in Example 5C Example 5B with Example 12B and the reaction was performed on a 0.163 mmol scale (Example 12B). The crude material was purified by Gilson® reverse-phase prep HPLC (5 to 70% acetonitrile/water with 0.1% TFA, linear gradient) to obtain the title compound as a tris TFA salt. $^1$H NMR (300 MHz, dimethylsulfoxide-$d_6$) δ ppm 10.19 (s, 1H), 9.70 (s, 1H), 9.10 (s, 1H), 8.64 (d, J=6.1, 2H), 8.31 (s, 1H), 7.65-7.54 (m, 2H), 7.52-7.31 (m, 5H), 6.92 (d, J=8.8, 2H), 5.54 (s, 2H), 3.79 (brd, J=13.3, 2H), 3.54 (brd, J=11.9, 2H), 3.27-3.10 (m, 2H), 3.01-2.82 (m, 5H); MS (ESI) m/z 572.1 (M+H)$^+$.

Example 13

6-(2,6-dichlorophenyl)-8-[2-(dimethylamino)ethyl]-2-{[4-(4-methylpiperazin-1-yl)phenyl]amino}pyrido[2,3-d]pyrimidin-5(8H)-one

Example 13A 2-(2,6-dichlorophenyl)-1-(4-(2-(dimethylamino)ethylamino)-2-(methylthio)pyrimidin-5-yl)ethanone The title compound was prepared as described in Example 8A substituting methanamine with 2-(dimethylamino)ethylamine, and the reaction was performed on 180 mg scale (0.518 mmol Example 4A) and was stirred at 60° C. for 4 hours instead. The crude material was purified by flash chromatography (Isco®, Redi-Sep® column 20% ethyl acetate/hexane to 100% ethyl acetate then 15% methanol/ethyl acetate) to obtain the title compound. MS (ESI): m/z 399 (M+H)$^+$.

Example 13B 6-(2,6-dichlorophenyl)-8-(2-(dimethylamino)ethyl)-2-(methylthio)pyrido[2,3-d]pyrimidin-5(8H)-one The title compound was prepared as described in Example 8B substituting Example 8A with Example 13A with the exception that the mixture was heated in a Biotage Initiator® microwave reactor at 140° C. for 45 minutes and the reaction was performed on a 0.446 mmol scale (Example 13A). The mixture was concentrated and was purified directly by flash chromatography (Isco®, Redi-Sep® column, 20% ethyl acetate/hexane to 100% ethyl acetate then 15% methanol/ethyl acetate) to afford the title compound. MS (ESI) m/z 410 (M+H)$^+$.

Example 13C 6-(2,6-dichlorophenyl)-8-[2-(dimethylamino)ethyl]-2-{[4-(4-methylpiperazin-1-yl)phenyl]amino}pyrido[2,3-d]pyrimidin-5(8H)-one The title compound was prepared as described in Example 5C substituting Example 5B with Example 13B and the reaction was performed on a 0.156 mmol scale (Example 13B). The crude material was purified by Gilson® reverse-phase prep HPLC (5 to 70% acetonitrile/water with 0.1% TFA, linear gradient) to obtain the title compound as a tris TFA salt. $^1$H NMR (300 MHz, dimethylsulfoxide-$d_6$) δ ppm 9.88 (s, 3H), 9.09 (s, 1H), 8.16 (s, 1H), 7.71-7.53 (m, 3H), 7.46 (dd, J=9.0, 7.2, 1H), 7.03 (d, J=9.1, 2H), 4.56 (s, 2H), 3.61-3.47 (m, 5H), 3.17 (s, 3H), 3.02-2.72 (m, 11H); MS (ESI) m/z 552 (M+H)$^+$.

Example 14

6-(2,6-dichlorophenyl)-8-methyl-2-[(2'-methyl-2',3'-dihydro-1'H-spiro[cyclopropane-1,4'-isoquinolin]-7'-yl)amino]pyrido[2,3-d]pyrimidin-5(8H)-one The title compound was prepared as described in Example 8C substituting 4-(4-methylpiperazin-1-yl)aniline with 2'-methyl-2',3'-dihydro-1'H-spiro[cyclopropane-1,4'-isoquinolin]-7'-amine and the reaction was performed on a 0.238 mmol scale (Example 8B). Purification of the residue by flash chromatography (Isco®, Redi-Sep® column, 0-40% 2:1 methanol:water in ethyl acetate, linear gradient) afforded the title compound. $^1$H NMR (300 MHz, dimethylsulfoxide-$d_6$) δ ppm 10.23 (s, 1H), 9.08 (s, 1H), 8.15 (s, 1H), 7.69-7.50 (m, 4H), 7.44 (dd, J=8.8, 7.2, 1H), 6.71 (d, J=8.6, 1H), 3.78 (s, 3H), 3.59 (s, 2H), 2.45 (s, 2H), 2.32 (s, 3H), 1.00-0.75 (m, J=20.6, 4H); MS (ESI) m/z 492 (M+H)$^+$.

Example 15

8-cyclobutyl-6-(2,6-dichlorophenyl)-2-{[4-(4-methylpiperazin-1-yl)phenyl]amino}pyrido[2,3-d]pyrimidin-5(8H)-one

Example 15A 1-(4-(cyclobutylamino)-2-(methylthio)pyrimidin-5-yl)-2-(2,6-dichlorophenyl)ethanone The title compound was prepared as described in Example 8A substituting methanamine with cyclobutanamine and the reaction was performed on a 180 mg scale (0.518 mmol of Example 4A). The crude material was purified by flash chromatography (Isco®, Redi-Sep® column 0-30% ethyl acetate/hexane, linear gradient) to obtain the title compound. MS (ESI) m/z 382 (M+H)$^+$.

Example 15B 8-cyclobutyl-6-(2,6-dichlorophenyl)-2-(methylthio)pyrido[2,3-d]pyrimidin-5(8H)-one The title compound was prepared as described in Example 8B substituting Example 8A with Example 15A with the exception that the mixture was heated in a Biotage Initiator® microwave reactor at 140° C. for 45 minutes and the reaction was performed on a 0.282 mmol scale (Example 15A). The mixture was then concentrated and purified directly by flash chromatography (Isco®, Redi-Sep® column, 0 to 50% ethyl acetate/hexane, linear gradient) to afford the title compound. $^1$H NMR (300 MHz, dimethylsulfoxide-$d_6$) δ ppm 9.18 (s, 1H), 8.43 (s, 1H), 7.62-7.54 (m, 2H), 7.45 (dd, J=9.0, 7.1, 1H), 5.66-5.44 (m, 1H), 2.66 (s, 3H), 2.49-2.38 (m, 4H), 1.94-1.67 (m, 2H); MS (ESI) m/z 392 (M+H)$^+$.

Example 15C 8-cyclobutyl-6-(2,6-dichlorophenyl)-2-{[4-(4-methylpiperazin-1-yl)phenyl]amino}pyrido[2,3-d]pyrimidin-5(8H)-one The title compound was prepared as described in Example 5C substituting Example 5B with Example 15B and the reaction was performed on a 0.212 mmol scale (Example 15B). The crude material was purified by flash chromatography (Isco®, Redi-Sep® column, 0% 2:1 methanol:water in ethyl acetate to 40% 2:1 methanol:water in ethyl acetate, linear gradient) to obtain the title compound. $^1$H NMR (300 MHz, dimethylsulfoxide-$d_6$) δ ppm 10.09 (s, 1H), 9.05 (s, 1H), 8.25 (s, 1H), 7.64 (brd, J=7.5, 2H), 7.59-7.50 (m, 2H), 7.43 (dd, J=8.9, 7.2, 1H), 6.97 (d, J=9.0, 2H), 5.68-5.28 (m, 1H), 3.16-3.04 (m, 4H), 2.48-2.30 (m, 8H), 2.23 (s, 3H), 1.93-1.67 (m, 2H). MS (ESI) m/z 535 (M+H)$^+$.

Example 16

6-(2,6-dichlorophenyl)-8-(2-hydroxy-2-methylpropyl)-2-{[4-(4-methylpiperazin-1-yl)phenyl]amino}pyrido[2,3-d]pyrimidin-5(8H)-one

Example 16A 2-(2,6-dichlorophenyl)-1-(4-(2-hydroxy-2-methylpropylamino)-2-(methylthio)pyrimidin-5-yl)ethanone The title compound was prepared as described in Example 8A substituting methanamine with 1-amino-2-methylpropan-2-ol, and the reaction was performed on 180 mg scale (0.518 mmol of Example 4A) and stirring at 50° C. for 4 hours instead. The crude material was purified by flash chromatography (Isco®, Redi-Sep® column 0-50% ethyl acetate/hexane, linear gradient) to obtain the title compound. MS (ESI) m/z 400 (M+H)$^+$.

Example 16B 6-(2,6-dichlorophenyl)-8-(2-methylpropyl)-2-(methylthio)pyrido[2,3-d]pyrimidin-5(8H)-one The title compound was prepared as described in Example 8B substituting Example 8A with Example 16A with the exception that the mixture was heated in a Biotage Initiator® microwave reactor at 150° C. for 90 minutes instead and on 0.44 mmol scale of Example 12A. The mixture was then concentrated and purified directly by flash chromatography (Isco®, Redi-Sep® column, 20% ethyl acetate/hexane to 100% ethyl acetate, linear gradient) to afford the title compound. $^1$H NMR (300 MHz, dimethylsulfoxide-$d_6$) δ ppm 9.19 (s, 1H), 8.11 (s, 1H), 7.62-7.55 (m, 2H), 7.46 (dd, J=9.0, 7.1, 1H), 4.75 (s, 1H), 4.37 (s, 2H), 2.64 (s, 3H), 1.13 (s, 6H); MS (ESI) m/z 410 (M+H)$^+$.

Example 16C 6-(2,6-dichlorophenyl)-8-(2-hydroxy-2-methylpropyl)-2-{[4-(4-methylpiperazin-1-yl)phenyl]amino}pyrido[2,3-d]pyrimidin-5(8H)-one The title compound was prepared as described in Example 8C substituting Example 8B with Example 16B and on a 0.171 mmol scale (Example 16B). The crude material was purified by Gilson® reverse-phase prep HPLC (5 to 70% acetonitrile/water with 0.1% TFA, linear gradient) to obtain the title compound as a bis TFA salt. $^1$H NMR (300 MHz, dimethylsulfoxide-$d_6$) δ ppm 10.14 (brs, 1H), 9.59 (brs, 1H), 9.09 (s, 1H), 7.92 (s, 1H), 7.72 (d, J=8.3, 2H), 7.61-7.52 (m, 2H), 7.44 (dd, J=8.9, 7.1, 1H), 7.03 (d, J=9.1, 2H), 4.29 (s, 2H), 3.90-3.73 (m, 2H), 3.54-3.46 (m, 2H), 3.29-3.07 (m, 2H), 2.88 (d, J=3.7, 5H), 1.14 (s, 6H); MS (ESI) m/z 553 (M+H)$^+$.

Example 17

8-cyclopropyl-6-(2,6-dichlorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one The title compound was prepared as described in Example 8C substituting 4-(4-methylpiperazin-1-yl)aniline for 2'-methyl-2',3'-dihydro-1'H-spiro[cyclopropane-1,4'-isoquinolin]-7'-amine and substituting Example 8B with Example 10B using a 0.139 mmol scale (Example 10B). Purification of the residue by flash chromatography (Isco®, Redi-Sep® column, 0-40% 2:1 methanol:water in ethyl acetate, linear gradient) afforded the title compound. $^1$H NMR (300 MHz, dimethylsulfoxide-$d_6$) δ ppm 10.23 (d, J=14.0, 1H), 9.07 (s, 1H), 8.05 (s, 1H), 7.78-7.64 (m, 2H), 7.60-7.50 (m, 2H), 7.42 (dd, J=9.0, 7.2, 1H), 6.72 (d, J=9.2, 1H), 3.67-3.50 (m, 3H), 2.45 (s, 2H), 2.32 (s, 3H), 1.27-0.99 (m, 4H), 0.87 (d, J=23.9, 4H); MS (ESI) m/z 518.1 (M+H)$^+$.

Example 18

6-(2,6-dichlorophenyl)-2-{[4-(4-methylpiperazin-1-yl)phenyl]amino}pyrido[2,3-d]pyrimidin-5(8H)-one The title compound was prepared as described in Example 5C substituting Example 5B with Example 4B and on a 0.103 mmol scale (Example 4B). The crude material was purified by Gilson® reverse-phase prep HPLC (5 to 70% acetonitrile/water with 0.1% TFA, linear gradient) to obtain the title compound as a bis TFA salt. $^1$H NMR (300 MHz, dimethylsulfoxide-$d_6$) δ ppm 12.12 (s, 1H), 10.04 (s, 1H), 9.63 (s, 1H), 9.05 (s, 1H), 7.82 (d, J=5.9, 1H), 7.74 (d, J=7.5, 2H), 7.58-7.51 (m, 2H), 7.47-7.35 (m, 1H), 7.00 (d, J=9.1, 2H), 3.84-3.74 (m, 2H), 3.57-3.47 (m, 2H), 3.25-3.11 (m, 2H), 2.98-2.84 (m, 5H); MS (ESI) m/z 481.3 (M+H)$^+$.

Example 19

6-(2,6-dichlorophenyl)-8-methyl-2-{[3-methyl-4-(4-methyl-1,4-diazepan-1-yl)phenyl]amino}pyrido[2,3-d]pyrimidin-5(8H)-one The title compound was prepared as described in Example 8C substituting 4-(4-methylpiperazin-1-yl)aniline with 2-methyl-4-(4-methyl-1,4-diazepan-1-yl)aniline and the reaction was performed on a 0.156 mmol scale (Example 8B). The crude material was purified by Gilson® reverse-phase prep HPLC (5 to 70% acetonitrile/Water with 0.1% TFA, linear gradient) to obtain the title compound as a bis TFA salt. $^1$H NMR (300 MHz, dimethylsulfoxide-$d_6$) δ ppm 10.21 (brs, 1H), 9.52 (brs, 1H), 9.08 (s, 1H), 8.15 (s, 1H), 7.75-7.61 (m, 2H), 7.60-7.53 (m, 2H), 7.44 (dd, J=9.0, 7.2, 1H), 7.12 (d, J=8.4, 1H), 3.79 (s, 3H), 3.58-3.17 (m, 6H), 3.14-3.03 (m, 2H), 2.90 (d, J=4.9, 3H), 2.31 (s, 3H), 2.16-2.01 (m, 2H); MS (ESI) m/z 523.3 (M+H)$^+$.

Example 20

6-(2,6-dichlorophenyl)-8-methyl-2-[(2,4,4-trimethyl-1,2,3,4-tetrahydroisoquinolin-7-yl)amino]pyrido[2,3-d]pyrimidin-5(8H)-one The title compound was prepared as described in Example 8c substituting 4-(4-methylpiperazin-1-yl)aniline with 2,4,4- trimethyl-1,2,3,4-tetrahydroisoquinolin-7-amine and the reaction was performed on a 0.156 mmol scale (Example 8B). The crude material was purified by flash chromatography (Isco®, Redi-Sep® column, 0% 2:1 methanol:water in ethyl acetate to 30% 2:1 methanol:water in ethyl acetate, linear gradient) to obtain the title compound. $^1$H NMR (300 MHz, dimethylsulfoxide-$d_6$) δ ppm 10.24 (brs, 1H), 9.09 (s, 1H), 8.15 (s, 1H), 7.67-7.51 (m, 4H), 7.44 (dd, J=8.9, 7.2, 1H), 7.32 (d, J=8.4, 1H), 3.80 (s, 3H), 3.46 (s, 2H), 2.40-2.29 (m, 5H), 1.25 (s, 6H); MS (ESI): m/z 494 (M+H)$^+$.

Example 21

6-(2,6-dichlorophenyl)-2-(2',3'-dihydro-1'H-spiro [cyclopropane-1,4'-isoquinolin]-7'-ylamino)-8-methylpyrido[2,3-d]pyrimidin-5(8H)-one The title compound was prepared as described in Example 8C substituting 4-(4-methylpiperazin-1-yl)aniline with tert-butyl 7'-amino-1'H-spiro[cyclopropane-1,4'-isoquinoline]-2' (3'H)-carboxylate and the reaction was performed on a 0.156 mmol scale (Example 8B). The crude material was purified by Gilson® reverse-phase prep HPLC (5 to 70% acetonitrile/water with 0.1% TFA, linear gradient) to obtain the title compound as a TFA salt. $^1$H NMR (300 MHz, dimethylsulfoxide-$d_6$) δ ppm 10.40 (brs, 1H), 9.22 (brs, 2H), 9.12 (s, 1H), 8.18 (s, 1H), 7.79 (brs, 1H), 7.70-7.61 (m, 1H), 7.61-7.52 (m, 2H), 7.45 (dd, J=8.9, 7.2, 1H), 6.88 (d, J=8.7, 1H), 4.42 (s, 2H), 3.80 (s, 3H), 3.28 (s, 2H), 1.18-0.99 (m, 4H). MS (ESI) m/z 478 (M+H)$^+$.

Example 22

6-(2,6-dichlorophenyl)-2-{[2-(dimethylamino)-2,3-dihydro-1H-inden-5-yl]amino}-8-methylpyrido[2,3-d]pyrimidin-5(8H)-one The title compound was prepared as described in Example 8C substituting 4-(4-methylpiperazin-1-yl)aniline with N,N-dimethyl-2,3-dihydro-1H-indene-2,5-diamine and the reaction was performed on a 0.156 mmol scale (Example 8B). The crude material was purified by Gilson® reverse-phase prep HPLC (5 to 70% acetonitrile/water with 0.1% TFA, linear gradient) to obtain the title compound as a TFA salt. $^1$H NMR (300 MHz, dimethylsulfoxide-$d_6$) δ ppm 10.36 (brs, 1H), 9.80 (brs, 1H), 9.11 (s, 1H), 8.16 (s, 1H), 7.79 (brs, 1H), 7.68 (d, J=8.2, 1H), 7.61-7.53 (m, 2H), 7.44 (dd, J=9.0, 7.2, 1H), 7.25 (d, J=8.3, 1H), 4.19-4.04 (m, 1H), 3.79 (s, 3H), 3.41-3.02 (m, 4H), 2.84 (d, J=4.7, 6H); MS (ESI): m/z 480 (M+H)$^+$.

Example 23

8-cyclopropyl-6-(2,6-dichlorophenyl)-2-[(2,4,4-trimethyl-1,2,3,4-tetrahydroisoquinolin-7-yl)amino]pyrido[2,3-d]pyrimidin-5(8H)-one The title compound was prepared as described in Example 8C substituting 4-(4-methylpiperazin-1-yl)aniline with 2,4,4-trimethyl-1,2,3,4-tetrahydroisoquinolin-7-amine and substituting Example 8B with Example 10B, and the reaction was performed on a 0.145 mmol scale (Example 10B). The crude material was purified by Gilson® reverse-phase prep HPLC (5 to 70% acetonitrile/water with 0.1% TFA, linear gradient) to obtain the title compound. $^1$H NMR (400 MHz, dimethylsulfoxide-$d_6$) δ ppm 9.86 (brs, 1H), 9.06 (s, 1H), 7.89 (s, 1H), 7.70 (dd, J=8.5, 2.2, 1H), 7.63 (d, J=2.1, 1H), 7.55-7.47 (m, 2H), 7.39 (dd, J=8.8, 7.3, 1H), 7.29 (d, J=8.5, 1H), 3.68-3.56 (m, 1H), 3.48 (s, 2H), 2.40-2.31 (m, 5H), 1.26 (s, 6H), 1.21-1.14 (m, 2H), 1.09-1.01 (m, 2H); MS (ESI): m/z 520.1 (M+H)$^+$.

Example 24

8-cyclopropyl-6-(2,6-dichlorophenyl)-2-(2',3'-dihydro-1'H-spiro[cyclopropane-1,4'-isoquinolin]-7'-ylamino)pyrido[2,3-d]pyrimidin-5(8H)-one 8-Cyclopropyl-6-(2,6-dichlorophenyl)-2-(methylthio)pyrido[2,3-d]pyrimidin-5(8H)-one (55 mg, 0.145 mmol) was dissolved in CH$_2$Cl$_2$ (1.4 mL) and meta-chloroperoxybenzoic acid (43.0 mg, 0.174 mmol) was added. The mixture was stirred at ambient temperature for 20 minutes, then tert-butyl 7'-amino-1'H-spiro[cyclopropane-1,4'-isoquinoline]-2' (3'H)-carboxylate (47.9 mg, 0.174 mmol) was added. The mixture was stirred at ambient temperature for 24 hours then concentrated in vacuo. The residue was purified by flash chromatography (2-60% ethyl acetate/hexane, linear gradient) to afford the N-boc protected intermediate. The intermediate was treated with TFA-CH$_2$Cl$_2$ (0.6 mL, 1:1) at room temperature for 1 hour. After concentration, the title compound was obtained. $^1$H NMR (400 MHz, dimethylsulfoxide-$d_6$) δ ppm 10.05 (brs, 1H), 9.37-9.04 (m, 3H), 7.92 (s, 1H), 7.85-7.76 (m, 2H), 7.55-7.47 (m, 2H), 7.39 (dd, J=8.8, 7.3, 1H), 6.88 (d, J=9.3, 1H), 4.40 (s, 2H), 3.70-3.55 (m, 1H), 3.27 (s, 2H), 1.22-1.02 (m, 8H); MS (ESI): m/z 504 (M+H)$^+$.

Example 25

8-cyclopropyl-6-(2,6-dichlorophenyl)-2-{[2-(dimethylamino)-2,3-dihydro-1H-inden-5-yl] amino}pyrido[2,3-d]pyrimidin-5(8H)-one The title compound was prepared as described in Example 8C substituting 4-(4-methylpiperazin-1-yl)aniline with N,N-dimethyl-2,3-dihydro-1H-indene-2,5-diamine and substituting Example 8B with Example 10B using a 0.145 mmol scale (Example 10B). The crude material was purified by Gilson® reverse-phase prep HPLC (5 to 70% acetonitrile/water with 0.1% TFA, linear gradient) to obtain the title compound. $^1$H NMR (400 MHz, dimethylsulfoxide-$d_6$) δ ppm 9.87 (brs, 1H), 9.06 (s, 1H), 7.92-7.82 (m, 2H), 7.63 (d, J=8.1, 1H), 7.52-7.46 (m, 2H), 7.39 (dd, J=8.7, 7.3, 1H), 7.14 (d, J=8.1, 1H), 3.63-3.54 (m, 1H), 3.13-2.71 (m, 5H), 2.20 (d, J=2.8, 6H), 1.22-0.99 (m, 4H); MS (ESI) m/z 506 (M+H)$^+$.

Example 26

6-(2,6-dichlorophenyl)-2-{[4-(4-methylpiperazin-1-yl)phenyl]amino}-8-(propan-2-yl)pyrido[2,3-d]pyrimidin-5(8H)-one Example 26A 2-(2,6-dichlorophenyl)-1-(4-(isopropylamino)-2-(methylthio)pyrimidin-5-yl)ethanone The title compound was prepared as described in Example 8A substituting methanamine with isopropylamine and the reaction was performed on 200 mg scale (Example 4A). The crude material was purified by flash chromatography (Isco®, Redi-Sep® column 2-25% ethyl acetate/hexane, linear gradient) to obtain the title compound. MS (ESI) m/z 370 (M+H)$^+$.

Example 26B 6-(2,6-dichlorophenyl)-8-isopropyl-2-(methylthio) pyrido[2,3-d]pyrimidin-5(8H)-one The title compound was prepared as described in Example 8B substituting Example 8A with Example 26A with the exception that the mixture was heated in a Biotage Initiator® microwave reactor at 160° C. for 60 minutes instead and the reaction was performed on a 0.451 mmol scale (Example 26A). The mixture was then concentrated and purified directly by flash chromatography (Isco®, Redi-Sep® column, 2 to 45% ethyl acetate/hexane, linear gradient) to afford the title compound. MS (ESI) m/z 380 (M+H)$^+$.

Example 26C 6-(2,6-dichlorophenyl)-2-{[4-(4-methylpiperazin-1-yl)phenyl]amino}-8-(propan-2-yl)pyrido[2,3-d]pyrimidin-5(8H)-one The title compound was prepared as described in Example 5C substituting Example 5B with Example 26B and the reaction was performed on a 0.118 mmol scale (Example 26B). The crude material was purified by Gilson® reverse-phase prep HPLC (5 to 70% acetonitrile/water with 0.1% TFA, linear gradient) to obtain the title compound. $^1$H NMR (400 MHz, dimethylsulfoxide-d$_6$) δ ppm 9.68 (brs, 1H), 9.05 (s, 1H), 7.97 (s, 1H), 7.59 (d, J=9.1, 2H), 7.53-7.46 (m, 2H), 7.43-7.35 (m, 1H), 6.92 (d, J=9.1, 2H), 5.56-5.46 (m, 1H), 3.16-3.00 (m, 8H), 2.23 (s, 3H), 1.44 (d, J=6.8, 6H); MS (ESI) m/z 522 (M+H)$^+$.

Example 27

6-(2,6-dichlorophenyl)-2-{[4-(4-methylpiperazin-1-yl)phenyl]amino}-8-(oxetan-3-yl)pyrido[2,3-d]pyrimidin-5(8H)-one

Example 27A 2-(2,6-dichlorophenyl)-1-(2-(methylthio)-4-(oxetan-3-ylamino)pyrimidin-5-yl)ethanone The title compound was prepared as described in Example 8A substituting methanamine with oxetan-3-amine and the reaction was performed on 200 mg scale (Example 4A). The crude material was purified by flash chromatography (Isco®, Redi-Sep® column 2-45% ethyl acetate/hexane, linear gradient) to obtain the title compound. MS (ESI) m/z 384 (M+H)$^+$.

Example 27B 6-(2,6-dichlorophenyl)-2-(methylthio)-8-(oxetan-3-yl)pyrido[2,3-d]pyrimidin-5(8H)-one The title compound was prepared as described in Example 8B substituting Example 8A with Example 27A with the exception that the mixture was heated in a Biotage Initiator® microwave reactor at 150° C. for 60 minutes and the reaction was performed on a 0.452 mmol scale (Example 27A). The mixture was concentrated and purified directly by flash chromatography (Isco®, Redi-Sep® column, 2 to 45% ethyl acetate/hexane, linear gradient) to afford the title compound. MS (ESI) m/z 394 (M+H)$^+$.

Example 27C 6-(2,6-dichlorophenyl)-2-{[4-(4-methylpiperazin-1-yl)phenyl]amino}-8-(oxetan-3-yl)pyrido[2,3-d]pyrimidin-5(8H)-one The title compound was prepared as described in Example 5C substituting Example 5B with Example 27B and the reaction was performed on a 0.076 mmol scale (Example 27B). The crude material was purified by Gilson® reverse-phase prep HPLC (5 to 70% acetonitrile/water with 0.1% TFA, linear gradient) to obtain the title compound. $^1$H NMR (400 MHz, dimethylsulfoxide-d$_6$) δ ppm 9.68 (s, 1H), 9.05 (s, 1H), 8.03 (s, 1H), 7.54-7.46 (m, 4H), 7.40 (dd, J=8.7, 7.3, 1H), 6.95 (d, J=9.0, 2H), 5.82 (p, J=7.0, 1H), 4.91 (t, J=7.5, 2H), 4.83 (t, J=7.1, 2H), 3.17-3.11 (m, 4H), 3.03-2.98 (m, 4H), 2.23 (s, 3H); MS (ESI) m/z 537 (M+H)$^+$.

Example 28

8-tert-butyl-6-(2,6-dichlorophenyl)-2-{[4-(4-methylpiperazin-1-yl)phenyl]amino}pyrido[2,3-d]pyrimidin-5(8H)-one

Example 28A 1-(4-(tert-butylamino)-2-(methylthio)pyrimidin-5-yl)-2-(2,6-dichlorophenyl)ethanone The title compound was prepared as described in Example 8A substituting methanamine with 2-methylpropan-2-amine and the reaction was performed on 200 mg scale (Example 4A). The crude material was purified by flash chromatography (Isco®, Redi-Sep® column 2-45% ethyl acetate/hexane, linear gradient) to obtain the title compound. MS (ESI) m/z 384 (M+H)$^+$.

Example 28B 8-tert-butyl-6-(2,6-dichlorophenyl)-2-(methylthio) pyrido[2,3-d]pyrimidin-5(8H)-one The title compound was prepared as described in Example 8B substituting Example 8A with Example 28A with the exception that the mixture was heated in a Biotage Initiator® microwave reactor at 170° C. for 90 minutes and on a 0.453 mmol scale (Example 28A). The mixture was concentrated and purified directly by flash chromatography (Isco®, Redi-Sep® column, 2 to 45% ethyl acetate/hexane, linear gradient) to afford the title compound. MS (ESI) m/z 394 (M+H)$^+$.

Example 28C 8-tert-butyl-6-(2,6-dichlorophenyl)-2-{[4-(4-methylpiperazin-1-yl)phenyl]amino}pyrido[2,3-d]pyrimidin-5(8H)-one The title compound was prepared as described in Example 5C substituting Example 5B with Example 28B and the reaction was performed on a 0.081 mmol scale (Example 28B). The crude material was purified by Gilson® reverse-phase prep HPLC (5 to 70% acetonitrile/water with 0.1% TFA, linear gradient) to obtain the title compound. $^1$H NMR (400 MHz, dimethylsulfoxide-d$_6$) δ ppm 9.69-9.53 (m, 1H), 9.10 (s, 1H), 7.92 (s, 1H), 7.54 (d, J=8.9, 2H), 7.50 (d, J=7.9, 2H), 7.38 (dd, J=8.7, 7.4, 1H), 7.01 (d, J=9.0, 2H), 3.50-3.21 (m, 8H), 2.88 (s, 3H), 1.75 (s, 9H); MS (ESI): m/z 536.8 (M+H)$^+$.

Example 29

6-(2,6-dichlorophenyl)-8-(4-methoxybenzyl)-2-[(2'-methyl-2',3'-dihydro-1'H-spiro[cyclopropane-1,4'-isoquinolin]-7'-yl)amino]pyrido[2,3-d]pyrimidin-5(8H)-one Example 29A 2-(2,6-dichlorophenyl)-1-(4-(4-methoxybenzylamino)-2-(methylthio)pyrimidin-5-yl)ethanone The title compound was prepared as described in Example 8A substituting methanamine with (4-methoxyphenyl)methanamine. The crude material was purified by flash chromatography (Isco®, Redi-Sep® column 2-45% ethyl acetate/hexane, linear gradient) to obtain the title compound. MS (ESI) m/z 448.1 (M+H)$^+$.

Example 29B 6-(2,6-dichlorophenyl)-8-(4-methoxybenzyl)-2-(methylthio)pyrido[2,3-d]pyrimidin-5(8H)-one The title compound was prepared as described in Example 8B substituting Example 8A with Example 29A with the exception that the mixture was heated in a Biotage Initiator® microwave reactor at 150° C. for 60 minutes. The mixture was concentrated and purified directly by flash chromatography (Isco®, Redi-Sep® column, 2 to 45% ethyl acetate/hexane, linear gradient) to afford the title compound. MS (ESI) m/z 457.6 (M+H)$^+$.

Example 29C 6-(2,6-dichlorophenyl)-8-(4-methoxybenzyl)-2-[(2'-methyl-2',3'-dihydro-1'H-spiro[cyclopropane-1,4'-isoquinolin]-7'-yl)amino]pyrido[2,3-d]pyrimidin-5(8H)-one The title compound was prepared as described in Example 5C substituting Example 5B with Example 29B and substituting 4-(4-methylpiperazin-1-yl)aniline with 2'-methyl-2',3'-dihydro-1'H-spiro[cyclopropane-1,4'-isoquinolin]-7'-amine Purification by flash chromatography (Isco®, Redi-Sep® column, 2-40% CH$_3$OH:H$_2$O (2:1) in ethyl acetate, linear gradient) afforded the title compound. $^1$H NMR (400 MHz, dimethylsulfoxide-d$_6$) δ 9.92 (s, 1H), 9.10 (s, 1H), 8.09 (s, 1H), 7.53-7.47 (m, 4H), 7.40 (dd, J=8.8, 7.3, 1H), 7.25 (d, J=8.7, 2H), 6.87 (d, J=8.7, 2H), 6.75 (d, J=8.3, 1H), 5.41 (s, 2H), 3.98 (s, 2H), 3.72 (s, 3H), 2.95 (s, 2H), 2.65 (s, 3H), 1.07-0.93 (m, 4H); MS (ESI): m/z 598.3 (M+H)$^+$.

Example 30

6-(2,6-dichlorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one Example 29C (46 mg, 0.077 mmol) was dissolved in 1 mL of trifluoroacetic acid. Two drops of concentrated sulfuric acid were added and the mixture was stirred at 60° C. for 24 hours and concentrated in vacuo. The material was purified by reverse-phase prep HPLC (Zorbax C-18, 0.1% TFA/CH$_3$CN/H$_2$O) to afford the title compound. $^1$H NMR (400 MHz, dimethylsulfoxide-d$_6$) δ 9.66 (s, 1H), 9.05 (s, 1H), 7.68 (s, 1H), 7.55-7.46 (m, 4H), 7.38 (dd, J=8.7, 7.4, 1H), 6.65 (d, J=8.5, 1H), 3.63 (s, 2H), 2.95 (s, 2H), 2.35 (s, 3H), 0.94-0.78 (m, 4H); MS (ESI): m/z 478.2 (M+H)$^+$.

Example 31

6-(2,6-dichlorophenyl)-8-ethyl-2-{[4-(4-methylpiperazin-1-yl)phenyl]amino}pyrido[2,3-d]pyrimidin-5(8H)-one Example 31A 2-(2,6-dichlorophenyl)-1-(4-(ethylamino)-2-(methylthio)pyrimidin-5-yl)ethanone The title compound was prepared as described in Example 8A substituting methanamine with ethanamine (2M in THF). The crude material was purified by flash chromatography (Isco®, Redi-Sep® column 2-45% ethyl acetate/hexane, linear gradient) to obtain the title compound. MS (ESI) m/z 356.1 (M+H)$^+$.

Example 31B 6-(2,6-dichlorophenyl)-8-ethyl-2-(methylthio)pyrido[2,3-d]pyrimidin-5(8H)-one The title compound was prepared as described in Example 8B substituting Example 8A with Example 31A with the exception that the mixture was heated in a Biotage Initiator® microwave reactor at 150° C. for 6 hours. The mixture was concentrated and purified directly by flash chromatography (Isco®, Redi-Sep® column, 4 to 45% ethyl acetate/hexane, linear gradient) to afford the title compound. MS (ESI) m/z 366.1 (M+H)$^+$.

Example 31C 6-(2,6-dichlorophenyl)-8-ethyl-2-{[4-(4-methylpiperazin-1-yl)phenyl]amino}pyrido[2,3-d]pyrimidin-5(8H)-one The title compound was prepared as described in Example 5C substituting Example 5B with Example 29B. The material was purified by reverse-phase prep HPLC (Zorbax C-18, 0.1% TFA/CH$_3$CN/H$_2$O) to afford the title compound. $^1$H NMR (400 MHz, dimethylsulfoxide-d$_6$) δ 9.70 (s, 1H), 9.05 (s, 1H), 7.97 (s, 1H), 7.67-7.58 (m, 2H), 7.53-7.47 (m, 2H), 7.39 (dd, J=8.8, 7.4, 1H), 6.97-6.88 (m, 2H), 4.27 (q, J=7.1, 2H), 3.16-3.08 (m, 6H), 2.47-2.43 (m, 2H), 2.23 (s, 3H), 1.37 (t, J=7.1, 3H); MS (ESI): m/z 509.2 (M+H)$^+$.

Example 32

6-(2,6-dichlorophenyl)-8-ethyl-2-[(2'-methyl-2',3'-dihydro-1'H-spiro[cyclopropane-1,4'-isoquinolin]-7'-yl)amino]pyrido[2,3-d]pyrimidin-5(8H)-one The title compound was prepared as described in Example 5C substituting Example 5B with Example 31B and substituting 4-(4-methylpiperazin-1-yl)aniline with 2'-methyl-2',3'-dihydro-1'H-spiro[cyclopropane-1,4'-isoquinolin]-7'-amine. The material was purified by reverse-phase prep HPLC (Zorbax C-18, 0.1% TFA/CH$_3$CN/H$_2$O) to afford the title compound. $^1$H NMR (400 MHz, dimethylsulfoxide-d$_6$) δ

9.83 (s, 1H), 9.08 (s, 1H), 8.01 (s, 1H), 7.57 (d, J=2.0, 1H), 7.53-7.49 (m, 2H), 7.46 (dd, J=8.5, 2.2, 1H), 7.40 (dd, J=8.7, 7.4, 1H), 6.69 (d, J=8.5, 1H), 4.29 (q, J=7.1, 2H), 3.61 (s, 2H), 2.95 (s, 2H), 2.34 (s, 3H), 1.40 (t, J=7.1, 3H), 0.96-0.80 (m, 4H); MS (ESI): m/z 506.2 $(M+H)^+$.

Example 33

6-(2-chloro-6-fluorophenyl)-8-methyl-2-{[4-(4-methylpiperazin-1-yl)phenyl]amino}pyrido[2,3-d]pyrimidin-5(8H)-one

Example 33A 1-(4-chloro-2-(methylthio)pyrimidin-5-yl)-2-(2-chloro-6-fluorophenyl)ethanone The title compound was prepared as described in Example 4A substituting (2,6-dichlorobenzyl)zinc(II) chloride with (2-chloro-6-fluorobenzyl)zinc(II) chloride. Purification by silica gel flash chromatography (Isco®, Redi-Sep® column, 2 to 30% ethyl acetate/hexane, linear gradient) afforded the title compound. MS (ESI) m/z 332 $(M+H)^+$.

Example 33B 2-(2-chloro-6-fluorophenyl)-1-(4-(methylamino)-2-(methylthio)pyrimidin-5-yl)ethanone The title compound was prepared as described in Example 8A substituting Example 4A with Example 33A The crude material was purified by flash chromatography (Isco®, Redi-Sep® column 2-30% ethyl acetate/hexane, linear gradient) to obtain the title compound. MS (ESI) m/z 326.0 $(M+H)^+$.

Example 33C 6-(2-chloro-6-fluorophenyl)-8-methyl-2-(methylthio)pyrido[2,3-d]pyrimidin-5(8H)-one The title compound was prepared as described in Example 8B substituting Example 8A with Example 33B with the exception that the mixture was heated in a Biotage Initiator® microwave reactor at 150° C. for 90 minutes. The mixture was concentrated and purified directly by flash chromatography (Isco®, Redi-Sep® column, 2 to 70% ethyl acetate/hexane, linear gradient) to afford the title compound. MS (ESI) m/z 336.1 $(M+H)^+$.

Example 33D 6-(2-chloro-6-fluorophenyl)-8-methyl-2-{[4-(4-methylpiperazin-1-yl)phenyl]amino}pyrido[2,3-d]pyrimidin-5(8H)-one The title compound was prepared as described in Example 5C substituting Example 5B with Example 33C. Purification by flash chromatography (Isco®, Redi-Sep® column, 0-60% CH$_3$OH:H$_2$O (2:1) in ethyl acetate, linear gradient) afforded the title compound. $^1$H NMR (300 MHz, dimethylsulfoxide-d$_6$) δ 10.13 (s, 1H), 9.05 (s, 1H), 8.15 (s, 1H), 7.69 (d, J=7.5, 2H), 7.51-7.40 (m, 2H), 7.35-7.25 (m, 1H), 6.95 (d, J=9.1, 2H), 3.76 (s, 3H), 3.14-3.07 (m, 4H), 2.49-2.42 (m, 4H), 2.22 (s, 3H); MS (ESI): m/z 479.3 $(M+H)^+$.

Example 34

6-(2-chloro-6-fluorophenyl)-8-methyl-2-[(2'-methyl-2',3'-dihydro-1'H-spiro[cyclopropane-1,4'-isoquinolin]-7'-yl)amino]pyrido[2,3-d]pyrimidin-5(8H)-one The title compound was prepared as described in Example 33D substituting 4-(4-methylpiperazin-1-yl)aniline with 2'-methyl-2',3'-dihydro-1'H-spiro[cyclopropane-1,4'-isoquinolin]-7'-amine. Purification by flash chromatography (Isco®, Redi-Sep® column, 2-60% CH$_3$OH:H$_2$O (2:1) in ethyl acetate, linear gradient) afforded the title compound. $^1$H NMR (300 MHz, dimethylsulfoxide-d$_6$) δ 10.24 (s, 1H), 9.08 (s, 1H), 8.19 (s, 1H), 7.63-7.39 (m, 4H), 7.36-7.25 (m, 1H), 6.71 (d, J=8.6, 1H), 3.78 (s, 3H), 3.60 (s, 2H), 2.45 (s, 2H), 2.33 (s, 3H), 0.97-0.79 (m, 4H); MS (ESI): m/z 476.2 $(M+H)^+$.

Example 35

6-(2-chloro-6-fluorophenyl)-8-(4-methoxybenzyl)-2-{[4-(4-methylpiperazin-1-yl)phenyl]amino}pyrido[2,3-d]pyrimidin-5(8H)-one

Example 35A 2-(2-chloro-6-fluorophenyl)-1-(4-(4-methoxybenzylamino)-2-(methylthio)pyrimidin-5-yl)ethanone The title compound was prepared as described in Example 8A substituting Example 4A with Example 33A and substituting methanamine with (4-methoxyphenyl)methanamine The crude material was purified by flash chromatography (Isco®, Redi-Sep® column 2-30% ethyl acetate/hexane, linear gradient) to obtain the title compound. MS (ESI) m/z 432.5 $(M+H)^+$.

Example 35B 6-(2-chloro-6-fluorophenyl)-8-(4-methoxybenzyl)-2-(methylthio)pyrido[2,3-d]pyrimidin-5(8H)-one The title compound was prepared as described in Example 8B substituting Example 8A with Example 33B with the exception that the mixture was heated in a Biotage Initiator® microwave reactor at 150° C. for 60 minutes. The mixture was concentrated and purified directly by flash chromatography (Isco®, Redi-Sep® column, 2 to 100% ethyl acetate/hexane, linear gradient) to afford the title compound. MS (ESI) m/z 442 $(M+H)^+$.

Example 35C 66-(2-chloro-6-fluorophenyl)-8-(4-methoxybenzyl)-2-{[4-(4-methylpiperazin-1-yl)phenyl]amino}pyrido[2,3-d]pyrimidin-5(8H)-one The title compound was prepared as described in Example 5C substituting Example 5B with Example 35B. Purification by flash chromatography (Isco®, Redi-Sep® column, 2-60% CH$_3$OH:H$_2$O (2:1) in ethyl acetate, linear gradient) afforded the title compound. $^1$H NMR (300 MHz, dimethylsulfoxide-d$_6$) δ 10.11 (s, 1H), 9.05 (s, 1H), 8.32 (s, 1H), 7.58-7.40 (m, 4H), 7.36-7.20 (m, 3H), 6.92 (dt, J=10.5, 7.9, 4H), 5.37 (q, J=14.8, 2H), 3.70 (s, 3H), 3.16-3.06 (m, 4H), 2.48-2.41 (m, 4H), 2.23 (s, 3H); MS (ESI): m/z 585.4 (M+H)$^+$.

Example 36

6-(2-chloro-6-fluorophenyl)-8-(4-methoxybenzyl)-2-[(2'-methyl-2',3'-dihydro-1'H-spiro[cyclopropane-1,4'-isoquinolin]-7'-yl)amino]pyrido[2,3-d]pyrimidin-5(8H)-one The title compound was prepared as described in Example 5C substituting Example 5B with Example 35B and substituting 4-(4-methylpiperazin-1-yl)aniline with 2'-methyl-2',3'-dihydro-1'H-spiro[cyclopropane-1,4'-isoquinolin]-7'-amine. Purification by flash chromatography (Isco®, Redi-Sep® column, 2-50% CH$_3$OH:H$_2$O (2:1) in ethyl acetate, linear gradient) afforded the title compound. $^1$H NMR (300 MHz, dimethylsulfoxide-d$_6$) δ 10.22 (s, 1H), 9.10 (s, 1H), 8.33 (s, 1H), 7.51-7.20 (m, 7H), 6.95-6.84 (m, 2H), 6.67 (d, J=8.6, 1H), 5.40 (q, J=15.1, 2H), 3.70 (s, 3H), 3.42 (s, 2H), 2.42 (s, 2H), 2.28 (s, 3H), 0.95-0.79 (m, 4H); MS (ESI): m/z 582.3 (M+H)$^+$.

Example 37

6-(2-chloro-6-fluorophenyl)-8-cyclopropyl-2-{[4-(4-methylpiperazin-1-yl)phenyl]amino}pyrido[2,3-d]pyrimidin-5(8H)-one Example 37A 2-(2-chloro-6-fluorophenyl)-1-(4-(cyclopropylamino)-2-(methylthio)pyrimidin-5-yl)ethanone The title compound was prepared as described in Example 8A substituting Example 4A with Example 33A and substituting methanamine with cyclopropanamine. The crude material was purified by flash chromatography (Isco®, Redi-Sep® column 2-30% ethyl acetate/hexane, linear gradient) to obtain the title compound. MS (ESI) m/z 352 (M+H)$^+$.

Example 37B 6-(2-chloro-6-fluorophenyl)-8-cyclopropyl-2-(methylthio)pyrido[2,3-d]pyrimidin-5(8H)-one The title compound was prepared as described in Example 8B substituting Example 8A with Example 37A with the exception that the mixture was heated in a Biotage Initiator® microwave reactor at 140° C. for 60 minutes. The mixture was concentrated and purified directly by flash chromatography (Isco®, Redi-Sep® column, 2 to 100% ethyl acetate/hexane, linear gradient) to afford the title compound. MS (ESI) m/z 362 (M+H)$^+$.

Example 37C 6-(2-chloro-6-fluorophenyl)-8-cyclopropyl-2-{[4-(4-methylpiperazin-1-yl)phenyl]amino}pyrido[2,3-d]pyrimidin-5(8H)-one The title compound was prepared as described in Example 5C substituting Example 5B with Example 37B. Purification by flash chromatography (Isco®, Redi-Sep® column, 2-60% CH$_3$OH:H$_2$O(2:1) in ethyl acetate, linear gradient) afforded the title compound. $^1$H NMR (300 MHz, dimethylsulfoxide-d$_6$) δ 10.18 (s, 1H), 9.04 (s, 1H), 8.05 (s, 1H), 7.86 (d, J=7.9, 2H), 7.54-7.37 (m, 2H), 7.33-7.23 (m, 1H), 7.02-6.91 (m, 2H), 3.61-3.50 (m, 1H), 3.15-3.06 (m, 4H), 2.48-2.41 (m, 4H), 2.22 (s, 3H), 1.22-1.02 (m, 4H); MS (ESI): m/z 505.2 (M+H)$^+$.

Example 38

6-(2-chloro-6-fluorophenyl)-8-cyclopropyl-2-[(2'-methyl-2',3'-dihydro-1'H-spiro[cyclopropane-1,4'-isoquinolin]-7'-yl)amino]pyrido[2,3-d]pyrimidin-5(8H)-one The title compound was prepared as described in Example 5C substituting Example 5B with Example 37B and substituting 4-(4-methylpiperazin-1-yl)aniline with 2'-methyl-2',3'-dihydro-1'H-spiro[cyclopropane-1,4'-isoquinolin]-7'-amine. Purification by flash chromatography (Isco®, Redi-Sep® column, 2-50% CH$_3$OH:H$_2$O(2:1) in ethyl acetate, linear gradient) afforded the title compound. $^1$H NMR (300 MHz, dimethylsulfoxide-d$_6$) δ 10.26 (s, 1H), 9.07 (s, 1H), 8.09 (s, 1H), 7.78-7.67 (m, 2H), 7.51-7.39 (m, 2H), 7.33-7.23 (m, 1H), 6.72 (d, J=9.3, 1H), 3.67-3.53 (m, 3H), 2.45 (s, 2H), 2.32 (s, 3H), 1.22-1.03 (m, 4H), 0.95-0.78 (m, 4H); MS (ESI): m/z 502.3 (M+H)$^+$.

Example 39

6-(2-chloro-6-fluorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one The title compound was prepared as described in Example 30 substituting Example 29C with Example 36. Purification by flash chromatography (Isco®, Redi-Sep® column, 2-50% CH$_3$OH:H$_2$O (2:1) in ethyl acetate, linear gradient) afforded the title compound. $^1$H NMR (300 MHz, dimethylsulfoxide-d$_6$) δ 12.18 (s, 1H), 10.11 (s, 1H), 9.07 (s, 1H), 7.93 (d, J=5.0, 1H), 7.67 (s, 1H), 7.60-7.51 (m, 1H), 7.49-7.38 (m, 2H), 7.33-7.23 (m, 1H), 6.70 (d, J=8.6, 1H), 3.87-3.63 (m, 2H), 2.68-2.54 (m, 2H), 2.43 (s, 3H), 1.02-0.84 (m, 4H); MS (ESI): m/z 462.4 (M+H)$^+$.

Example 40

6-(2-chloro-6-fluorophenyl)-2-{[4-(4-methylpiperazin-1-yl)phenyl]amino}pyrido[2,3-d]pyrimidin-5(8H)-one The title compound was prepared as described in Example 30 substituting Example 29C with Example 35C. Purification by flash chromatography (Isco®, Redi-Sep® column, 2-50% CH$_3$OH:H$_2$O(2:1) in ethyl acetate, linear gradient) afforded the title compound. $^1$H NMR (300 MHz, dimethylsulfoxide-d$_6$) δ 9.92 (s, 1H), 9.03 (s, 1H), 7.84 (s, 1H), 7.68 (d, J=8.9, 2H), 7.48-7.37 (m, 2H), 7.31-7.22 (m, 1H), 6.92 (d, J=9.1, 2H), 3.13-3.06 (m, 4H), 2.47-2.41 (m, J=4.8, 4H), 2.22 (s, 3H); MS (ESI): m/z 465.2 (M+H)$^+$.

Example 41

6-(2,6-dichlorophenyl)-2-{[2-(dimethylamino)-2,3-dihydro-1H-inden-5-yl]amino}pyrido[2,3-d]pyrimidin-5(8H)-one Example 41A 6-(2,6-dichlorophenyl)-2-(2-(dimethylamino)-2,3-dihydro-1H-inden-5-ylamino)-8-(4-methoxybenzyl)pyrido[2,3-d]pyrimidin-5(8H)-one The title compound was prepared as described in Example 29C substituting 2'-methyl-2',3'-dihydro-1'H-spiro[cyclopropane-1,4'-isoquinolin]-7'-amine with $N^2,N^2$-dimethyl-2,3-dihydro-1H-indene-2,5-diamine. The crude material was carried through the next step without further purification. MS (ESI) m/z 586.3 (M+H)$^+$.

Example 41B 6-(2,6-dichlorophenyl)-2-{[2-(dimethylamino)-2,3-dihydro-1H-inden-5-yl]amino}pyrido[2,3-d]pyrimidin-5(8H)-one The title compound was prepared as described in Example 30 substituting Example 29C with Example 41A. Purification by reverse-phase prep HPLC (Zorbax C-18, 0.1% ammonium acetate/CH$_3$CN/H$_2$O) afforded the title compound. $^1$H NMR (400 MHz, dimethylsulfoxide-d$_6$) δ 9.69 (s, 1H), 9.05 (s, 1H), 7.70-7.65 (m, 2H), 7.57-7.52 (m, 1H), 7.50 (d, J=8.1, 2H), 7.38 (dd, J=8.6, 7.4, 1H), 7.13 (d, J=8.1, 1H), 2.88-2.73 (m, 4H), 2.26 (s, 6H); MS (ESI): m/z 466.3 (M+H)$^+$.

Example 42

6-(2,6-dichlorophenyl)-2-[(2,4,4-trimethyl-1,2,3,4-tetrahydroisoquinolin-7-yl)amino]pyrido[2,3-d]pyrimidin-5(8H)-one

Example 42A 6-(2,6-dichlorophenyl)-8-(4-methoxybenzyl)-2-(2,4,4-trimethyl-1,2,3,4-tetrahydroisoquinolin-7-ylamino)pyrido[2,3-d]pyrimidin-5(8H)-one The title compound was prepared as described in Example 29C substituting 2'-methyl-2',3'-dihydro-1'H-spiro[cyclopropane-1,4'-isoquinolin]-7'-amine with 2,4,4-trimethyl-1,2,3,4-tetrahydroisoquinolin-7-amine. The crude material was carried through the next step without further purification. MS (ESI) m/z 599.8 (M+H)$^+$.

Example 42B 6-(2,6-dichlorophenyl)-2-[(2,4,4-trimethyl-1,2,3,4-tetrahydroisoquinolin-7-yl)amino]pyrido[2,3-d]pyrimidin-5(8H)-one The title compound was prepared as described in Example 30 substituting Example 29C with Example 42A. Purification by reverse-phase prep HPLC (Zorbax C-18, 0.1% ammonium acetate/CH$_3$CN/H$_2$O) afforded the title compound. $^1$H NMR (400 MHz, dimethylsulfoxide-d$_6$) δ 11.89 (s, 1H), 9.91 (s, 1H), 9.09 (s, 1H), 7.82-7.66 (m, 3H), 7.53-7.47 (m, 2H), 7.45-7.34 (m, 2H), 4.36 (s, 2H), 3.34 (s, 2H), 2.98 (s, 3H), 1.39 (s, 6H); MS (ESI): m/z 480.2 (M+H)$^+$.

Example 43

6-(2,6-dichlorophenyl)-2-(2',3'-dihydro-1'H-spiro[cyclopropane-1,4'-isoquinolin]-7'-ylamino)pyrido[2,3-d]pyrimidin-5(8H)-one

Example 43A 6-(2,6-dichlorophenyl)-2-(2',3'-dihydro-1'H-spiro[cyclopropane-1,4'-isoquinoline]-7'-ylamino)-8-(4-methoxybenzyl)pyrido[2,3-d]pyrimidin-5(8H)-one The title compound was prepared as described in Example 29C substituting 2'-methyl-2',3'-dihydro-1'H-spiro[cyclopropane-1,4'-isoquinolin]-7'-amine with 2',3'-dihydro-1'H-spiro[cyclopropane-1,4'-isoquinolin]-7'-amine. The crude material was carried through the next step without further purification. MS (ESI) m/z 584.3 (M+H)$^+$.

Example 43B 6-(2,6-dichlorophenyl)-2-(2',3'-dihydro-1'H-spiro[cyclopropane-1,4'-isoquinolin]-7'-ylamino)pyrido[2,3-d]pyrimidin-5(8H)-one The title compound was prepared as described in Example 30 substituting Example 29C with Example 43A. Purification by reverse-phase prep HPLC (Zorbax C-18, 0.1% TFA/CH$_3$CN/H$_2$O) afforded the title compound. $^1$H NMR (400 MHz, dimethylsulfoxide-d$_6$) δ 11.82 (s, 1H), 9.88 (s, 1H), 9.17 (brs, 2H), 9.08 (s, 1H), 7.84-7.71 (m, 2H), 7.65 (dd, J=8.6, 2.0, 1H), 7.50 (d, J=7.9, 2H), 7.39 (dd, J=8.7, 7.4, 1H), 6.82 (d, J=8.6, 1H), 4.39 (s, 2H), 3.27 (s, 2H), 1.15-1.05 (m, 4H); MS (ESI): m/z 464.2 (M+H)$^+$.

Example 44

6-(2,6-dichlorophenyl)-2-({4-[4-(dimethylamino)piperidin-1-yl]phenyl}amino)-8-methylpyrido[2,3-d]pyrimidin-5(8H)-one The title compound was prepared as described in Example 8C substituting 4-(4-methylpiperazin-1-yl)aniline with 1-(4-aminophenyl)-N,N-dimethylpiperidin-4-amine. Purification by reverse-phase prep HPLC (Zorbax C-18, 0.1% TFA/CH$_3$CN/H$_2$O) afforded the title compound. $^1$H NMR (400 MHz, dimethylsulfoxide-d$_6$) δ 9.76 (s, 1H), 9.05 (s, 1H), 7.96 (s, 1H), 7.67 (d, J=9.0, 2H), 7.54-7.49 (m, 2H), 7.40 (dd, J=8.7, 7.4, 1H), 6.97 (d, J=8.9, 2H), 3.83-3.77 (m, 2H), 3.36-3.26 (m, 2H), 2.80 (s, 6H), 2.79-2.70 (m, 2H), 2.13-2.05 (m, 2H), 1.82-1.69 (m, 2H); MS (ESI): m/z 523.2 (M+H)$^+$.

Example 45

2-amino-6-(2,6-dichlorophenyl)-8-methylpyrido[2,3-d]pyrimidin-5(8H)-one

The title compound was prepared as described in Example 8C substituting 4-(4-methylpiperazin-1-yl)aniline with ammonia (7M in CH$_3$OH). Purification by reverse-phase prep HPLC (Zorbax C-18, 0.1% TFA/CH$_3$CN/H$_2$O) afforded the title compound. $^1$H NMR (300 MHz, dimethylsulfoxide-d$_6$) δ 8.94 (s, 1H), 8.03 (s, 1H), 7.58-7.48 (m, J=11.7, 4.1, 4H), 7.42 (dd, J=8.9, 7.2, 2H), 3.67 (s, 3H); MS (ESI): m/z 321.0 (M+H)$^+$.

Example 46

6-(2,6-dichlorophenyl)-8-methyl-2-(1,2,3,4-tetrahydroisoquinolin-6-ylamino)pyrido[2,3-d]pyrimidin-5(8H)-one The title compound was prepared as described in Example 8C substituting 4-(4-methylpiperazin-1-yl)aniline with tert-butyl 6-amino-3,4-dihydroisoquinoline-2(1H)-carboxylate. Purification by silica gel flash chromatography (Isco®, Redi-Sep® column, 2-100% ethyl acetate/hexane, linear gradient) afforded the Boc protected intermediate. To the product was added 0.5 mL of CH$_2$Cl$_2$, 0.5 mL of CH$_3$OH and 2 mL of ethyl acetate. 5 mL of 2 molar HCl in diethyl ether was added and the mixture stirred at 50° C. for 3 hours. The solid was then filtered and washed with diethyl ether to yield the title compound as an HCl salt. $^1$H NMR (300 MHz, dimethylsulfoxide-d$_6$) δ 10.40 (s, 1H), 9.31 (brs, 2H), 9.12 (s, 1H), 8.18 (s, 1H), 7.80 (s, 1H), 7.67 (dd, J=8.5, 2.1, 1H), 7.60-7.54 (m, 2H), 7.45 (dd, J=9.0, 7.2, 1H), 7.21 (d, J=8.5, 1H), 4.26-4.20 (m, 2H), 3.80 (s, 3H), 3.43-3.33 (m, 2H), 3.09-2.97 (m, 2H); MS (ESI): m/z 452.3 (M+H)$^+$.

Example 47

6-(2,6-dichlorophenyl)-2-[(4,4-dimethyl-1,2,3,4-tetrahydroisoquinolin-7-yl)amino]-8-methylpyrido[2,3-d]pyrimidin-5(8H)-one The title compound was prepared as described in Example 8C substituting 4-(4-methylpiperazin-1-yl)aniline with tert-butyl 7-amino-4,4-dimethyl-3,4-dihydroisoquinoline-2(1H)-carboxylate. Purification by silica gel flash chromatography (Isco®, Redi-Sep® column, 2-100% ethyl acetate/hexane, linear gradient) afforded the Boc protected intermediate. The product was dissolved with 0.5 mL of CH$_2$Cl$_2$, 0.5 mL of CH$_3$OH and 2 mL of ethyl acetate. 4 mL 2 molar HCl in diethyl ether was added and the mixture stirred at 50° C. for 3 hours. The solid was then filtered and washed with diethyl ether to yield the title compound as an HCl salt. $^1$H NMR (300 MHz, dimethylsulfoxide-d$_6$) δ 10.40 (s, 1H), 9.12 (s, 1H), 9.02 (brs, 2H), 8.18 (s, 1H), 7.79-7.67 (m, 2H), 7.61-7.54 (m, 2H), 7.51-7.40 (m, 2H), 4.34-4.25 (m, 2H), 3.81 (s, 3H), 3.28-3.20 (m, 2H), 1.36 (s, 6H); MS (ESI): m/z 480.1 (M+H)$^+$.

Example 48

6-(2,6-dichlorophenyl)-8-methyl-2-{[4-(morpholin-4-yl)phenyl]amino}pyrido[2,3-d]pyrimidin-5(8H)-one The title compound was prepared as described in Example 8C substituting 4-(4-methylpiperazin-1-yl)aniline with 4-morpholinoaniline. Purification by reverse-phase prep HPLC (Zorbax C-18, 0.1% TFA/CH$_3$CN/H$_2$O) afforded the title compound. $^1$H NMR (300 MHz, dimethylsulfoxide-d$_6$) δ 10.18 (s, 1H), 9.06 (s, 1H), 8.12 (s, 1H), 7.73 (brd, J=8.4, 2H), 7.61-7.50 (m, 2H), 7.43 (dd, J=9.0, 7.2, 1H), 7.01 (d, J=9.1, 2H), 3.83-3.68 (m, 7H), 3.15-3.05 (m, 4H); MS (ESI): m/z 482.2 (M+H)$^+$.

Example 49

6-(2,6-dichlorophenyl)-2-(2,3-dihydro-1H-isoindol-5-ylamino)-8-methylpyrido[2,3-d]pyrimidin-5(8H)-one The title compound was prepared as described in Example 8C substituting 4-(4-methylpiperazin-1-yl)aniline with tert-butyl 5-aminoisoindoline-2-carboxylate. Purification by silica gel flash chromatography (Isco®, Redi-Sep® column, 2-100% ethyl acetate/hexane, linear gradient) afforded the Boc protected intermediate. The product was dissolved with 0.5 mL of CH$_2$Cl$_2$, 0.5 mL of CH$_3$OH and 2 mL of ethyl acetate. 4 mL 2 molar HCl in diethyl ether was added and the mixture stirred at 50° C. for 3 hours. The solid was then filtered and washed with diethyl ether to yield the title compound as an HCl salt. $^1$H NMR (300 MHz, dimethylsulfoxide-d$_6$) δ 10.51 (s, 1H), 9.80 (brm, 2H), 9.13 (s, 1H), 8.19 (s, 1H), 7.95 (s, 1H), 7.78 (dd, J=8.4, 1.3, 1H), 7.61-7.53 (m, 2H), 7.49-7.35 (m, 2H), 4.56-4.44 (m, 4H), 3.80 (s, 3H); MS (ESI): m/z 438.2 (M+H)$^+$.

Example 50

6-(2,6-dichlorophenyl)-8-methyl-2-{[4-(1-methylpiperidin-4-yl)phenyl]amino}pyrido[2,3-d]pyrimidin-5(8H)-one The title compound was prepared as described in Example 8C substituting 4-(4-methylpiperazin-1-yl)aniline with 4-(1-methylpiperidin-4-yl)aniline. Purification by reverse-phase prep HPLC (Zorbax C-18, 0.1% TFA/CH$_3$CN/H$_2$O) afforded the title compound. $^1$H NMR (300 MHz, dimethylsulfoxide-d$_6$) δ 10.28 (s, 1H), 9.09 (s, 1H), 8.14 (s, 1H), 7.78 (d, J=8.3, 2H), 7.59-7.54 (m, 2H), 7.44 (dd, J=8.9, 7.2, 1H), 7.23 (d, J=8.6, 2H), 3.79 (s, 3H), 2.87 (d, J=11.3, 2H), 2.47-2.36 (m, 1H), 2.20 (s, 3H), 2.02-1.92 (m, 2H), 1.77-1.56 (m, 4H); MS (ESI): m/z 494.3 (M+H)$^+$.

Example 51

6-(2,6-dichlorophenyl)-8-methyl-2-(1,2,3,4-tetrahydroisoquinolin-7-ylamino)pyrido[2,3-d]pyrimidin-5(8H)-one The title compound was prepared as described in Example 8C substituting 4-(4-methylpiperazin-1-yl)aniline with tert-butyl 7-amino-3,4-dihydroisoquinoline-2(1H)-carboxylate. Purification by silica gel flash chromatography (Isco®, Redi-Sep® column, 2-100% ethyl acetate/hexane, linear gradient) afforded the Boc protected intermediate. To the product was added 0.5 mL of CH$_2$Cl$_2$, 0.5 mL of CH$_3$OH and 2 mL of ethyl acetate. 4 mL of 2 molar HCl in diethyl ether was added and the mixture stirred at 50° C. for 3 hours. The solid was then filtered and washed with diethyl ether to yield the title compound as an HCl salt. $^1$H NMR (300 MHz, dimethylsulfoxide-d$_6$) δ 10.40 (s, 1H), 9.31 (s, 2H), 9.12 (s, 1H), 8.19 (s, 1H), 7.80 (brs, 1H), 7.64 (dd, J=8.4, 2.1, 1H), 7.60-7.54 (m, 2H), 7.45 (dd, J=8.9, 7.2, 1H), 7.22 (d, J=8.4, 1H), 4.32-4.24 (m, 2H), 3.80 (s, 3H), 3.43-3.33 (m, 2H), 3.03-2.94 (m, 2H); MS (ESI): m/z 452.1 (M+H)$^+$.

Example 52

6-(2,6-dichlorophenyl)-8-methyl-2-[(2-methyl-1,2,3,4-tetrahydroisoquinolin-7-yl)amino]pyrido[2,3-d]pyrimidin-5(8H)-one To a stirring suspension of Example 51 (33 mg, 0.073 mmol, HCl salt) in dichloroethane (730 μl) was added formaldehyde (32.6 μl, 0.438 mmol). The reaction mixture was stirred at ambient temperature for 30 minutes then sodium triacetoxyborohydride (30.9 mg, 0.146 mmol) was added and the mixture was stirred at ambient temperature for 3 hours. The mixture was dissolved in 20 mL of ethyl acetate then washed with 20 mL of saturated aqueous sodium bicarbonate, 20 mL of saturated aqueous brine, dried over anhydrous magnesium sulfate, filtered and concentrated. Purification by silica gel flash chromatography (Isco®, Redi-Sep® column, 2-70% CH$_3$OH:H$_2$O (2:1) in ethyl acetate, linear gradient) afforded the title compound. $^1$H NMR (300 MHz, dimethylsulfoxide-d$_6$) δ 10.23 (s, 1H), 9.09 (s, 1H), 8.15 (s, 1H), 7.65-7.51 (m, 4H), 7.44 (dd, J=8.9, 7.2, 1H), 7.09 (d, J=8.3, 1H), 3.78 (s, 3H), 3.51-3.47 (m, 2H), 2.83-2.75 (m, 2H), 2.62-2.55 (m, 2H), 2.35 (s, 3H); MS (ESI): m/z 466.1 (M+H)+.

Example 53

6-(2,6-dichlorophenyl)-8-methyl-2-[(2-methyl-2,3-dihydro-1H-isoindol-5-yl)amino]pyrido[2,3-d]pyrimidin-5(8H)-one The title compound was prepared as described in Example 52 substituting Example 51 with Example 49. Purification by silica gel flash chromatography (Isco®, Redi-Sep® column, 2-90% CH$_3$OH:H$_2$O (2:1) in ethyl acetate, linear gradient) afforded the title compound. $^1$H NMR (300 MHz, dimethylsulfoxide-d$_6$) δ 10.30 (s, 1H), 9.10 (s, 1H), 8.14 (s, 1H), 7.76 (s, 1H), 7.65-7.54 (m, 3H), 7.44 (dd, J=8.9, 7.2, 1H), 7.20 (d, J=8.2, 1H), 3.86-3.74 (m, 7H), 2.48 (s, 3H); MS (ESI): m/z 452.1 (M+H)+.

Example 54

6-(2,6-dichlorophenyl)-8-methyl-2-[(2-methyl-1,2,3,4-tetrahydroisoquinolin-6-yl)amino]pyrido[2,3-d]pyrimidin-5(8H)-one The title compound was prepared as described in Example 52 substituting Example 51 with Example 46. Purification by silica gel flash chromatography (Isco®, Redi-Sep® column, 2-70% CH$_3$OH:H$_2$O (2:1) in ethyl acetate, linear gradient) afforded the title compound. $^1$H NMR (300 MHz, dimethylsulfoxide-d$_6$) δ 10.23 (s, 1H), 9.09 (s, 1H), 8.15 (s, 1H), 7.66 (s, 1H), 7.61-7.53 (m, 3H), 7.44 (dd, J=8.9, 7.2, 1H), 7.03 (d, J=8.4, 1H), 3.79 (s, 3H), 3.45 (s, 2H), 2.87-2.80 (m, 2H), 2.63-2.55 (m, 2H), 2.34 (s, 3H); MS (ESI): m/z 466.4 (M+H)+.

Example 55

6-(2,6-dichlorophenyl)-8-methyl-2-{[2-(pyrrolidin-1-yl)-2,3-dihydro-1H-inden-5-yl]amino}pyrido[2,3-d]pyrimidin-5(8H)-one

Example 55A 1-(2,3-dihydro-1H-inden-2-yl)pyrrolidine

To a solution of 1H-inden-2(3H)-one (6 g, 45.4 mmol) in 100 mL of methanol were added pyrrolidine (7.51 ml, 91 mmol), sodium cyanoborohydride (5.71 g, 91 mmol), and acetic acid (5.20 ml, 91 mmol). The reaction mixture was stirred overnight then concentrated. The crude residue was dissolved in 400 mL of ethyl acetate and washed with aqueous sodium bicarbonate (2×400 mL) and saturated aqueous brine (1×200 mL), dried over magnesium sulfate, filtered and concentrated. Recrystallization in ethyl acetate/hexane afforded the title compound. MS (ESI) m/z 188 (M+H)+.

Example 55B 1-(5-nitro-2,3-dihydro-1H-inden-2-yl)pyrrolidine

To a solution of Example 55A (8.38 g, 44.7 mmol) in TFA (320 ml, 4154 mmol) was added concentrated nitric acid (2.86 ml, 44.7 mmol) dropwise at 0° C. The mixture was stirred at 0-15° C. for 5 hours. The mixture was next concentrated then dissolved in 200 mL of ethyl acetate and the organic solution was poured into a separatory funnel and washed with saturated aqueous sodium bicarbonate (2×150 mL) and saturated aqueous brine (1×100 mL), dried over magnesium sulfate, filtered and concentrated. The crude was recrystallized in ethyl acetate/hexane mixture to give the title compound. MS (ESI) m/z 233.1 (M+H)+.

Example 55C 2-(pyrrolidin-1-yl)-2,3-dihydro-1H-inden-5-amine

To a solution of Example 55B (7.25 g, 31.2 mmol) in 156 mL of methanol was added palladium on carbon (10% wt) (7.25 g, 6.81 mmol). The reaction mixture was evacuated and backfilled with nitrogen three times then evacuated and backfilled with hydrogen. The mixture was then allowed to stirred under H$_2$ (1 atm, balloon) at ambient temperature overnight. The mixture was filtered through a celite pad then concentrated and the crude product was recrystallized in ethyl acetate/hexane mixture to obtain the title compound. MS (ESI) m/z 203.1 (M+H)+.

Example 55D 6-(2,6-dichlorophenyl)-8-methyl-2-{[2-(pyrrolidin-1-yl)-2,3-dihydro-1H-inden-5-yl]amino}pyrido[2,3-d]pyrimidin-5(8H)-one The title compound was prepared as described in Example 8C substituting 4-(4-methylpiperazin-1-yl)aniline with Example 55C. Purification by reverse-phase prep HPLC (Zorbax C-18, 0.1% TFA/CH$_3$CN/H$_2$O) afforded the title compound. $^1$H NMR (300 MHz, dimethylsulfoxide-d$_6$) δ 10.35 (s, 1H), 9.97 (brs, 1H), 9.11 (s, 1H), 8.16 (s, 1H), 7.81 (s, 1H), 7.68 (d, J=8.0, 1H), 7.61-7.54 (m, 2H), 7.44 (dd, J=9.0, 7.2, 1H), 7.26 (d, J=8.3, 1H), 4.20-4.05 (m, 1H), 3.79 (s, 3H), 3.42-3.02 (m, 8H), 2.15-1.82 (m, 4H); MS (ESI): m/z 466.4 (M+H)+.

Example 56

5-{[6-(2,6-dichlorophenyl)-8-methyl-5-oxo-5,8-dihydropyrido[2,3-d]pyrimidin-2-yl]amino}-1H-isoindole-1,3(2H)-dione The title compound was prepared as described in Example 8C substituting 4-(4-methylpiperazin-1-yl)aniline with 5-aminoisoindoline-1,3-dione. Purification by reverse-phase prep HPLC (Zorbax C-18, 0.1% TFA/CH$_3$CN/H$_2$O) afforded the title compound. $^1$H NMR (300 MHz, dimethylsulfoxide-d$_6$) δ 11.20 (s, 1H), 11.01 (s, 1H), 9.22 (s, 1H), 8.50-8.41 (m, 1H), 8.27-8.15 (m, 2H), 7.83 (d, J=8.3, 1H), 7.64-7.54 (m, 2H), 7.45 (dd, J=8.9, 7.2, 1H), 3.86 (s, 3H); MS (ESI): m/z 466.3 (M+H)+.

Example 57

6-(2,6-dichlorophenyl)-8-methyl-2-{[2-(4-methylpiperazin-1-yl)-2,3-dihydro-1H-inden-5-yl]amino}pyrido[2,3-d]pyrimidin-5(8H)-one

Example 57A 1-(2,3-dihydro-1H-inden-2-yl)-4-methylpiperazine

The title compound was obtained as described in Example 55A substituting pyrrolidine with 1-methylpiperazine to give the title compound. The crude material obtained was carried through the next step without purification. MS (ESI) m/z 217.1 (M+H)+.

Example 57B 1-methyl-4-(5-nitro-2,3-dihydro-1H-inden-2-yl)piperazine

The title compound was obtained as described in Example 55B substituting Example 55A with Example 57A. Purification by silica gel flash chromatography (Isco®, Redi-Sep® column, 2-40% $CH_3OH:H_2O(2:1)$ in ethyl acetate, linear gradient) afforded the title compound. MS (ESI) m/z 262.2 (M+H)+.

Example 57C 2-(4-methylpiperazin-1-yl)-2,3-dihydro-1H-inden-5-amine

The title compound was obtained as described in Example 55C substituting Example 55B with Example 57B to give the crude title compound which was carried through the next step without purification. MS (ESI) m/z 232.1 (M+H)+.

Example 57D 6-(2,6-dichlorophenyl)-8-methyl-2-{[2-(4-methylpiperazin-1-yl)-2,3-dihydro-1H-inden-5-yl]amino}pyrido[2,3-d]pyrimidin-5(8H)-one The title compound was prepared as described in Example 8C substituting 4-(4-methylpiperazin-1-yl)aniline with Example 57C. Purification by reverse-phase prep HPLC (Zorbax C-18, 0.1% $TFA/CH_3CN/H_2O$) afforded the title compound. $^1$H NMR (300 MHz, dimethylsulfoxide-$d_6$) δ 10.30 (s, 1H), 9.10 (s, 1H), 8.15 (s, 1H), 7.77 (s, 1H), 7.64 (d, J=8.0, 1H), 7.59-7.54 (m, 2H), 7.44 (dd, J=8.9, 7.2, 1H), 7.22 (d, J=8.2, 1H), 3.79 (s, 3H), 3.69-3.59 (m, 1H), 3.51-2.84 (m, 12H), 2.80 (s, 3H); MS (ESI): m/z 535.3 (M+H)+.

Example 58

6-(2,6-dichlorophenyl)-8-methyl-2-(4,5,6,7-tetrahydrothieno[3,2-c]pyridin-2-ylamino)pyrido[2,3-d]pyrimidin-5(8H)-one Example 58A tert-butyl 2-amino-6,7-dihydrothieno[3,2-c]pyridine-5(4H)-carboxylate To a solution of tert-butyl 6,7-dihydrothieno[3,2-c]pyridine-5(4H)-carboxylate (200 mg, 0.836 mmol) in TFA (6.89 ml, 89 mmol) was added concentrated nitric acid (0.053 ml, 0.836 mmol) dropwise at 0° C. The mixture was next concentrated then dissolved in 20 mL of ethyl acetate and di-tert-butyl dicarbonate (0.194 ml, 0.836 mmol) was added. The mixture was stirred at ambient for 60 minutes then the mixture was poured into a separatory funnel and washed with 20 mL of saturated aqueous sodium bicarbonate and 20 mL of saturated aqueous brine, dried over magnesium sulfate, filtered and concentrated. Purification by silica gel flash chromatography (Isco®, Redi-Sep® column, 2-50% ethyl acetate/hexane, linear gradient) afforded tert-butyl 2-nitro-6,7-dihydrothieno[3,2-c]pyridine-5(4H)-carboxylate (107 mg, 0.376 mmol). To this intermediate was added palladium on carbon (10% wt) (89 mg, 0.836 mmol) and the flask was capped with septa. The flask was evacuated and backfilled with nitrogen and 10 mL of methanol were added. The mixture was evacuated and backfilled with nitrogen 3 times then evacuated and backfilled with hydrogen. The mixture was stirred under hydrogen (1 atm, balloon) for 3 hours. The mixture was filtered through a celite pad and the filter cake washed with 20 mL of dichloromethane. The mixture was concentrated and the crude material was purified on silica gel flash chromatography (Isco®, Redi-Sep® column, 0-100% ethyl acetate/hexane, linear gradient) to obtain the title compound. MS (ESI) m/z 255.1 (M+H)+.

Example 58B 6-(2,6-dichlorophenyl)-8-methyl-2-(4,5,6,7-tetrahydrothieno[3,2-c]pyridin-2-ylamino)pyrido[2,3-d]pyrimidin-5(8H)-one The title compound was prepared as described in Example 8C substituting 4-(4-methylpiperazin-1-yl)aniline with Example 58A. Purification by silica gel flash chromatography (Isco®, Redi-Sep® column, 2-100% ethyl acetate/hexane, linear gradient) afforded the Boc protected intermediate. To the product was added 0.5 mL of $CH_2Cl_2$, 0.5 mL of $CH_3OH$ and 2 mL of ethyl acetate. 4 mL of 2 molar HCl in diethyl ether was added and the mixture stirred at 50° C. for 3 hours. The solid was filtered and washed with diethyl ether to give the HCl salt which was further purified by reverse-phase prep HPLC (Zorbax C-18, 0.1% $TFA/CH_3CN/H_2O$) to afford the title compound. $^1$H NMR (300 MHz, dimethylsulfoxide-$d_6$) δ 11.60 (s, 1H), 9.12 (s, 1H), 8.98 (brs, 2H), 8.17 (s, 1H), 7.62-7.53 (m, 2H), 7.45 (dd, J=9.0, 7.2, 1H), 6.64 (s, 1H), 4.16 (s, 2H), 3.89 (s, 3H), 3.47-3.39 (m, 2H), 3.04-2.93 (m, 2H); MS (ESI): m/z 460.1 (M+H)+.

Example 59

6-(2,6-dichlorophenyl)-8-methyl-2-{[2-(4-methylpiperazin-1-yl)pyrimidin-5-yl]amino}pyrido[2,3-d]pyrimidin-5(8H)-one The title compound was prepared as described in Example 8C substituting 4-(4-methylpiperazin-1-yl)aniline with 2-(4-methylpiperazin-1-yl)pyrimidin-5-amine. Purification by flash chromatography (Isco®, Redi-Sep® column, 2-50% $CH_3OH:H_2O$ (2:1) in ethyl acetate with 2% triethylamine, linear gradient) followed by recrystallization in ethyl acetate/hexane mixture afforded the title compound. $^1$H NMR (300 MHz, dimethylsulfoxide-$d_6$) δ 10.16 (s, 1H), 9.07 (s, 1H), 8.79 (brs, 2H), 8.13 (s, 1H), 7.61-7.52 (m, 2H), 7.43 (dd, J=8.9, 7.2, 1H), 3.76-3.68 (m, 7H), 2.41-2.33 (m, 4H), 2.22 (s, 3H); MS (ESI): m/z 497.3 (M+H)+.

Example 60

6-(2,6-dichlorophenyl)-8-methyl-2-[(1,1,2-trimethyl-2,3-dihydro-1H-isoindol-5-yl)amino]pyrido[2,3-d]pyrimidin-5(8H)-one The title compound was prepared as described in Example 8C substituting 4-(4-methylpiperazin-1-yl)aniline with 1,1,2-trimethylisoindolin-5-amine. Purification by reverse-phase prep HPLC (Zorbax C-18, 0.1% ammonium acetate/$CH_3CN/H_2O$) afforded the title compound. $^1$H NMR (400 MHz, dimethylsulfoxide-$d_6$) δ 9.88 (s, 1H), 9.08 (s, 1H), 7.98 (s, 1H), 7.69 (s, 1H), 7.63 (dd, J=8.1, 1.7, 1H), 7.53-7.49 (m, 2H), 7.39 (dd, J=8.7, 7.4, 1H), 7.13 (d, J=8.2, 1H), 3.85 (s, 2H), 3.78 (s, 3H), 2.38 (s, 3H), 1.20 (s, 6H); MS (ESI): m/z 480.0 (M+H)+.

Example 61

6-(2,6-dichlorophenyl)-8-methyl-2-({4-[(1-methylpiperidin-4-yl)amino]phenyl}amino)pyrido[2,3-d]pyrimidin-5(8H)-one The title compound was prepared as described in Example 8C substituting 4-(4-methylpiperazin-1-yl)aniline with $N^1$-(1-methylpiperidin-4-yl)benzene-1,4-diamine. Purification by reverse-phase prep HPLC (Zorbax C-18, 0.1% TFA/$CH_3CN/H_2O$) afforded the title compound. $^1H$ NMR (400 MHz, dimethylsulfoxide-$d_6$) δ 9.60 (s, 1H), 9.02 (s, 1H), 7.93 (s, 1H), 7.54-7.48 (m, 4H), 7.39 (dd, J=8.7, 7.4, 1H), 6.68 (d, J=8.8, 2H), 3.73 (s, 3H), 3.54-3.02 (m, 5H), 2.79 (s, 3H), 2.25-1.53 (m, 4H); MS (ESI): m/z 509.3 (M+H)+.

Example 62

6-(2,6-dichlorophenyl)-2-({2-[4-(dimethylamino)piperidin-1-yl]pyrimidin-5-yl}amino)-8-methylpyrido[2,3-d]pyrimidin-5(8H)-one The title compound was prepared as described in Example 8C substituting 4-(4-methylpiperazin-1-yl)aniline with 1-(4-aminophenyl)-N,N-dimethylpiperidin-4-amine Purification by flash chromatography (Isco®, Redi-Sep® column, 2-50% $CH_3OH:H_2O$ (2:1) in ethyl acetate with 2% triethylamine, linear gradient) followed by recrystallization in ethyl acetate/hexane mixture afforded the title compound. $^1H$ NMR (300 MHz, dimethylsulfoxide-$d_6$) δ 10.14 (s, 1H), 9.07 (s, 1H), 8.77 (brs, 2H), 8.13 (s, 1H), 7.59-7.53 (m, 2H), 7.43 (dd, J=8.8, 7.2, 1H), 4.65-4.55 (m, 2H), 3.73 (s, 3H), 2.95-2.84 (m, 2H), 2.40-2.30 (m, 1H), 2.19 (s, 6H), 1.86-1.77 (m, 2H), 1.39-1.23 (m, 2H); MS (ESI): m/z 525.4 (M+H)+.

Example 63

6-(2,6-dichlorophenyl)-8-methyl-2-({4-[(3R)-pyrrolidin-3-ylamino]phenyl}amino)pyrido[2,3-d]pyrimidin-5(8H)-one The title compound was prepared as described in Example 8C substituting 4-(4-methylpiperazin-1-yl)aniline with (R)-tert-butyl 3-(4-aminophenylamino)pyrrolidine-1-carboxylate. Purification by silica gel flash chromatography (Isco®, Redi-Sep® column, 2-100% ethyl acetate/hexane, linear gradient) afforded the Boc protected intermediate. To the product was added 0.5 mL of $CH_2Cl_2$, 0.5 mL of $CH_3OH$ and 2 mL of ethyl acetate. 4 mL of 2 molar HCl in diethyl ether was added and the mixture stirred at 50° C. for 3 hours. The solid was then filtered and washed with diethyl ether to yield the title compound as an HCl salt. $^1H$ NMR (300 MHz, dimethylsulfoxide-$d_6$) δ 10.15 (s, 1H), 9.29 (brs, 2H), 9.05 (s, 1H), 8.12 (s, 1H), 7.67 (brd, J=7.7, 2H), 7.59-7.53 (m, 2H), 7.44 (dd, J=8.8, 7.2, 1H), 6.82 (d, J=8.1, 2H), 4.17-4.10 (m, 1H), 3.76 (s, 3H), 3.48-3.08 (m, 4H), 2.28-2.14 (m, 1H), 2.01-1.90 (m, 1H); MS (ESI): m/z 481.4 (M+H)+.

Example 64

6-(2,6-dichlorophenyl)-8-methyl-2-({4-[(3S)-pyrrolidin-3-ylamino]phenyl}amino)pyrido[2,3-d]pyrimidin-5(8H)-one The title compound was prepared as described in Example 8C substituting 4-(4-methylpiperazin-1-yl)aniline with (S)-tert-butyl 3-(4-aminophenylamino)pyrrolidine-1-carboxylate. Purification by silica gel flash chromatography (Isco®, Redi-Sep® column, 2-100% ethyl acetate/hexane, linear gradient) afforded the Boc protected intermediate. To the product was added 0.5 mL of $CH_2Cl_2$, 0.5 mL of $CH_3OH$ and 2 mL of ethyl acetate. 4 mL of 2 molar HCl in diethyl ether was added and the mixture was stirred at 50° C. for 3 hours. The solid was then filtered and washed with diethyl ether to yield the title compound as an HCl salt. $^1H$ NMR (300 MHz, dimethylsulfoxide-$d_6$) δ 10.15 (s, 1H), 9.29 (brs, 2H), 9.05 (s, 1H), 8.12 (s, 1H), 7.67 (brd, J=7.7, 2H), 7.59-7.53 (m, 2H), 7.44 (dd, J=8.8, 7.2, 1H), 6.82 (d, J=8.1, 2H), 4.17-4.10 (m, 1H), 3.76 (s, 3H), 3.48-3.08 (m, 4H), 2.28-2.14 (m, 1H), 2.01-1.90 (m, 1H); MS (ESI): m/z 481.4 (M+H)+.

Example 65

6-(2,6-dichlorophenyl)-2-[(1,1-dimethyl-2,3-dihydro-1H-isoindol-5-yl)amino]-8-methylpyrido[2,3-d]pyrimidin-5(8H)-one The title compound was prepared as described in Example 8C substituting 4-(4-methylpiperazin-1-yl)aniline with tert-butyl 5-amino-1,1-dimethylisoindoline-2-carboxylate. Purification by silica gel flash chromatography (Isco®, Redi-Sep® column, 2-100% ethyl acetate/hexane, linear gradient) afforded the Boc protected intermediate. To the product was added 0.5 mL of $CH_2Cl_2$, 0.5 mL of $CH_3OH$ and 2 mL of ethyl acetate. 4 mL of 2 molar HCl in diethyl ether was added and the mixture was stirred at 50° C. for 3 hours. The solid was then filtered and washed with diethyl ether to yield the title compound as an HCl salt. $^1H$ NMR (400 MHz, dimethylsulfoxide-$d_6$) δ 10.14 (s, 1H), 9.79 (brs, 2H), 9.12 (s, 1H), 8.02 (s, 1H), 7.90 (s, 1H), 7.81 (dd, J=8.4, 1.4, 1H), 7.54-7.49 (m, 2H), 7.40 (dd, J=8.7, 7.4, 1H), 7.32 (d, J=8.3, 1H), 4.54 (s, 2H), 3.80 (s, 3H), 1.67 (s, 6H); MS (ESI): m/z 466.3 (M+H)+.

Example 66

6-(2,6-dichlorophenyl)-8-methyl-2-{[4-(piperidin-4-ylamino)phenyl]amino}pyrido[2,3-d]pyrimidin-5(8H)-one The title compound was prepared as described in Example 8C substituting 4-(4-methylpiperazin-1-yl)aniline with tert-butyl 4-(4-aminophenylamino)piperidine-1-carboxylate. Purification by silica gel flash chromatography (Isco®, Redi-Sep® column, 3-50% ethyl acetate/hexane, linear gradient) afforded the Boc protected intermediate. To the product was added 0.5 mL of $CH_2Cl_2$, 0.5 mL of $CH_3OH$ and 2 mL of ethyl acetate. 4 mL of 2 molar HCl in diethyl ether was added and the mixture stirred at 50° C. for 3 hours. The solid was then filtered and washed with diethyl ether to yield the title compound as an HCl salt. $^1H$ NMR (400 MHz, dimethylsulfoxide-$d_6$) δ 9.77 (s, 1H), 9.05 (s, 1H), 9.03-8.72 (m, 2H), 7.96 (s, 1H), 7.65 (d, J=8.8, 2H), 7.53-7.47 (m, 2H), 7.39 (dd, J=8.7, 7.4, 1H), 6.93 (d, J=8.7, 2H), 3.76 (s, 3H), 3.69-3.66 (m, 1H), 3.63-3.48 (m, 2H), 3.04-2.92 (m, 2H), 2.16-2.06 (m, 2H), 1.83-1.72 (m, 2H); MS (ESI): m/z 494.9 (M+H)⁺.

Example 67

6-(2,6-dichlorophenyl)-8-methyl-2-({4-[(1-methylpyrrolidin-3-yl)amino]phenyl}amino)pyrido[2,3-d]pyrimidin-5(8H)-one The title compound was prepared as described in Example 8C substituting 4-(4-methylpiperazin-1-yl)aniline with $N^1$-(1-methylpyrrolidin-3-yl)benzene-1,4-diamine Purification by flash chromatography (Isco®, Redi-Sep® column, 2-50% CH₃OH:H₂O (2:1) in ethyl acetate with 2% triethylamine, linear gradient) followed by recrystallization in ethyl acetate/hexane mixture afforded the title compound. ¹H NMR (300 MHz, dimethylsulfoxide-d₆) δ 9.99 (s, 1H), 9.01 (s, 1H), 8.08 (s, 1H), 7.60-7.50 (m, 4H), 7.43 (dd, J=8.9, 7.2, 1H), 6.56 (d, J=8.8, 2H), 5.57 (d, J=7.1, 1H), 3.91-3.83 (m, 1H), 3.74 (s, 3H), 2.77-2.70 (m, 1H), 2.61-2.53 (m, 1H), 2.45-2.31 (m, 2H), 2.26 (s, 3H), 2.24-2.13 (m, 1H), 1.63-1.52 (m, 1H); MS (ESI): m/z 495.4 (M+H)⁺.

Example 68

6-(2,6-dichlorophenyl)-8-methyl-2-({4-[(1-methylpiperidin-4-yl)oxy]phenyl}amino)pyrido[2,3-d]pyrimidin-5(8H)-one The title compound was prepared as described in Example 8C substituting 4-(4-methylpiperazin-1-yl)aniline with 4-(1-methylpiperidin-4-yloxy)aniline. Purification by reverse-phase prep HPLC (Zorbax C-18, 0.1% ammonium acetate/CH₃CN/H₂O) afforded the title compound. ¹H NMR (400 MHz, dimethylsulfoxide-d₆) δ 9.79 (s, 1H), 9.06 (s, 1H), 7.95 (s, 1H), 7.70 (d, J=9.0, 2H), 7.52-7.48 (m, 2H), 7.39 (dd, J=8.7, 7.4, 1H), 6.94 (d, J=9.0, 2H), 4.34-4.27 (m, 1H), 3.76 (s, 3H), 2.73-2.66 (m, 2H), 2.34-2.28 (m, 2H), 2.26 (s, 3H), 1.98-1.90 (m, 2H), 1.74-1.65 (m, 2H); MS (ESI): m/z 510.0 (M+H)⁺.

Example 69

6-(2-chloro-6-fluorophenyl)-8-methyl-2-({4-[(1-methylpiperidin-4-yl)amino]phenyl}amino)pyrido[2,3-d]pyrimidin-5(8H)-one The title compound was prepared as described in Example 8C substituting Example 8B with Example 33C and substituting 4-(4-methylpiperazin-1-yl)aniline with $N^1$-(1-methylpiperidin-4-yl)benzene-1,4-diamine. Purification by reverse-phase prep HPLC (Zorbax C-18, 0.1% ammonium acetate/CH₃CN/H₂O) afforded the title compound. ¹H NMR (400 MHz, dimethylsulfoxide-d₆) δ 9.53 (s, 1H), 9.00 (s, 1H), 7.96 (s, 1H), 7.47 (d, J=8.8, 2H), 7.43-7.34 (m, 2H), 7.25-7.18 (m, 1H), 6.60 (d, J=8.8, 2H), 3.72 (s, 3H), 3.23-3.15 (m, 1H), 2.78-2.72 (m, 2H), 2.22 (s, 3H), 2.15-2.08 (m, 2H), 1.94-1.86 (m, 2H), 1.50-1.39 (m, 2H); MS (ESI): m/z 493.2 (M+H)⁺.

Example 70

6-(2-chloro-6-fluorophenyl)-8-methyl-2-[(1,1,2-trimethyl-2,3-dihydro-1H-isoindol-5-yl)amino]pyrido[2,3-d]pyrimidin-5(8H)-one The title compound was prepared as described in Example 8C substituting Example 8B with Example 33C and substituting 4-(4-methylpiperazin-1-yl)aniline with 1,1,2-trimethylisoindolin-5-amine. Purification by reverse-phase prep HPLC (Zorbax C-18, 0.1% ammonium acetate/CH₃CN/H₂O) afforded the title compound. ¹H NMR (400 MHz, dimethylsulfoxide-d₆) δ 9.98 (s, 1H), 9.19 (s, 1H), 8.13 (s, 1H), 7.80 (s, 1H), 7.75-7.71 (m, 1H), 7.56-7.46 (m, 2H), 7.36-7.30 (m, 1H), 7.24 (d, J=8.2, 1H), 3.96 (s, 2H), 3.88 (s, 3H), 2.49 (s, 3H), 1.31 (s, 6H); MS (ESI): m/z 464.1 (M+H)⁺.

Example 71 methyl 5-{[6-(2,6-dichlorophenyl)-8-methyl-5-oxo-5,8-dihydropyrido[2,3-d]pyrimidin-2-yl]amino}-2-(4-methylpiperazin-1-yl)benzoate The title compound was prepared as described in Example 8C substituting 4-(4-methylpiperazin-1-yl)aniline with methyl 5-amino-2-(4-methylpiperazin-1-yl)benzoate. Purification by reverse-phase prep HPLC (Zorbax C-18, 0.1% ammonium acetate/CH₃CN/H₂O) afforded the title compound. ¹H NMR (500 MHz, dimethylsulfoxide-d₆) δ 10.05 (s, 1H), 9.08 (s, 1H), 8.25 (d, J=2.3, 1H), 8.00 (s, 1H), 7.81 (dd, J=8.9, 2.7, 1H), 7.53-7.50 (m, 2H), 7.42-7.38 (m, 1H), 7.13 (d, J=8.9, 1H), 3.82 (s, 3H), 3.79 (s, 3H), 3.02-2.87 (m, 6H), 2.48-2.45 (m, 2H), 2.25 (s, 3H); MS (ESI): m/z 553.1 (M+H)⁺.

Example 72

6-(2,6-dichlorophenyl)-2-({2-[4-(dimethylamino)piperidin-1-yl]-2,3-dihydro-1H-inden-5-yl}amino)-8-methylpyrido[2,3-d]pyrimidin-5(8H)-one Example 72A 1-(2,3-dihydro-1H-inden-2-yl)-N,N-dimethylpiperidin-4-amine The title compound was obtained as described in Example 55A substituting pyrrolidine with N,N-dimethylpiperidin-4-amine. The crude material obtained was recrystallized in ethyl acetate/hexane mixture to give the title compound. MS (ESI) m/z 245.1 (M+H)⁺.

Example 72B

N,N-dimethyl-1-(5-nitro-2,3-dihydro-1H-inden-2-yl)piperidin-4-amine

The title compound was obtained as described in Example 55B substituting Example 55A with Example 72A. Purification by silica gel flash chromatography (Isco®, Redi-Sep® column, 2-60% CH₃OH:H₂O (2:1) in ethyl acetate with 2% triethylamine, linear gradient) afforded the title compound. MS (ESI) m/z 290.2 (M+H)⁺.

Example 72C 1-(5-amino-2,3-dihydro-1H-inden-2-yl)-N,N-dimethylpiperidin-4-amine

The title compound was obtained as described in Example 55C substituting Example 55B with Example 72B and substituting palladium on carbon (10% wt) with palladium on carbon (5% wt, wet) at 30 psi for 6 hours. The crude title compound was carried through the next step without purification. MS (ESI) m/z 260 (M+H)+.

Example 72D 6-(2,6-dichlorophenyl)-2-({2-[4-(dimethylamino)piperidin-1-yl]-2,3-dihydro-1H-inden-5-yl}amino)-8-methylpyrido[2,3-d]pyrimidin-5(8H)-one The title compound was prepared as described in Example 8C substituting 4-(4-methylpiperazin-1-yl)aniline with Example 72C. Purification by flash chromatography (Isco®, Redi-Sep® column, 2-50% CH$_3$OH:H$_2$O (2:1) in ethyl acetate with 2% triethylamine, linear gradient) followed by reverse-phase prep HPLC (Zorbax C-18, 0.1% TFA/CH$_3$CN/H$_2$O) afforded the title compound. $^1$H NMR (300 MHz, dimethylsulfoxide-d$_6$) δ 10.36 (s, 1H), 9.95 (brs, 2H), 9.12 (s, 1H), 8.17 (s, 1H), 7.81 (s, 1H), 7.69 (d, J=6.9, 1H), 7.60-7.54 (m, 2H), 7.47-7.40 (m, 1H), 7.27 (d, J=8.0, 1H), 4.19-4.05 (m, 1H), 3.79 (s, 3H), 3.73-2.96 (m, 6H), 2.80 (s, 6H), 2.34-2.25 (m, 2H), 1.93-1.74 (m, 2H); MS (ESI): m/z 563.3 (M+H)+.

Example 73

6-(2-chloro-6-fluorophenyl)-8-methyl-2-{[4-(piperidin-4-ylamino)phenyl]amino}pyrido[2,3-d]pyrimidin-5(8H)-one The title compound was prepared as described in Example 8C substituting Example 8B with Example 33C and substituting 4-(4-methylpiperazin-1-yl)aniline with tert-butyl 4-(4-aminophenylamino)piperidine-1-carboxylate. Purification by silica gel flash chromatography (Isco®, Redi-Sep® column, 10-90% ethyl acetate/hexane, linear gradient) afforded the Boc protected intermediate. To the product was added 0.5 mL of CH$_2$Cl$_2$, 0.5 mL of CH$_3$OH and 2 mL of ethyl acetate. 4 mL of 2 molar HCl in diethyl ether was added and the mixture stirred at 50° C. for 3 hours. The solid was then filtered and washed with diethyl ether to yield the title compound as an HCl salt. $^1$H NMR (500) MHz, dimethylsulfoxide-d$_6$) δ 9.85 (s, 1H), 9.05 (s, 1H), 8.90 (brm, 2H), 8.03 (s, 1H), 7.67 (d, J=8.7, 2H), 7.46-7.36 (m, 2H), 7.27-7.20 (m, 1H), 6.95 (d, J=7.9, 2H), 3.76 (s, 3H), 3.52-3.48 (m, J=11.7, 4.6, 1H), 3.35-3.29 (m, 2H), 3.01-2.93 (m, 2H), 2.13-2.07 (m, 2H), 1.82-1.73 (m, 2H); MS (ESI): m/z 479.1 (M+H)+.

Example 74

6-(2-chloro-6-fluorophenyl)-8-methyl-2-(1,2,3,4-tetrahydroisoquinolin-7-ylamino)pyrido[2,3-d]pyrimidin-5(8H)-one The title compound was prepared as described in Example 8C substituting Example 8B with Example 33C and substituting 4-(4-methylpiperazin-1-yl)aniline with tert-butyl 7-amino-3,4-dihydroisoquinoline-2(1H)-carboxylate. Purification by silica gel flash chromatography (Isco®, Redi-Sep® column, 10-90% ethyl acetate/Hexane, linear gradient) afforded the Boc protected intermediate. To the product was added 0.5 mL of CH$_2$Cl$_2$, 0.5 mL of CH$_3$OH and 2 mL of ethyl acetate. 4 mL of 2 molar HCl in diethyl ether was added and the mixture stirred at 50° C. for 3 hours. The solid was then filtered and washed with diethyl ether to yield the title compound as an HCl salt. $^1$H NMR (500) MHz, dimethylsulfoxide-d$_6$) δ 10.07 (s, 1H), 9.55 (brs, 2H), 9.10 (s, 1H), 8.08 (s, 1H), 7.75 (s, 1H), 7.66-7.64 (m, 1H), 7.47-7.36 (m, 2H), 7.27-7.18 (m, 2H), 4.25 (s, 2H), 3.79 (s, 3H), 3.39-3.32 (m, 2H), 3.03-2.98 (m, 2H); MS (ESI): m/z 436.0 (M+H)+

Example 75

6-(2-chloro-6-fluorophenyl)-8-methyl-2-(1,2,3,4-tetrahydroisoquinolin-6-ylamino)pyrido[2,3-d]pyrimidin-5(8H)-one The title compound was prepared as described in Example 8C substituting Example 8B with Example 33C and substituting 4-(4-methylpiperazin-1-yl)aniline with tert-butyl 6-amino-3,4-dihydroisoquinoline-2(1H)-carboxylate. Purification by silica gel flash chromatography (Isco®, Redi-Sep® column, 10-90% ethyl acetate/hexane, linear gradient) afforded the Boc protected intermediate. To the product was added 0.5 mL of CH$_2$Cl$_2$, 0.5 mL of CH$_3$OH and 2 mL of ethyl acetate. 4 mL of 2 molar HCl in diethyl ether was added and the mixture was stirred at 50° C. for 3 hours. The solid was then filtered and washed with diethyl ether to yield the title compound as an HCl salt. $^1$H NMR (500) MHz, dimethylsulfoxide-d$_6$) δ 10.07 (s, 1H), 9.57 (brs, 2H), 9.11 (s, 1H), 8.09 (s, 1H), 7.76 (s, 1H), 7.67 (dd, J=8.4, 2.1, 1H), 7.47-7.37 (m, 2H), 7.26-7.22 (m, 1H), 7.20 (d, J=8.4, 1H), 4.21 (s, 2H), 3.79 (s, 3H), 3.38-3.31 (m, 2H), 3.08-3.03 (m, 2H); MS (ESI): m/z 435.7 (M+H)+.

Example 76

6-(2,6-dichlorophenyl)-2-[(4-{[trans-4-(dimethylamino)cyclohexyl]amino}phenyl)amino]-8-methylpyrido[2,3-d]pyrimidin-5(8H)-one Example 76A N$^1$,N$^1$-dimethyl-N$^4$-(4-nitrophenyl)cyclohexane-1,4-diamine To a solution of 1-fluoro-4-nitrobenzene (0.392 ml, 3.69 mmol) in 4 mL of dimethyl sulfoxide was added N$^1$,N$^1$-dimethylcyclohexane-1,4-diamine (500 mg, 3.52 mmol) and N-ethyl-N-isopropylpropan-2-amine (2.449 ml, 14.06 mmol). The reaction mixture was stirred at 100° C. for 24 hours. The mixture was poured into a separatory funnel and was diluted with 50 mL of ethyl acetate. The organic mixture was then washed with 50 mL of water followed by 50 mL of saturated aqueous brine. The organic phase was dried over sodium sulfate, filtered and concentrated. The crude material obtained was carried through the next step without purification. MS (ESI) m/z 264.1 (M+H)+.

Example 76B N1-(4-(dimethylamino)cyclohexyl)benzene-1,4-diamine

The title compound was obtained as described in Example 55C substituting Example 55B with Example 76A to give the crude title compound which was carried through the next step without purification. MS (ESI) m/z 234.2 (M+H)+.

Example 76C 6-(2,6-dichlorophenyl)-2-[(4-{[trans-4-(dimethylamino)cyclohexyl]amino}phenyl)amino]-8-methylpyrido[2,3-d]pyrimidin-5(8H)-one The title compound was prepared as described in Example 8C substituting 4-(4-methylpiperazin-1-yl)aniline with Example 76B (cis/trans mixture). Purification by reverse-phase prep HPLC (Zorbax C-18, 0.1% TFA/CH₃CN/H₂O) afforded two products. COSY ROESY and HSQC experiments showed that the fast eluting product is the title compound (trans isomer). $^1$H NMR (500) MHz, pyridine-$d_5$) δ 10.61 (s, 1H), 9.54 (s, 1H), 7.90 (d, J=8.4, 2H), 7.74 (s, 1H), 7.43 (d, J=8.1, 2H), 6.91 (d, J=8.4, 2H), 3.64 (s, 3H), 3.36-3.29 (m, 1H), 3.07-2.99 (m, 1H), 2.70 (s, 6H), 2.28-2.22 (m, 2H), 2.16-2.09 (m, 2H), 1.67-1.57 (m, 2H), 1.32-1.21 (m, 2H); MS (ESI): m/z 537.0 (M+H)⁺.

Example 77

6-(2,6-dichlorophenyl)-2-[(4-{[cis-4-(dimethylamino)cyclohexyl]amino}phenyl)amino]-8-methylpyrido[2,3-d]pyrimidin-5(8H)-one The title compound was prepared as described in Example 8C substituting 4-(4-methylpiperazin-1-yl)aniline with 76B (cis/trans mixture). Purification by reverse-phase prep HPLC (Zorbax C-18, 0.1% TFA/CH₃CN/H₂O) afforded two products. COSY ROESY and HSQC experiments showed that the slow eluting product is the title compound (cis isomer). $^1$H NMR (500) MHz, pyridine-$d_5$) δ 10.59 (s, 1H), 9.53 (s, 1H), 7.87 (d, J=8.5, 2H), 7.73 (s, 1H), 7.42 (d, J=8.1, 2H), 6.97 (d, J=8.5, 2H), 3.69-3.66 (m, 1H), 3.62 (s, 3H), 3.05-2.97 (m, 1H), 2.68 (s, 6H), 2.09-1.97 (m, 4H), 1.89-1.83 (m, 2H), 1.57-1.50 (m, 2H); MS (ESI): m/z 537.0 (M+H)⁺.

Example 78

6-(2,6-dichlorophenyl)-2-[(4-{4-[3-(dimethylamino)propyl]piperazin-1-yl}phenyl)amino]-8-methylpyrido[2,3-d]pyrimidin-5(8H)-one The title compound was prepared as described in Example 8C substituting 4-(4-methylpiperazin-1-yl)aniline with $N^1$-(3-(dimethylamino)propyl)benzene-1,4-diamine. Purification by reverse-phase prep HPLC (Zorbax C-18, 0.1% TFA/CH₃CN/H₂O) afforded the title compound. $^1$H NMR (400 MHz, dimethylsulfoxide-$d_6$) δ 9.71 (s, 1H), 9.04 (s, 1H), 7.94 (s, 1H), 7.64 (d, J=9.1, 2H), 7.53-7.48 (m, 2H), 7.39 (dd, J=8.8, 7.3, 1H), 6.92 (d, J=9.1, 2H), 3.75 (s, 3H), 3.13-3.08 (m, 4H), 2.54-2.50 (m, 4H), 2.38-2.28 (m, 4H), 2.17 (s, 6H), 1.65-1.55 (m, 2H); MS (ESI): m/z 566.4 (M+H)⁺.

Example 79

6-(2,6-dichlorophenyl)-2-[(4-{4-[2-(dimethylamino)ethyl]piperazin-1-yl}phenyl)amino]-8-methylpyrido[2,3-d]pyrimidin-5(8H)-one The title compound was prepared as described in Example 8C substituting 4-(4-methylpiperazin-1-yl)aniline with $N^1$-(2-(dimethylamino)ethyl)benzene-1,4-diamine Purification by reverse-phase prep HPLC (Zorbax C-18, 0.1% TFA/CH₃CN/H₂O) afforded the title compound. $^1$H NMR (400 MHz, dimethylsulfoxide-$d_6$) δ 9.73 (s, 1H), 9.04 (s, 1H), 7.95 (s, 1H), 7.66 (d, J=9.0, 2H), 7.54-7.48 (m, 2H), 7.39 (dd, J=8.8, 7.3, 1H), 6.94 (d, J=9.1, 2H), 3.75 (s, 3H), 3.20-3.10 (m, 6H), 2.71 (s, 6H), 2.71-2.63 (m, 6H); MS (ESI): m/z 552.4 (M+H)⁺.

Example 80

Wee1 Assay

Wee1 kinase was assayed using a time-resolved fluorescence equilibrium binding assay monitoring displacement of a rapidly reversible Oregon Green-labeled ATP-competitive kinase probe (N-(2-(2-(2-(4-(4-(5-chloro-4-(2-(1-hydroxycyclobutyl)thiazol-5-yl)-1H-pyrrolo[2,3-b]pyridin-2-yl)phenyl)piperazin-1-yl)ethoxy)ethoxy)ethyl)-2',7'-difluoro-3',6'-dihydroxy-3-oxo-3H-spiro[isobenzofuran-1,9'-xanthene]-5-carboxamide) by competitive Wee1 inhibitors. GST-tagged-Wee1 kinase (Carnabio #05-177, 2 nM final concentration), was mixed with fluorescent probe (300 nM final concentration, $K_d$=137 nM) and terbium-labeled anti-GST antibody (1 nM final concentration, Invitrogen #PV3551) and then inhibitor (0.003 to 10 micromolar) in final volume of 18 μl kinase buffer (20 mM HEPES, pH 7.5, 10 mM MgCl₂, 100 μM Na₃VO₄, 0.0075% Triton X-100, 1 mM DTT, 2% DMSO), incubated (1 hour) to allow attainment of equilibrium and time-resolved fluorescence measured using an Envision plate reader (Perkin Elmer; ex=337 nM, em=495/520 nM).

Table 1 depicts enzyme binding inhibition data ($K_i$) for exemplary compounds.

| Example | Wee-1 binding ($K_i$ nM) |
| --- | --- |
| 1 | 9.5 |
| 2 | 2.4 |
| 3 | 37 |
| 4 | 0.1 |
| 5 | 3.7 |
| 6 | 5.7 |
| 7 | 0.6 |
| 8 | 0.3 |
| 9 | <1 |
| 10 | <1 |
| 11 | 3 |
| 12 | 14 |
| 13 | 24 |
| 14 | 0.3 |
| 15 | 0.6 |
| 16 | 20 |
| 17 | 0.2 |
| 18 | 0.3 |
| 19 | 0.3 |
| 20 | 0.3 |
| 21 | 0.3 |
| 22 | 0.6 |
| 23 | 0.8 |
| 24 | 0.8 |
| 25 | 1.2 |
| 26 | 1.2 |
| 27 | 1.3 |
| 28 | 19 |
| 29 | 6.4 |
| 30 | 0.2 |
| 31 | 0.6 |
| 32 | 0.3 |
| 33 | 1.5 |
| 34 | 0.4 |
| 35 | 66 |
| 36 | 33 |
| 37 | 2.4 |
| 38 | 1.3 |
| 39 | 0.7 |
| 40 | 2.4 |
| 41 | 0.4 |
| 42 | 0.2 |
| 43 | 0.3 |
| 44 | 0.5 |
| 45 | 180 |
| 46 | 1.1 |
| 47 | 0.6 |
| 48 | 1.7 |
| 49 | 0.8 |
| 50 | 0.9 |
| 51 | 0.4 |
| 52 | 0.5 |

-continued

| Example | Wee-1 binding ($K_i$ nM) |
|---|---|
| 53 | 3.4 |
| 54 | 0.3 |
| 55 | 0.4 |
| 56 | 27 |
| 57 | 0.9 |
| 58 | 0.4 |
| 59 | 18 |
| 60 | 0.2 |
| 61 | 0.6 |
| 62 | 3 |
| 63 | 0.7 |
| 64 | 0.4 |
| 65 | 0.3 |
| 66 | 0.4 |
| 67 | 0.5 |
| 68 | 0.4 |
| 69 | 3 |
| 70 | 0.2 |
| 71 | 0.7 |
| 72 | 0.5 |
| 73 | 2.8 |
| 74 | 1.2 |
| 75 | 1.3 |
| 76 | 0.7 |
| 77 | 0.5 |
| 78 | 1.2 |
| 79 | 0.8 |

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A compound of formula (I):

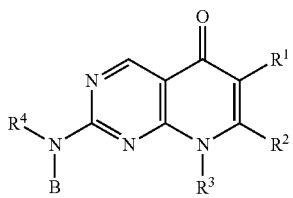

formula (I)

B is
(a) $C_{3-8}$ cycloalkyl, phenyl, naphthyl, tetrahydronaphthyl, indenyl, or indanyl, wherein the $C_{3-8}$ cycloalkyl, phenyl, naphthyl, tetrahydronaphthyl, indenyl, or indanyl is optionally substituted with one or more $R^5$; or
(b) 5-16 membered monocyclic, bicyclic, or tricyclic heterocyclyl, wherein the heterocyclyl is optionally substituted with one or more $R^6$;

$R^1$ is hydrogen, $C_{1-8}$-alkyl, $C_{2-8}$-alkenyl, $C_{2-8}$-alkynyl, $C_{3-8}$-cycloalkyl, aryl, heteroaryl, aryl-$C_{1-6}$-alkyl-, $C_{3-8}$ cycloalkyl-$C_{1-6}$-alkyl-, or heteroaryl-$C_{1-6}$-alkyl-; wherein (a) the $C_{1-8}$-alkyl, $C_{2-8}$-alkenyl, or $C_{2-8}$-alkynyl, alone or as part of another moiety, is optionally substituted with one or more substituents selected from the group consisting of CN, $NO_2$, halo, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$; and (b) the $C_{3-8}$-cycloalkyl, aryl, or heteroaryl is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$,—$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$,—$NHC(O)NHR^e$, —$NHC(O)OR^e$, —$NHSO_2R^d$, —$C(O)NHR^e$, and —$SO_2NHNR^e$;

$R^2$ is hydrogen, $C_{1-6}$-alkyl, $C_{3-8}$ cycloalkyl, aryl, heteroaryl, heterocycloalkyl, aryl-$C_{1-6}$-alkyl-, cycloalkyl-$C_{1-6}$-alkyl-, heteroaryl-$C_{1-6}$-alkyl-, or heterocycloalkyl-$C_{1-6}$-alkyl-, wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the $C_{3-8}$ cycloalkyl, aryl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^3$ is hydrogen, $C_{1-6}$-alkyl, $C_{3-8}$ cycloalkyl, aryl, heteroaryl, heterocycloalkyl, aryl-$C_{1-6}$-alkyl-, cycloalkyl-$C_{1-6}$-alkyl-, heteroaryl-$C_{1-6}$-alkyl-, or heterocycloalkyl-$C_{1-6}$-alkyl-, wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the $C_{3-8}$ cycloalkyl, aryl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^4$ is hydrogen or $C_{1-6}$-alkyl;

$R^5$, at each occurrence, is independently CN, $NO_2$, halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, or heterocycloalkyl-$C_{1-6}$-alkyl-; wherein the aryl, cycloalkyl, heteroaryl, or heterocycloalkyl, alone or as part of another moiety, is optionally substituted with one or more $R^7$;

$R^6$, at each occurrence, is independently CN, $NO_2$, halo, $C_{1-6}$-alkyl, $C_{1-6}$-haloalkyl, cycloalkyl, heterocycloalkyl, or $C_{1-4}$-alkyl-heterocycloalkyl-; $R^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$;

$R^7$, at each occurrence, is independently CN, $NO_2$, halo, $C_{1-6}$-alkyl, $C_{1-6}$-haloalkyl, $C_{1-6}$-alkyl-N($C_{1-6}$-alkyl$)_2$, $OR^m$, $SR^m$, $C(O)R^m$, $C(O)NR''R^o$, $C(O)OR^m$, $NR''R^o$, $NR''C(O)R^m$, $S(O)_2R^m$, $NR''S(O)_2R^m$, or $S(O)_2NR'''R^o$;

$R^a$, at each occurrence, is independently selected from the group consisting of hydrogen, $C_{1-6}$ alkyl, $C_{1-6}$ haloalkyl, aryl, $C_{3-8}$ cycloalkyl, heteroaryl, and heterocycloalkyl;

$R^b$ and $R^c$, at each occurrence, are independently selected from the group consisting of hydrogen, $C_{1-6}$ alkyl, $C_{1-6}$ haloalkyl, aryl, $C_{3-8}$ cycloalkyl, heteroaryl, and heterocycloalkyl;

$R^d$, at each occurrence, is independently selected from the group consisting of hydrogen, $C_{1-6}$ alkyl, $C_{1-6}$ haloalkyl, aryl, $C_{3-8}$ cycloalkyl, heteroaryl, and heterocycloalkyl;

$R^e$ and $R^f$, at each occurrence, are independently selected from the group consisting of hydrogen, $C_{1-6}$ alkyl, $C_{1-6}$ haloalkyl, aryl, $C_{3-8}$ cycloalkyl, heteroaryl, and heterocycloalkyl;

$R^g$, at each occurrence, is independently selected from the group consisting of hydrogen, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, and heterocycloalkyl are optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$;

$R^h$ and $R^i$, at each occurrence, are independently selected from the group consisting of hydrogen, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, and heterocycloalkyl are optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$;

$R^j$, at each occurrence, is independently selected from the group consisting of hydrogen, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, and heterocycloalkyl are optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$;

$R^k$ and $R^l$, at each occurrence, are independently selected from the group consisting of hydrogen, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, and heterocycloalkyl are optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and —$N(C_{1-6}$-alkyl$)_2$;

$R^m$, at each occurrence, is independently selected from the group consisting of hydrogen, $C_{1-6}$ alkyl, $C_{1-6}$ haloalkyl, aryl, $C_{3-8}$ cycloalkyl, heteroaryl, and heterocycloalkyl; and $R^n$ and $R^o$, at each occurrence, are independently selected from the group consisting of hydrogen, $C_{1-6}$ alkyl, $C_{1-6}$ haloalkyl, aryl, $C_{3-8}$ cycloalkyl, heteroaryl, and heterocycloalkyl;

or a pharmaceutically acceptable salt or solvate thereof.

2. The compound of claim 1 of formula (I), or a pharmaceutically acceptable salt or solvate thereof, wherein $R^1$ is $C_{1-8}$-alkyl or $C_{2-8}$-alkenyl, wherein the $C_{1-8}$-alkyl or $C_{2-8}$-alkenyl is optionally substituted with one, two, or three substituents independently selected from the group consisting of CN, $NO_2$, halo, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$.

3. The compound of claim 1 of formula (I), or a pharmaceutically acceptable salt or solvate thereof, wherein $R^1$ is $C_{3-8}$-cycloalkyl, aryl, or heteroaryl, wherein the $C_{3-8}$-cycloalkyl, aryl, or heteroaryl is optionally substituted with one, two, or three substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$.

4. The compound of claim 1 of formula (I), or a pharmaceutically acceptable salt or solvate thereof, wherein $R^1$ is phenyl, wherein the phenyl is optionally substituted with one, two, or three substituents independently selected from the group consisting of CN, $NO_2$, halo, —$OR^g$, —$C(O)OR^g$, —$NR^hR^i$, —$NR^hC(O)R^g$, and —$C(O)NR^hR^i$.

5. The compound of claim 1 of formula (I), or a pharmaceutically acceptable salt or solvate thereof, wherein $R^2$ is $C_{1-6}$-alkyl or $C_{3-8}$ cycloalkyl, wherein the $C_{1-6}$-alkyl or $C_{3-8}$ cycloalkyl are unsubstituted.

6. The compound of claim 1 of formula (I), or a pharmaceutically acceptable salt or solvate thereof, wherein $R^2$ is hydrogen.

7. The compound of claim 1 of formula (I), or a pharmaceutically acceptable salt or solvate thereof, wherein $R^2$ and $R^3$ can be joined together to form a 5-8 membered heterocyclic ring, wherein the ring is a heterocycloalkyl ring, and the ring is optionally substituted with one, two, or three substituents independently selected from the group consisting of halo, $C_{1-6}$-alkyl, $C_{1-6}$-haloalkyl, $C_{1-6}$-hydroxyalkyl, hydroxy, $C_{1-6}$-alkoxy, $C_{1-6}$-haloalkoxy, —$NH_2$, —$NH(C_{1-6}$-alkyl), and $N(C_{1-6}$-alkyl$)_2$.

8. The compound of claim 1 of formula (I), or a pharmaceutically acceptable salt or solvate thereof, wherein $R^3$ is hydrogen.

9. The compound of claim 1 of formula (I), or a pharmaceutically acceptable salt or solvate thereof, wherein $R^3$ is aryl, $C_{3-8}$ cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, or heterocycloalkyl-$C_{1-6}$-alkyl-, wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$.

10. The compound of claim 9 of formula (I), or a pharmaceutically acceptable salt or solvate thereof, wherein $R^3$ is phenyl or pyridyl, wherein the phenyl or pyridyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, $C_{1-6}$-alkoxy, $C_{1-6}$-haloalkoxy, —$NH_2$, —$NH(C_{1-6}$-alkyl), and $N(C_{1-6}$-alkyl$)_2$.

11. The compound of claim 9 of formula (I), or a pharmaceutically acceptable salt or solvate thereof, wherein $R^3$ is $C_{3-8}$ cycloalkyl or 3-8 membered heterocycloalkyl, wherein the cycloalkyl or heterocycloalkyl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —NH$_2$, —NH($C_{1-6}$-alkyl), and N($C_{1-6}$-alkyl)$_2$.

12. The compound of claim 1 of formula (I), or a pharmaceutically acceptable salt or solvate thereof, wherein R$^3$ is $C_{1-6}$-alkyl, wherein the $C_{1-6}$-alkyl is optionally substituted with one or more substituents independently selected from the group consisting of halo, hydroxy, $C_{1-6}$-alkoxy, —NH$_2$, —NHC$_{1-6}$-alkyl, and —N($C_{1-6}$-alkyl)$_2$.

13. The compound of claim 1 of formula (I), or a pharmaceutically acceptable salt or solvate thereof, wherein B is phenyl, wherein the phenyl is substituted with one, two, or three R$^5$, and R$^5$, at each occurrence, is independently halo, $C_{1-6}$-alkyl, $C_{1-6}$ haloalkyl, OR$^g$, NR$^h$R$^i$, cycloalkyl, heteroaryl, heterocycloalkyl, or heterocycloalkyl-$C_{1-6}$-alkyl-, wherein the heterocycloalkyl, alone or as part of another moiety, is optionally substituted with one, two, or three R$^7$; and R$^7$, at each occurrence, is independently $C_{1-6}$-alkyl, $C_{1-6}$ haloalkyl, or C(O)R$^m$.

14. The compound of claim 1 of formula (I), or a pharmaceutically acceptable salt or solvate thereof, wherein B is

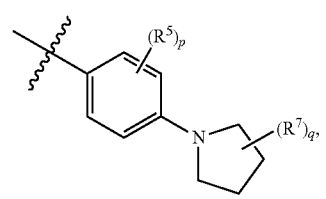

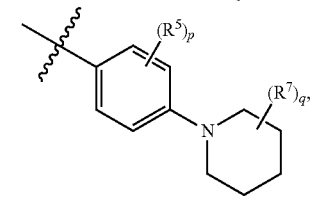

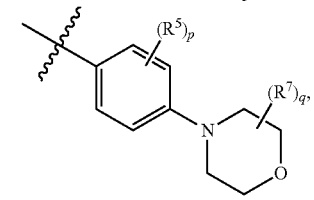

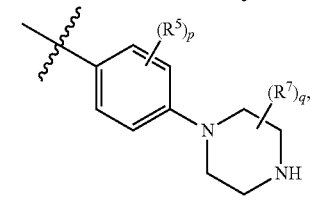

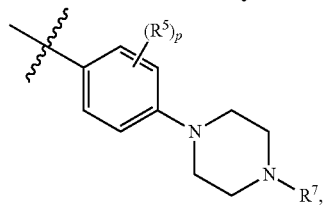

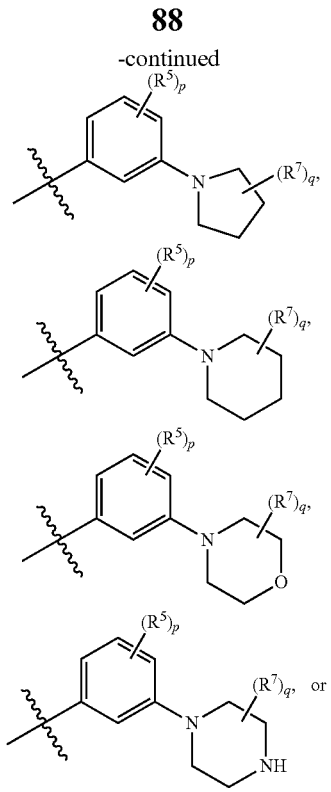

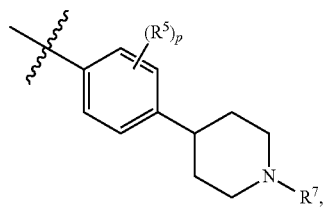

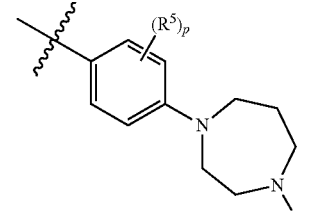

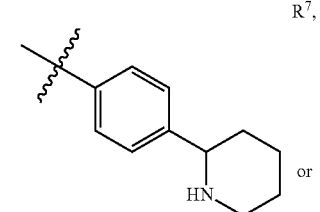

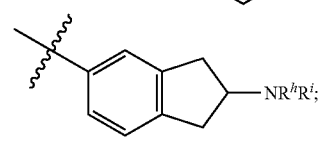

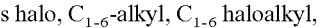

wherein R$^5$ is halo, $C_{1-6}$-alkyl, $C_{1-6}$ haloalkyl, or OR$^g$; p is 0 or 1; R$^7$ is $C_{1-6}$-alkyl, $C_{1-6}$-haloalkyl, OR$^m$, C(O)R$^m$, C(O)NR''R°, C(O)OR$^m$, NR''R°, NR''C(O)R$^m$, S(O)$_2$R$^m$, or S(O)$_2$NR''R°; and q is 0 or 1.

15. The compound of claim 1 of formula (I), or a pharmaceutically acceptable salt or solvate thereof, wherein B is $C_{3-8}$-cycloalkyl, tetrahydronaphthyl, or indanyl, wherein the $C_{3-8}$-cycloalkyl, tetrahydronaphthyl, or indanyl is optionally substituted with one, two, or three R⁵, and R⁵, at each occurrence, is independently halo, $C_{1-6}$-alkyl, $C_{1-6}$-haloalkyl, OR$^g$, SR$^g$, C(O)R$^g$, C(O)NR$^h$R$^i$, C(O)OR$^g$, NR$^h$R$^i$, NR$^h$C(O)R$^g$, S(O)₂R$^g$, NR$^h$S(O)₂R$^g$, or S(O)₂NR$^h$R$^i$.

16. The compound of claim 1 of formula (I), or a pharmaceutically acceptable salt or solvate thereof, wherein B is a monocyclic heterocyclyl, wherein the heterocyclyl is a 5-7 membered heteroaryl which is optionally substituted with one, two or three R⁶, and R⁶, at each occurrence, is independently halo, $C_{1-6}$-alkyl, $C_{1-6}$-haloalkyl, C(O)R$^j$, C(O)OR$^j$, NR$^k$R$^l$, or S(O)₂R$^j$.

17. The compound of claim 1 of formula (I), or a pharmaceutically acceptable salt or solvate thereof, wherein B is a bicyclic heterocyclyl, wherein the heterocyclyl is a 7-11 membered bicyclic heterocyclyl which is optionally substituted with one, two or three R⁶, and R⁶, at each occurrence, is independently halo, $C_{1-6}$-alkyl, $C_{1-6}$-haloalkyl, C(O)R$^j$, C(O)OR$^j$, NR$^k$R$^l$, or S(O)₂R$^j$.

18. The compound of claim 1 of formula (I), or a pharmaceutically acceptable salt or solvate thereof, wherein B is

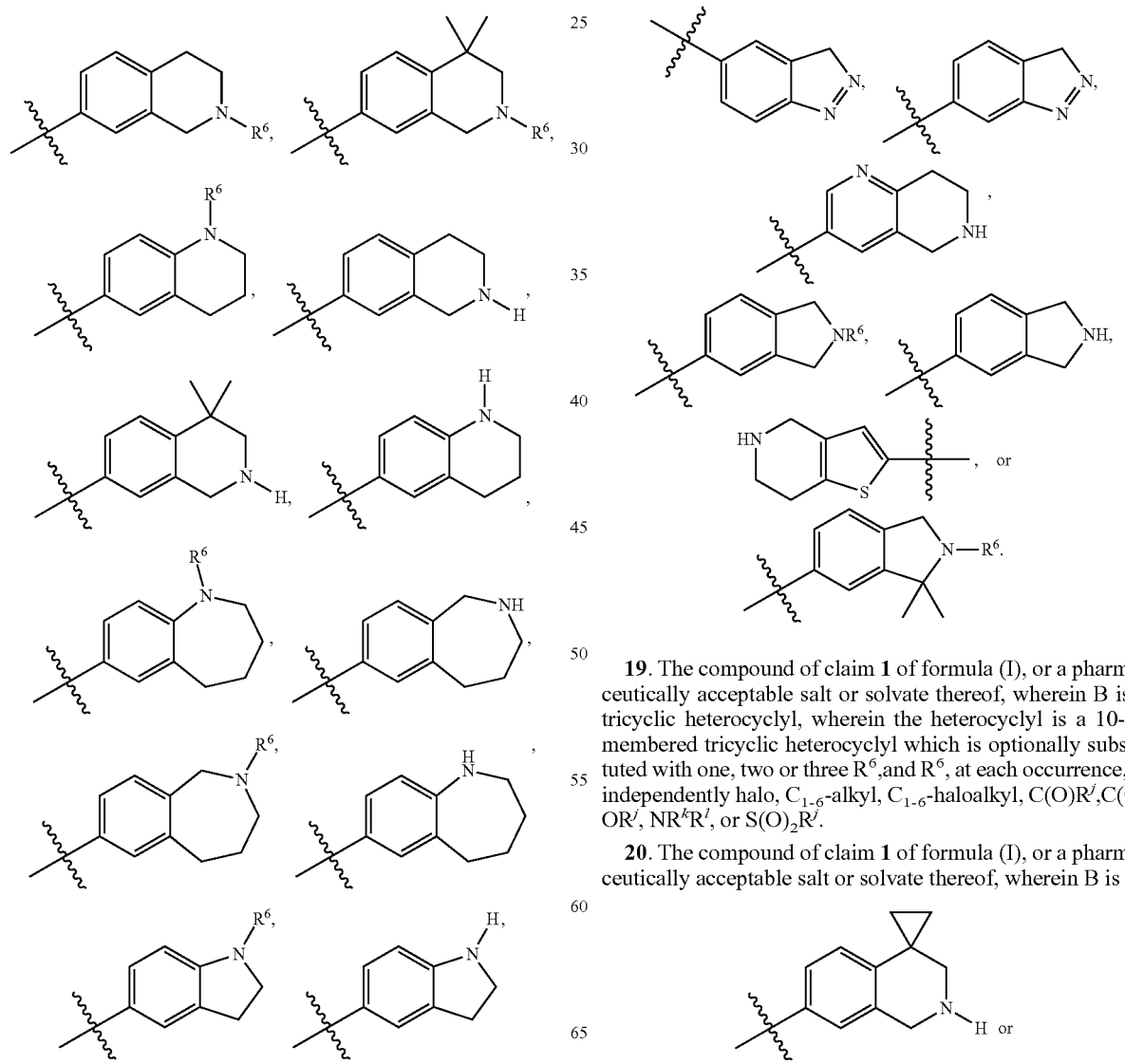

19. The compound of claim 1 of formula (I), or a pharmaceutically acceptable salt or solvate thereof, wherein B is a tricyclic heterocyclyl, wherein the heterocyclyl is a 10-15 membered tricyclic heterocyclyl which is optionally substituted with one, two or three R⁶, and R⁶, at each occurrence, is independently halo, $C_{1-6}$-alkyl, $C_{1-6}$-haloalkyl, C(O)R$^j$, C(O)OR$^j$, NR$^k$R$^l$, or S(O)₂R$^j$.

20. The compound of claim 1 of formula (I), or a pharmaceutically acceptable salt or solvate thereof, wherein B is

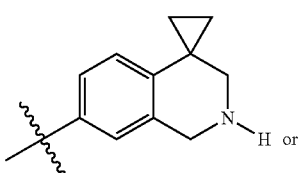

-continued

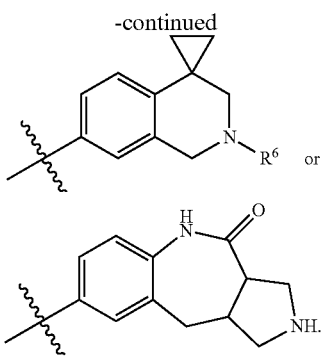

21. The compound or a pharmaceutically acceptable salt or solvate thereof, selected from the group consisting of
- 6-(2-chlorophenyl)-2-{[4-(4-methylpiperazin-1-yl)phenyl]amino}pyrido[2,3-d]pyrimidin-5(8H)-one,
- 6-(2-chlorophenyl)-2-{[4-(4-methylpiperazin-1-yl)phenyl]amino}-8-phenylpyrido[2,3-d]pyrimidin-5(8H)-one,
- 6-(2-chlorophenyl)-2-{[4-(4-methylpiperazin-1-yl)phenyl]amino}-7-phenylpyrido[2,3-d]pyrimidin-5(8H)-one,
- 6-(2,6-dichlorophenyl)-2-{[4-(4-methylpiperazin-1-yl)phenyl]amino}-8-phenylpyrido[2,3-d]pyrimidin-5(8H)-one,
- 6-(2-chlorophenyl)-8-methyl-2-{[4-(4-methylpiperazin-1-yl)phenyl]amino}pyrido[2,3-d]pyrimidin-5(8H)-one,
- 6-(2,6-dichlorophenyl)-2-{[4-(4-methylpiperazin-1-yl)phenyl]amino}-8,9-dihydropyrimido[4,5-e]indolizin-5(7H)-one,
- 6-(2,6-dichlorophenyl)-2-{[4-(4-methylpiperazin-1-yl)phenyl]amino}-8-(pyridin-4-yl)pyrido[2,3-d]pyrimidin-5(8H)-one,
- 6-(2,6-dichlorophenyl)-8-methyl-2-{[4-(4-methylpiperazin-1-yl)phenyl]amino}pyrido[2,3-d]pyrimidin-5(8H)-one,
- 6-(2,6-dichlorophenyl)-8-(4-fluorophenyl)-2-{[4-(4-methylpiperazin-1-yl)phenyl]amino}pyrido[2,3-d]pyrimidin-5(8H)-one,
- 8-cyclopropyl-6-(2,6-dichlorophenyl)-2-{[4-(4-methylpiperazin-1-yl)phenyl]amino}pyrido[2,3-d]pyrimidin-5(8H)-one,
- 6-(2,6-dichlorophenyl)-2-{[4-(4-methylpiperazin-1-yl)phenyl]amino}-8-(2,2,2-trifluoroethyl)pyrido[2,3-d]pyrimidin-5(8H)-one,
- 6-(2,6-dichlorophenyl)-2-{[4-(4-methylpiperazin-1-yl)phenyl]amino}-8-(pyridin-4-ylmethyl)pyrido[2,3-d]pyrimidin-5(8H)-one,
- 6-(2,6-dichlorophenyl)-8-[2-(dimethylamino)ethyl]-2-{[4-(4-methylpiperazin-1-yl)phenyl]amino}pyrido[2,3-d]pyrimidin-5(8H)-one,
- 6-(2,6-dichlorophenyl)-8-methyl-2-[(2'-methyl-2',3'-dihydro-1'H-spiro[cyclopropane-1,4'-isoquinolin]-7'-yl)amino]pyrido[2,3-d]pyrimidin-5(8H)-one,
- 8-cyclobutyl-6-(2,6-dichlorophenyl)-2-{[4-(4-methylpiperazin-1-yl)phenyl]amino}pyrido[2,3-d]pyrimidin-5(8H)-one,
- 6-(2,6-dichlorophenyl)-8-(2-hydroxy-2-methylpropyl)-2-{[4-(4-methylpiperazin-1-yl)phenyl]amino}pyrido[2,3-d]pyrimidin-5(8H)-one,
- 8-cyclopropyl-6-(2,6-dichlorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one,
- 6-(2,6-dichlorophenyl)-2-{[4-(4-methylpiperazin-1-yl)phenyl]amino}pyrido[2,3-d]pyrimidin-5(8H)-one,
- 6-(2,6-dichlorophenyl)-8-methyl-2-{[3-methyl-4-(4-methyl-1,4-diazepan-1-yl)phenyl]amino}pyrido[2,3-d]pyrimidin-5(8H)-one,
- 6-(2,6-dichlorophenyl)-8-methyl-2-[(2,4,4-trimethyl-1,2,3,4-tetrahydroisoquinolin-7-yl)amino]pyrido[2,3-d]pyrimidin-5(8H)-one,
- 6-(2,6-dichlorophenyl)-2-(2',3'-dihydro-1'H-spiro[cyclopropane-1,4'-isoquinolin]-7'-ylamino)-8-methylpyrido[2,3-d]pyrimidin-5(8H)-one,
- 6-(2,6-dichlorophenyl)-2-{[2-(dimethylamino)-2,3-dihydro-1H-inden-5-yl]amino}-8-methylpyrido[2,3-d]pyrimidin-5(8H)-one,
- 8-cyclopropyl-6-(2,6-dichlorophenyl)-2-[(2,4,4-trimethyl-1,2,3,4-tetrahydroisoquinolin-7-yl)amino]pyrido[2,3-d]pyrimidin-5(8H)-one,
- 8-cyclopropyl-6-(2,6-dichlorophenyl)-2-(2',3'-dihydro-1'H-spiro[cyclopropane-1,4'-isoquinolin]-7'-ylamino)pyrido[2,3-d]pyrimidin-5(8H)-one,
- 8-cyclopropyl-6-(2,6-dichlorophenyl)-2-{[2-(dimethylamino)-2,3-dihydro-1H-inden-5-yl]amino}pyrido[2,3-d]pyrimidin-5(8H)-one,
- 6-(2,6-dichlorophenyl)-2-{[4-(4-methylpiperazin-1-yl)phenyl]amino}-8-(propan-2-yl)pyrido[2,3-d]pyrimidin-5(8H)-one,
- 6-(2,6-dichlorophenyl)-2-{[4-(4-methylpiperazin-1-yl)phenyl]amino}-8-(oxetan-3-yl)pyrido[2,3-d]pyrimidin-5(8H)-one,
- 8-tert-butyl-6-(2,6-dichlorophenyl)-2-{[4-(4-methylpiperazin-1-yl)phenyl]amino}pyrido[2,3-d]pyrimidin-5(8H)-one,
- 6-(2,6-dichlorophenyl)-8-(4-methoxybenzyl)-2-[(2'-methyl-2',3'-dihydro-1'H-spiro[cyclopropane-1,4'-isoquinolin]-7'-yl)amino]pyrido[2,3-d]pyrimidin-5(8H)-one,
- 6-(2,6-dichlorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one,
- 6-(2,6-dichlorophenyl)-8-ethyl-2-{[4-(4-methylpiperazin-1-yl)phenyl]amino}pyrido[2,3-d]pyrimidin-5(8H)-one,
- 6-(2,6-dichlorophenyl)-8-ethyl-2-[(2'-methyl-2',3'-dihydro-1'H-spiro[cyclopropane-1,4'-isoquinolin]-7'-yl)amino]pyrido[2,3-d]pyrimidin-5(8H)-one,
- 6-(2-chloro-6-fluorophenyl)-8-methyl-2-{[4-(4-methylpiperazin-1-yl)phenyl]amino}pyrido[2,3-d]pyrimidin-5(8H)-one,
- 6-(2-chloro-6-fluorophenyl)-8-methyl-2-[(2'-methyl-2',3'-dihydro-1'H-spiro[cyclopropane-1,4'-isoquinolin]-7'-yl)amino]pyrido[2,3-d]pyrimidin-5(8H)-one,
- 6-(2-chloro-6-fluorophenyl)-8-(4-methoxybenzyl)-2-{[4-(4-methylpiperazin-1-yl)phenyl]amino}pyrido[2,3-d]pyrimidin-5(8H)-one,
- 6-(2-chloro-6-fluorophenyl)-8-(4-methoxybenzyl)-2-[(2'-methyl-2',3'-dihydro-1'H-spiro[cyclopropane-1,4'-isoquinolin]-7'-yl)amino]pyrido[2,3-d]pyrimidin-5(8H)-one,
- 6-(2-chloro-6-fluorophenyl)-8-cyclopropyl-2-{[4-(4-methylpiperazin-1-yl)phenyl]amino}pyrido[2,3-d]pyrimidin-5(8H)-one,
- 6-(2-chloro-6-fluorophenyl)-8-cyclopropyl-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2-chloro-6-fluorophenyl)-2-[(2'-methyl-2',3'-dihydro-1'H-spiro[cyclopropane-1,4'-isoquinolin]-7'-yl)amino]pyrido[2,3-d]pyrimidin-5(8H)-one, 6-(2-chloro-6-fluorophenyl)-2-{[4-(4-methylpiperazin-1-yl)phenyl]amino}pyrido[2,3-d]pyrimidin-5(8H)-one, 6-(2,6-dichlorophenyl)-2-{[2-(dimethylamino)-2,3-dihydro-1H-inden-5-yl]amino}pyrido[2,3-d]pyrimidin-5(8H)-one, 6-(2,6-dichlorophenyl)-2-[(2,4,4-trimethyl-1,2,3,4-tetrahydroisoquinolin-7-yl)amino]pyrido[2,3-d]pyrimidin-5(8H)-one, 6-(2,6-dichlorophenyl)-2-(2',3'-dihydro-1'H-spiro[cyclopropane-1,4'-isoquinolin]-7'-ylamino)pyrido[2,3-d]pyrimidin-5(8H)-one, 6-(2,6-dichlorophenyl)-2-({4-[4-(dimethylamino)piperidin-1-yl]phenyl}amino)-8-methylpyrido[2,3-d]pyrimidin-5(8H)-one, 6-(2,6-dichlorophenyl)-8-methyl-2-(1,2,3,4-tetrahydroisoquinolin-6-ylamino)pyrido[2,3-d]pyrimidin-5(8H)-one, 6-(2,6-dichlorophenyl)-2-[(4,4-dimethyl-1,2,3,4-tetrahydroisoquinolin-7-yl)amino]-8-methylpyrido[2,3-d]pyrimidin-5(8H)-one, 6-(2,6-dichlorophenyl)-8-methyl-2-{[4-(morpholin-4-yl)phenyl]amino}pyrido[2,3-d]pyrimidin-5(8H)-one, 6-(2,6-dichlorophenyl)-2-(2,3-dihydro-1H-isoindol-5-ylamino)-8-methylpyrido[2,3-d]pyrimidin-5(8H)-one, 6-(2,6-dichlorophenyl)-8-methyl-2-{[4-(1-methylpiperidin-4-yl)phenyl]amino}pyrido[2,3-d]pyrimidin-5(8H)-one, 6-(2,6-dichlorophenyl)-8-methyl-2-(1,2,3,4-tetrahydroisoquinolin-7-ylamino)pyrido[2,3-d]pyrimidin-5(8H)-one, 6-(2,6-dichlorophenyl)-8-methyl-2-[(2-methyl-1,2,3,4-tetrahydroisoquinolin-7-yl)amino]pyrido[2,3-d]pyrimidin-5(8H)-one, 6-(2,6-dichlorophenyl)-8-methyl-2-[(2-methyl-2,3-dihydro-1H-isoindol-5-yl)amino]pyrido[2,3-d]pyrimidin-5(8H)-one, 6-(2,6-dichlorophenyl)-8-methyl-2-[(2-methyl-1,2,3,4-tetrahydroisoquinolin-6-yl)amino]pyrido[2,3-d]pyrimidin-5(8H)-one, 5-{[6-(2,6-dichlorophenyl)-8-methyl-5-oxo-5,8-dihydropyrido[2,3-d]pyrimidin-2-yl]amino}-1H-isoindole-1,3(2H)-dione, 6-(2,6-dichlorophenyl)-8-methyl-2-{[2-(4-methylpiperazin-1-yl)-2,3-dihydro-1H-inden-5-yl]amino}pyrido[2,3-d]pyrimidin-5(8H)-one, 6-(2,6-dichlorophenyl)-8-methyl-2-(4,5,6,7-tetrahydrothieno[3,2-c]pyridin-2-ylamino)pyrido[2,3-d]pyrimidin-5(8H)-one, 6-(2,6-dichlorophenyl)-8-methyl-2-{[2-(4-methylpiperazin-1-yl)pyrimidin-5-yl]amino}pyrido[2,3-d]pyrimidin-5(8H)-one, 6-(2,6-dichlorophenyl)-8-methyl-2-[(1,1,2-trimethyl-2,3dihydro-1H-isoindol-5-yl)amino]pyrido[2,3d]pyrimidin-5(8H)-one;

6-(2,6-dichlorophenyl)-8methyl-2-({4-[(1-methylpiperidin-4yl)amino]phenyl}amino)pyrido[2,3d]pyrimidin-5(8H)-one, 6-(2,6-dichlorophenyl)-2-({2-[4-(dimethylamino)piperidin-1-yl]pyrimidin-5yl}amino)-8-methylpyrido[2,3-d]pyrimidin-5(8H)-one, 6-(2,6-dichlorophenyl)-8-methyl-2-({4-[(3R)-pyrrolidin-3-ylamino]phenyl}amino)pyrido[2,3-d]pyrimidin-5(8H)-one, 6-(2,6-dichlorophenyl)-8-methyl-2-({4-[(3S)-pyrrolidin-3-ylamino]phenyl}amino)pyrido[2,3-d]pyrimidin-5(8H)-one, 6-(2,6-dichlorophenyl)-2-[(1,1-dimethyl-2,3-dihydro-1H-isoindol-5-yl)amino]-8-methylpyrido[2,3-d]pyrimidin-5(8H)-one, 6-(2,6-dichlorophenyl)-8-methyl-2-{[4-(piperdin-4ylamino)phenyl]amino}pyrido [2,3-d]pyrimidin-5(8H)-one, 6-(2,6-dichlorophenyl)-8-methyl-2-({4[(1-methylpyrrolidin-3yl)amino]phenyl}amino)pyrido[2,3-d]pyrimidin-5(8H)-one, 6-(2,6-dichlorophenyl)-8-methyl-2-({4-[(1-methylpiperidin-4-yl)oxy]phenyl}amino)pyrido[2,3-d]pyrimidin-5(8H)-one, 6-(2-chloro-6fluorophenyl)-8-methyl-2-({4-[(1-methylpiperdin-4-yl)amino]phenyl}amino)pyrido[2,3-d]pyrimidin-5(8H)-one, 6-(2-chloro-6-fluorophenyl)-8-methyl-2-[(1,1,2-trimethyl-2,3-dihydro-1H-isoindol-5-yl)amino]pyrido[2,3-d]pyrimidin-5(8H)-one, methyl 5-{[6-(2,6-dichlorophenyl)-8-methyl-5-oxo-5,8-dihydropyrido[2,3-]pyrimidin-2-yl]amino}-2-(4-methylpiperazin-1-yl)benzoate, 6-(2,6-dichlorophenyl)-2-({2-[4-(dimethylamino)piperidin-1-yl]-2,3-dihydro-1H-inden-5-yl}amino)-8-methylpyrido[2,3-d]pyrimidin-5(8H)-one, 6-(2-chloro-6-fluorophenyl)-8-methyl-2-{[4-(piperdin-4ylamino)phenyl]amino}pyrido[2,3-d]pyrimidin-5(8H)-one, 6-(2-chloro-6-fluorophenyl)-8-methyl-2-(1,2,3,4-tetrahydroisoquinolin-7-ylamino)pyrido[2,3-d]pyrimidin-5(8H)-one, 6-(2-chloro-6-fluorophenyl)-8methyl-2-(1,2,3,4-tetrahydroisoquinolin-6ylamino)pyrido[2,3-d]pyrimidin-5(8H)-one, 6-(2,6-dichlorophenyl)-2-[(4-{[trans-4(dimethylamino)cyclohexyl]amino}phenyl)amino]-8-methylpyrido[2,3-d]pyrimidin-5(8H)-one, 6-(2,6-dichlorophenyl)-2-[(4-{[cis-4-(dimethylamino)cyclohexyl]amino}phenyl)amino]-8methylpyrido[2,3d]pyrimidin-5(8H)-one, 6-(2,6-dichlorophenyl)-2-[(4-{4-[3-(dimethylamino)propyl]piperazin-1-yl}phenyl)amino]-8-methylpyrido[2,3-d]pyrimidin-5(8H)-one, and 6-(2,6-dichlorophenyl)-2-[(4-{4-[2-(dimethylamino)ethyl]piperazin-1-yl}phenyl)amino]-8methylpyrido[2,3-d]pyrimidin-5(8H)-one.

22. A pharmaceutical composition comprising a compound or pharmaceutically acceptable salt of claim 1 and pharmaceutically acceptable excipient.

\* \* \* \* \*